US011078291B2

(12) United States Patent
Sussman et al.

(10) Patent No.: US 11,078,291 B2
(45) Date of Patent: Aug. 3, 2021

(54) BCMA ANTIBODIES AND USE OF SAME TO TREAT CANCER AND IMMUNOLOGICAL DISORDERS

(71) Applicant: Seagen Inc., Bothell, WA (US)

(72) Inventors: Django Sussman, Seattle, WA (US); Maureen Ryan, Bellevue, WA (US); Lori Westendorf, Snohomish, WA (US); Michael Feldhaus, Lebanon, NH (US)

(73) Assignee: Seagen Inc., Bothell, WA (US)

( * ) Notice: Subject to any disclaimer, the term of this patent is extended or adjusted under 35 U.S.C. 154(b) by 0 days.

(21) Appl. No.: 16/411,867

(22) Filed: May 14, 2019

(65) Prior Publication Data

US 2020/0002431 A1   Jan. 2, 2020

Related U.S. Application Data

(63) Continuation of application No. 15/434,921, filed on Feb. 16, 2017, now abandoned.

(60) Provisional application No. 62/396,084, filed on Sep. 16, 2016, provisional application No. 62/296,594, filed on Feb. 17, 2016.

(51) Int. Cl.
| | | |
|---|---|---|
| *A61K 47/68* | (2017.01) | |
| *C07K 16/28* | (2006.01) | |
| *A61K 38/05* | (2006.01) | |
| *A61P 35/00* | (2006.01) | |
| *A61K 31/40* | (2006.01) | |
| *A61K 31/5517* | (2006.01) | |
| *A61K 39/00* | (2006.01) | |

(52) U.S. Cl.
CPC .......... *C07K 16/2878* (2013.01); *A61K 31/40* (2013.01); *A61K 31/5517* (2013.01); *A61K 38/05* (2013.01); *A61K 47/6803* (2017.08); *A61K 47/6849* (2017.08); *A61K 47/6851* (2017.08); *A61P 35/00* (2018.01); *A61K 2039/505* (2013.01); *C07K 2317/14* (2013.01); *C07K 2317/24* (2013.01); *C07K 2317/41* (2013.01); *C07K 2317/522* (2013.01); *C07K 2317/524* (2013.01); *C07K 2317/71* (2013.01); *C07K 2317/72* (2013.01); *C07K 2317/732* (2013.01); *C07K 2317/734* (2013.01); *C07K 2317/76* (2013.01)

(58) Field of Classification Search
CPC .................. C07K 16/2878; A61K 47/6849
See application file for complete search history.

(56) References Cited

U.S. PATENT DOCUMENTS

| | | |
|---|---|---|
| 4,816,567 A | 3/1989 | Cabilly et al. |
| 5,047,335 A | 9/1991 | Paulson et al. |
| 5,225,539 A | 7/1993 | Winter |
| 5,278,299 A | 1/1994 | Wong et al. |
| 5,510,261 A | 4/1996 | Goochee et al. |
| 5,530,101 A | 6/1996 | Queen et al. |
| 5,585,089 A | 12/1996 | Queen et al. |
| 5,624,821 A | 4/1997 | Winter et al. |
| 5,834,597 A | 11/1998 | Tso et al. |
| 5,859,205 A | 1/1999 | Adair et al. |
| 6,407,213 B1 | 6/2002 | Carter et al. |
| 6,881,557 B2 | 4/2005 | Foote |
| 7,083,785 B2 | 8/2006 | Browning et al. |
| 7,138,501 B2 | 11/2006 | Ruben et al. |
| 7,498,298 B2 | 3/2009 | Doronina et al. |
| 7,521,541 B2 | 4/2009 | Eigenbrot et al. |
| 7,659,241 B2 | 2/2010 | Senter et al. |
| 7,825,089 B2 | 11/2010 | Zhang et al. |
| 7,968,687 B2 | 6/2011 | McDonagh et al. |
| 8,343,928 B2 | 1/2013 | Doronina et al. |
| 8,455,622 B2 | 6/2013 | McDonagh et al. |
| 8,871,720 B2 | 10/2014 | Doronina et al. |
| 2007/0212733 A1 | 9/2007 | Martin |
| 2017/0051068 A1 | 2/2017 | Pillarisetti et al. |
| 2017/0218077 A1 | 8/2017 | Raum et al. |
| 2017/0233484 A1 | 8/2017 | Sussman et al. |
| 2017/0283504 A1 | 10/2017 | Wiltzius et al. |
| 2019/0023801 A1 | 1/2019 | Sussman et al. |
| 2019/0194338 A1 | 6/2019 | Sussman et al. |

FOREIGN PATENT DOCUMENTS

| | | |
|---|---|---|
| WO | WO01/12812 A2 | 2/2001 |
| WO | WO01/24811 A1 | 4/2001 |
| WO | WO03/062401 A2 | 7/2003 |
| WO | WO2005/075511 A1 | 8/2005 |
| WO | WO2006/036291 A2 | 4/2006 |
| WO | WO2008/070593 A2 | 6/2008 |
| WO | WO2009/135181 A2 | 11/2009 |
| WO | WO2010/104949 A2 | 9/2010 |
| WO | WO2011/047121 A1 | 4/2011 |
| WO | WO2012/066058 A1 | 5/2012 |
| WO | WO2012/078688 A2 | 6/2012 |
| WO | WO2012/078688 A3 | 6/2012 |
| WO | WO2012/118622 A1 | 9/2012 |

(Continued)

OTHER PUBLICATIONS

PCT Application No. PCT/US2017/018177, International Preliminary Report on Patentability dated Aug. 21, 2018, 5 pages.
U.S. Appl. No. 15/434,921, filed Feb. 16, 2017, Restriction Requirement dated May 8, 2018, 10 pages.
U.S. Appl. No. 15/434,921, filed Feb. 16, 2017, Response to Restriction Requirement dated May 8, 2018, as filed with USPTO on Aug. 8, 2018, 7 pages.

(Continued)

*Primary Examiner* — Gyan Chandra
(74) *Attorney, Agent, or Firm* — Seagen Inc.

(57) ABSTRACT

The invention provides humanized antibodies that specifically bind to BCMA. The antibodies are useful for treatment and diagnoses of various cancers and immune disorders as well as detecting BCMA.

66 Claims, 16 Drawing Sheets

Specification includes a Sequence Listing.

(56) References Cited

FOREIGN PATENT DOCUMENTS

| WO | WO2012/143498 A1 | 10/2012 |
|---|---|---|
| WO | WO2012/163805 A1 | 12/2012 |
| WO | WO2014/068079 A1 | 5/2014 |
| WO | WO2014/069079 A1 | 5/2014 |
| WO | WO2014/089335 A2 | 6/2014 |
| WO | WO2014/122143 A1 | 8/2014 |
| WO | WO2014/122144 A1 | 8/2014 |
| WO | WO2014/140243 A1 | 9/2014 |
| WO | WO2014/140248 A1 | 9/2014 |
| WO | WO2015/158671 A1 | 10/2015 |
| WO | WO2015/166073 A1 | 11/2015 |
| WO | WO2016/020332 A1 | 2/2016 |
| WO | WO2016/064749 A2 | 4/2016 |
| WO | WO2016/069919 A1 | 5/2016 |
| WO | WO2016/079081 A1 | 5/2016 |
| WO | WO2016/079177 A1 | 5/2016 |
| WO | WO2016/090327 A2 | 6/2016 |
| WO | WO2016/166629 A1 | 10/2016 |
| WO | WO2016/187068 A1 | 11/2016 |
| WO | WO2017/021450 A1 | 2/2017 |
| WO | WO2017/025038 A1 | 2/2017 |
| WO | WO2017/083511 A1 | 5/2017 |
| WO | WO2017/093942 A1 | 6/2017 |
| WO | WO2017/143069 A1 | 8/2017 |
| WO | WO2018/151817 | 8/2018 |

OTHER PUBLICATIONS

U.S. Appl. No. 15/434,921, filed Feb. 16, 2017, Non-Final Office Action dated Sep. 27, 2018, 20 pages.
U.S. Appl. No. 15/434,921, filed Feb. 16, 2017, Response to Non-Final Office Action dated Sep. 27, 2018 as filed with USPTO on Dec. 19, 2018, 6 pages.
U.S. Appl. No. 16/151,012, filed Oct. 3, 2018, Non-Final Office Action dated Dec. 12, 2018, 19 pages.
U.S. Appl. No. 16/151,012, filed Oct. 3, 2018, Response to Non-Final Office Action dated Dec. 12, 2018 as filed with USPTO on Mar. 12, 2019, 7 pages.
EP Application No. 17753839.4, extended European Search Report and Search Opinion dated Sep. 23, 2019, 10 pages.
Daumke, et al., "Generation of an antibody targeting B cell maturation antigen for the treatment of multiple myeloma and autoimmune diseases", Dissertation, Available at: http://www.diss.fu-berlin.de/diss/servlets/MCRFileNodeServlet/FUDISS_derivate_000000016111/Dissertation_FO_ohne.pdf, (Apr. 1, 2014).
PCT Application No. PCT/US2017/018177, Search Report and Written Opinion dated May 8, 2017, 9 pages.
Akewanlop, et al., "Phagocytosis of Breast Cancer Cells Mediated by Anti-MUC-1 Monoclonal Antibody, DF3, and Its Bispecific Antibody", Cancer Research, 61, pp. 4061-4065, (May 2001).
Alley, et al., "Antibody—drug conjugates: targeted drug delivery for cancer", Current Opinion in Chemical Biology, 14, pp. 529-537, (2010).
Ananth, et al. "Transforming Growth Factor B1 is a Target for the von Hippel-Lindau Tumor Suppressor and a Critical Growth Factor for Clear Cell Renal Carcinoma", Cancer Research, 59, pp. 2210-2216, (May 1999).
Barth, et al., "Ki-4(scFv)—ETA', a new recombinant anti-CD30 immunotoxin with highly specific cytotoxic activity against disseminated Hodgkin tumors in SCID mice", Blood, vol. 95, No. 12, pp. 3909-3914, (Jun. 15, 2000).
Bernheim, et al., "Cytogenetic Studies in Three Xenografted Nasopharyngeal Carcinomas", Cancer Genet Cytogenet, 66, pp. 11-15, (1993).
Boyd, et al., "The Effect of the Removal of Sialic Acid, Galactose and Total Carbohydrate on the Functional Activity of Campath-IH", Molecular Immunology, vol. 32, No. 17/18, pp. 1311-1318, (1995).
Breistøl, et al., "Antitumor Activity of P-4055 (Elaidic Acid-Cytarabine) Compared to Cytarabine in Metastatic and s.c. Human Tumor Xenograft Models", Cancer Research, 59, pp. 2944-2949, (Jun. 15, 1999).
Busson, et al., "Establishment and Characterization of Three Transplantable Ebv-Containing Nasopharyngeal Carcinomas", Int. J. Cancer, 42, pp. 599-606, (1988).
Carter, et al., "Antibody-Drug Conjugates for Cancer Therapy", Cancer J., 14, pp. 154-169, (2008).
Cattan, et al., "The C.B.17 SCID Mouse Strain as a Model for Human Disseminated Leukaemia and Myeloma In Vivo", Leukemia Research, vol. 18, No. 7, pp. 513-522, (1994).
Cattan, et al., "A comparison of a CB17 scid mouse model and the tetrazolium-dye assay using human haematological tumour cell lines", Cancer Chemother Pharmacol, 38, pp. 548-552, (1996).
Chamow, et al., "Immunoadhesins: principles and applications", Tibtech, vol. 14, pp. 52-60, (Feb. 1996).
Chiu, et al., "Hodgkin lymphoma cells express TACI and BCMA receptors and generate survival and proliferation signals in response to BAFF and APRIL", Blood, vol. 109, No. 2, pp. 729-739, (2007).
Chotia, et al., "Canonical Structures for the Hypervariable Regions of Immunoglobulins", J. Mol. Biol., 196, pp. 901-917, (1987).
Chotia, et al., "Conformations of immunoglobulin hypervariable regions", Nature, vol. 342, No. 21, pp. 877-883, (Dec. 1989).
Clackson, et al., "Making antibody fragments using phage display libraries", Nature, vol. 352, pp. 624-628, (Aug. 1991).
Co, et al., "Chimeric and humanized antibodies with specificity for the CD33 antigen", The Journal of Immunology, vol. 148, No. 4, pp. 1149-1154, (Feb. 1992).
Datta, et al., "The 104-123 Amino Acid Sequence of the B-domain of von Hippel-Lindau Gene Product is Sufficient to Inhibit Renal Tumor Growth and Invasion", Cancer Research, 61, pp. 1768-1775, (Mar. 2001).
Davies, et al., "Expression of GnTlll in a Recombinant Anti-CD20 CHO Production Cell Line: Expression of Antibodies with Altered Glycoforms Leads to an Increase in ADCC Through Higher Affinity for FcyRlll", Biotechnology and Bioengineering, vol. 74, No. 4, pp. 288-294, (Aug. 2001).
De Bont, et al., "Mobilized Human CD34+ Hematopoietic Stem Cells Enhance Tumor Growth in a Nonobese Diabetic/Severe Combined Immunodeficient Mouse Model of Human Non-Hodgkin's Lymphoma", Cancer Research, 61, pp. 7654-7659, (Oct. 15, 2001).
Dubowchik, et al., "Receptor-mediated and enzyme-dependent targeting of cytotoxic anticancer drugs", Pharmacology & Therapeutics, 83, pp. 67-123, (1999).
Ghetie, et al., "Multiple Roles for the Major Histocompatibility Complex Class I-Related Receptor FcRn", Annu. Rev. Immunol. ,18, pp. 739-766, (2000).
Ghetie, et al., "Transcytosis and Catabolism of Antibody", Immunologic Research, vol. 25, No. 2, pp. 97-113, (2002).
Ghetie, et al., "Disseminated or Localized Growth of a Human B-Cell Tumor (Daudi) in Scid Mice", Int. J. Cancer, 45, pp. 481-485, (1990).
Ghetie, et al. "Anti-CD19 Inhibits the Growth of Human B-Cell Tumor Lines In Vitro and of Daudi Cells in SCID Mice by Inducing Cell Cycle Arrest", Blood, vol. 83, No. 5, pp. 1329-1336, (Mar. 1994).
Gonzales, et al., "SDR grafting of a murine antibody using multiple human germline templates to minimize its immunogenicity", Molecular Immunology, 41, pp. 863-872, (2004).
Hara, et al., "Over Expression of Inhibitor of Caspase 3 Activated Deoxyribonuclease in Human Renal Cell Carcinoma Cells Enhances Their Resistance to Cytotoxic Chemotherapy In Vivo", The Journal of Urology, vol. 166, pp. 2491-2494, (Dec. 2001).
Hinton, et al., "Engineered Human IgG Antibodies with Longer Serum Half-lives in Primates", The Journal of Biological Chemistry, vol. 279, No. 8, pp. 6213-6216, (Feb. 2004).
Hsu, et al., "Differential N-Glycan Patterns of Secreted and Intracellular IgG Produced in *Trichoplusia ni* Cells", The Journal of Biological Chemistry, vol. 272, No. 14, pp. 9062-9070, (1997).
Idusogie, et al., "Engineered Antibodies with Increased Activity to Recruit Complement", The Journal of Immunology, 166, pp. 2571-2575, (2001).

(56) References Cited

OTHER PUBLICATIONS

Iwahashi, et al., "CDR substitutions of a humanized monoclonal antibody (CC49): contributions of individual CDRs to antigen binding and immunogenicity", Molecular Immunology, 36, pp. 1079-1091, (1999).
Jefferis, et al., "Glycosylation of Antibody Molecules: Structural and Functional Significance", Chem. Immunol., vol. 65, pp. 111-128, (1997).
Jelinek, et al., "Human B Lymphocyte Malignancies: Exploitation of BLyS and APRIL and Their Receptors", Curr Dir Autoimmin., vol. 8, pp. 266-288, (2005).
Johns, et al., "Novel Monoclonal Antibody Specific for the De2-7 Epidermal Growth Factor Receptor (EGFR) That Also Recognizes the EGFR Expressed in Cells Containing Amplification of the EGFR Gene", Int. J. Cancer, 98, pp. 398-408, (2002).
Junghans, et al., "Anti-Tac-H, a Humanized Antibody to the Interleukin 2 Receptor with New Features for Immunotherapy in Malignant and Immune Disorders", Cancer Research, 50, pp. 1495-1502, (Mar. 1990).
Kamel-Reid, et al., "Engraftment of Immune-Deficient Mice with Human Hematopoietic Stem Cells", Science, vol. 242, pp. 1706-1709, (Dec. 1988).
Kataoka, et al., "The role of donor T cells for target organ injuries in acute and chronic graft-versus-host disease", Immunology, 103, pp. 310-318, (2001).
Köhler, et al., "Continuous cultures of fused cells secreting antibody of predefined specificity", Nature, vol. 256, pp. 495-197, (Aug. 1975).
Kontermann, et al., "Complement recruitment using bispecific diabodies", Nature Biotechnology. vol. 15, pp. 629-631, (Jul. 1997).
Kostelny, et al., "Formation of a bispecific antibody by the use of leucine zippers", The Journal of Immunology, 148, pp. 1547-1553, (1992).
Kreitman, et al., "Complete Regression of Human B-Cell Lymphoma Xenografts in Mice Treated With Recombinant Anti-CD22 Immunotoxin Rfb4(dsFv)-PE38 at Doses Tolerated by Cynomolgus Monkeys", Int. J. Cancer, 81, pp. 148-155, (1999).
Lazar, et al., "Engineered antibody Fc variants with enhanced effector function", PNAS, vol. 103, No. 11, pp. 4005-4010, (Mar. 2006).
Lund, et al., "Multiple interactions of IgG with its core oligosaccharide can modulate recognition by complement and human Fc gamma receptor I and influence the synthesis of its oligosaccharide chains", The Journal of Immunology, 157, pp. 4963-4969, (1996).
Ma, et al., "Radioimmunotherapy for model B cell malignancies using $^{90}$Y-labeled anti-CD19 and anti-CD20 monoclonal antibodies", Leukemia, 16, pp. 60-66, (2002).
Malhotra, et al., "Glycosylation changes of IgG associated with rheumatoid arthritis can activate complement via the mannose-binding protein", Nature Medicine, vol. 1, No. 3, pp. 237-243, (Mar. 1995).
Marks, et al., "By-passing Immunization Human Antibodies from V-gene Libraries Displayed on Phage", J. Mol. Boil., 222, pp. 581-597, (1991).
Matsuda, et al., "Development of atopic dermatitis-like skin lesion with IgE hyperproduction in NC/Nga mice", International Immunology, vol. 9, No. 3, pp. 461-466, (1996).
McCune, et al., "The SCID-hu Mouse: Murine Model for the Analysis of Human Hematolymphoid Differentiation and Function", Science, vol. 241, pp. 1632-1639, (1988).
Miyake, et al., "Introducing the Clusterin Gene Into Human Renal Cell Carcinoma Cells Enhances Their Metastatic Potential", The Journal of Urology, vol. 167, pp. 2203-2208, (May 2002).
Mosier, et al., "Transfer of a functional human immune system to mice with severe combined immunodeficiency", Nature, vol. 335, pp. 256-259, (Sep. 15, 1988).
Niwa et al., "Defucosylated Chimeric Anti-CC Chemokine Receptor 4 IgG1 with Enhanced Antibody-Dependent Cellular Cytotoxicity Shows Potent Therapeutic Activity to T-Cell Leukemia and Lymphoma", Cancer Research, 64, pp. 2127-2133, (Mar. 15, 2004).

Novak, et al., "Expression of BCMA, TACI, and BAFF-R in multiple myeloma: a mechanism for growth and survival", Blood, vol. 103, No. 2, pp. 689-694, (Jan. 15, 2004).
O'Connor, et al., "BCMA is Essential for the Survival of Long-lived Bone Marrow Plasma Cells", The Journal of Experimental Medicine, vol. 199, No. 1, pp. 91-97, (Jan. 5, 2004).
Ochakovskaya, et al., "Therapy of Disseminated B-Cell Lymphoma Xenografts in Severe Combined Immunodeficient Mice with an Anti-CD74 Antibody Conjugated with $^{111}$Indium, $^{67}$Gallium, or $^{90}$Yttrium", Clinical Cancer Research, vol. 7, pp. 1505-1510, (Jun. 2001).
Okazaki, et al., "Fucose Depletion from Human IgG1 Oligosaccharide Enhances Binding Enthalpy and Association Rate Between IgG1 and FcyRllla", J. Mol. Biol., 336, pp. 1239-1249, (2004).
Oakley et al., "Development of orally active inhibitors of protein and cellular fucosylation", PNAS Early Edition, pp. 1-6, available at: www.pnas.org/cgi/doi/10.1073/pnas.1222263110, (2013).
Oakley, et al., "Development of orally active inhibitors of protein and cellular fucosylation", PNAS, vol. 110, No. 14, pp. 5404-5409, (Apr. 2013).
Padlan, "Possible Procedure for Reducing the Immunogenicity of Antibody Variable Domains While Preserving Their Ligand-Binding Properties", Molecular Immunology, vol. 28, No. 4/5, pp. 489-498, (1991).
Palma, et al., "Anti-tumour activity of tachykinin $NK_1$ receptor antagonists on human glioma U373 MG xenograft", British Journal of Cancer, 82(2), pp. 480-487, (2000).
Pascalis, et al., "Grafting of "Abbreviated" Antibody Less Immunogenic Humanized Monoclonal Essential for Ligand Contact to Engineer a Containing Specificity-Determining Residues Complementarity-Determining Regions", The Journal of Immunology, 169, pp. 3076-3084, (2002).
Press, et al., "A comparative evaluation of conventional and pretargeted radioimmunotherapy of CD20-expressing lymphoma xenografts", Blood, vol. 98, No. 8, pp. 2535-2543, (Oct. 2001).
Prewett, et al., "Mouse-Human Chimeric Anti-Epidermal Growth Factor Receptor Antibody C225 Inhibits the Growth of Human Renal Cell Carcinoma Xenografts in Nude Mice", Clinical Cancer Research, vol. 4, pp. 2957-2966, (Dec. 1998).
Queen, et al., "Cell-Type Specific Regulation of a $_K$ Immunoglobulin Gene by Promoter and Enhancer Elements", Immunological Reviews, No. 89, pp. 49-68, (1986).
Rudikoff, et al., "Single amino acid substitution altering antigen-binding specificity", Proc. Natl. Acad. Sci. USA, vol. 79, pp. 1979-1983, (Mar. 1982).
Ryan, et al., "Antibody targeting of B-cell maturation antigen on malignant plasma cells", Molecular Cancer Therapeutics, 6(11), pp. 3009-3018, (Nov. 2007).
Sasakawa, et al., "Atopic Dermatitis-Like Skin Lesions Induced by Topical Application of Mite Antigens in NC/Nga Mice", Int. Arch. Allergy Immunol., 126, pp. 239-247, (2001).
Shi, et al., "Inhibition of renal cell carcinoma angiogenesis and growth by antisense oligonucleotides targeting vascular endothelial growth factor", British Journal of Cancer, 87, pp. 119-126, (2002).
Shields, et al., "High Resolution Mapping of the Binding Site on Human IgG1 for FcyRl, FcyRll, FcyRlll, and FcRn and Design of IgG1 Variants with Improved Binding to the FcyR" The Journal of Biological Chemistry, vol. 276, No. 9, pp. 6591-6604, (Mar. 2001).
Sheilds, et al., "Lack of Fucose on Human IgG1 N-Linked Oligosaccharide Improves Binding to Human FcyRlll and Antibody-dependent Cellular Toxicity", The Journal of Biological Chemistry, vol. 277, No. 30, pp. 26733-26740, (2002).
Shinkawa, et al., "The Absence of Fucose but Not the Presence of Galactose or Bisecting N-Acetylglucosamine of Human IgG1 Complex-type Oligosaccharides Shows the Critical Role of Enhancing Antibody-Dependent Cellular Cytotoxicity", The Journal of Biological Chemistry, vol. 278, No. 5, pp. 3466-3473, (Jan. 2003).
Shopes, et al., "A Genetically Engineered Human Igg Mutant With Enhanced Cytolytic Activity", The Journal of Immunology, vol. 148, No. 9, pp. 2918-2922, (May 1, 1992).
Slayback, et al., "Genetic factors influencing the development of chronic graft-versus-host disease in a murine model", Bone Marrow Transplantation, 26, pp. 931-938, (2000).

(56) References Cited

OTHER PUBLICATIONS

Smith, et al., "Addition of a mu-tailpiece to IgG results in polymeric antibodies with enhanced effector functions including complement-mediated cytolysis by IgG4", J. Immunol, 154, pp. 2226-2236, (1995).

Songsivilai, et al., "Bispecific antibody: a tool for diagnosis and treatment of disease", Clin. Exp. Immunol., 79, pp. 315-321, (1990).

Tai, et al., "Targeting B-cell maturation antigen in multiple myeloma", Immunotherapy, 7(11), pp. 1187-1199, (2015).

Tamura, et al., "Structural Correlates of an Anticarcinoma Antibody: Identification of Specificity-Determining Residues (SDRs) and Development of a Minimally Immunogenic Antibody Variant by Retention of SDRs Only", The Journal of Immunology, J. Immunol., 164, pp. 1432-1441, (2000).

Tesciuba, et al., "Inducible Costimulator Regulates Th2-Mediated Inflammation, but Not Th2 Differentiation, in a Model of Allergic Airway Disease", J. Immunol., 167, pp. 1996-2003, (2001).

Tomkinson, et al., "A Murine IL-4 Receptor Antagonist That Inhibits IL-4- and IL-13-Induced Responses Prevents Antigen-Induced Airway Eosinophilia and Airway Hyperresponsiveness", J. Immunol., 166, pp. 5792-5800, (2001).

Tournoy, et al., "The Allergen-Induced Airway Hyperresponsiveness in a Human-Mouse Chimera Model of Asthma is T Cell and IL-4 and IL-5 Dependent", J. Immunol., 166, pp. 6982-6991, (2001).

Uchida, et al., "The Innate Mononuclear Phagocyte Network Depletes B Lymphocytes through Fc Receptor—dependent Mechanisms during Anti-CD20 Antibody Immunotherapy", The Journal of Experimental Medicine, vol. 199, No. 12, pp. 1659-1669, (Jun. 2004).

Umaña, et al., "Engineered glycoforms of an antineuro-blastoma IgG1 with optimized antibodydependent cellular cytotoxic activity", Nature Biotechnology, vol. 17, pp. 176-180, (Feb. 1999).

Vajdo, et al., "Comprehensive Functional Maps of the Antigenbinding Site of an Anti-ErbB2 Antibody Obtained with Shotgun Scanning Mutagenesis", J. Mol. Biol., 320, pp. 415-428, (2002).

Vestergaard, et al., "The NC/Nga mouse: a model for atopic dermatitis", Molecular Medicine Today, vol. 6, pp. 209-210, (May 2000).

Wahl, et al., "The Anti-CD30 Monoclonal Antibody SGN-30 Promotes Growth Arrest and DNA Fragmentation in Vitro and Affects Antitumor Activity in Models of Hodgkin's Disease", Cancer Research, 62, pp. 3736-3742, (Jul. 1, 2002).

Wallweber, et al., "The Crystal Structure of a Proliferation-inducing Ligand, APRIL", J. Mol. Biol., 343, pp. 283-290, (2004).

Watanabe, et al., "Antibody dependent cellular phagocytosis (ADCP) and antibody dependent cellular cytotoxicity (ADCC) of breast cancer cells mediated by bispecific antibody, MDX-210" Breast Cancer Research and Treatment, 53, pp. 199-207, (1999).

Wittwer, et al., "Glycosylation at Asn-184 Inhibits the Conversion of Single-Chain to Two-Chain Tissue-Type Plasminogen Activator by Plasmin", Biochemistry, 29, pp. 4175-4180, (1990).

Wright, et al., "Effect of glycosylation on antibody function: implications for genetic engineering", Tibtech, vol. 15, pp. 26-32, (Jan. 1997).

Wyss, et al., "The structural role of sugars in glycoproteins", Current Opinion in Biotechnology, 7, pp. 409-416, (1996).

Zellweger, et al., "Chemosensitization of Human Renal Cell Cancer Using Antisense Oligonucleotides Targeting the Antiapoptotic Gene Clusterin", Neoplasia, vol. 3, No. 4, pp. 360-367, (2001).

Caldas, et al., "Humanization of the anti-CD 18 antibody 6.7: an unexpected effect of a framework residue in binding to antigen", Molecular Immunology, 39, pp. 941-952, (2003).

Casadevall, et al., "Immunoglobulin isotype influences affinity and specificity", PNAS, vol. 109, No. 31, pp. 12272-12273, (Jul. 31, 2012).

Du et al., "Molecular Basis of Recognition of Human Osteopontin by 23C3, a Potential Therapeutic Antibody for Treatment of Rheumatoid Arthritis", J. Mol. Biol. 382, pp. 835-842, (2008).

Kunik, et al. "Structural Consensus among Antibodies Defines the Antigen Binding Site", PLoS Computational Biology, vol. 8, No. 2, pp. 1-12, (Feb. 2012).

Jelinek and Darce (2005) *Curr Dir Autoimmun.* Basel, Karger 8: 266-288

Wallweber (2004) *J Mol Biol* 343: 283-290

Fig. 7: Alignment of hSG16.17 Heavy Chain Variants with Human VH Acceptor Sequence, HV1-2/HJ3.

```
                          10        20        30        40        50
                 ....|....|....|....|....|....|....|....|....|....|....|....
Rat SG16.17 vH   ..N.L..R.ALV.......L..E........D...I...K.SH.KS...I.Y......Y.K.
Hu HV1-2/HJ3     QVQLVQSGAEVKKPGASVKVSCKASGYTFTGYYMHWVRQAPGQGLEWMGRINPNSGGTNY
hSG16.17 vH1     .......R............L..........D...I.............I.Y......Y.K.
hSG16.17 vH2     .....................L..........D.................I........Y...
hSG16.17 vH3     .....................L..........D...I.............I.Y......Y...
hSG16.17 vH4     ................................D.................I........Y...
Kabat CDRs                                      *****           **********
IMGT CDRs                                    ++++++++          ++++++++

60        70        80        90       100       110
                 |....|....|....|....|.........|....|....|.........|....|...
Rat SG16.17 vH   NEN.KTKA.M.A.K.TN...V.....T.E.SAT.F.T.YMWERVTGFFDF...P..K.....
Hu HV1-2/HJ3     AQKFQGRVTSTRDTSISTAYMELSRLRSDDTVVYYCAR-----------WGQGTMVTVSS
hSG16.17 vH1     NEN.KT.A.M.A.K...N...V............A...F.T.YMWERVTGFFDF.............
hSG16.17 vH2     ........M.A.K...N...V............A...F.T.YMWERVTGFFDF.............
hSG16.17 vH3     .......A.M.A.K...N...V............A...F.T.YMWERVTGFFDF.............
hSG16.17 vH4     .......A.M.A.K...N...V............A...F.T.YMWERVTGFFDF.............
Kabat CDRs       ******                           ************
IMGT CDRs                                        ++++++++++++++++
```

Fig. 8: Alignment of hSG16.17 Heavy Chain Variants with Human VH Acceptor Sequence; HV1-46/HJ3.

```
                          10        20        30        40        50
                 ....|....|....|....|....|....|....|....|....|....|....|....
Rat SG16.17 vH   ..N.L..R.ALV.......L..E........D...I...K.SH.KS...I.Y...NS.Y.K.
Hu HV1-46/HJ3    QVQLVQSGAEVKKPGASVKVSCKASGYTFTSYYMHWVRQAPGQGLEWMGIINPSGGSTSY
hSG16.17 vH5     ................................D...I.............I.Y...NS.Y.K.
hSG16.17 vH6     .......R............L...........D..................I.....NS.Y...
Kabat CDRs                                      *****           **********
IMGT CDRs                  |                 ++++++++          ++++++++

60        70        80        90       100       110
                 |....|....|....|....|.........|....|....|.........|....|...
Rat SG16.17 vH   NEN.KTKA...A.K..N.A.V...R.T...S.T.F.T.YMWERVTGFFDF...P..K.....
Hu HV1-46/HJ3    AQKFQGRVTMTRDTSTSTVYMELSSLRSEDTAVYYCAR-----------WGQGTMVTVSS
hSG16.17 vH5     NEN.KT.A...A.K..N.A.V.............F.T.YMWERVTGFFDF.............
hSG16.17 vH6     ............A.K..N.A.V.............F.T.YMWERVTGFFDF.............
Kabat CDRs       ******                           ************
IMGT CDRs                                        ++++++++++++++++
```

Fig. 9: Alignment of hSG16.17 Heavy Chain Variants

```
                        10        20        30        40        50
                ....|....|....|....|....|....|....|....|....|....|....|....
hSG16.17 vH1    QVQLVQSRAEVKKPGASVKLSCKASGYTFTDYYIHWVRQAPGQGLEWIGYINPNSGYTKY
hSG16.17 vH2    .......G............................M................R........N.
hSG16.17 vH3    .......G.............................................................N.
hSG16.17 vH4    .......G..........V.................M................R........N.
hSG16.17 vH5    .......G..........V................................................
hSG16.17 vH6    ....................................M................I........S.
Kabat CDRs                                  *****              ***********
IMGT  CDRs                                     ++++++++           ++++++++

60        70        80        90       100       110
                ....|....|....|....|....|........|....|....|....|........|....|...
hSG16.17 vH1    NENFKTRATMTADKSINTAYVELSRLRSDDTAVYFCTRYMWERVTGFFDFWGQGTMVTVSS
hSG16.17 vH2    AQK.QG.V....................................................
hSG16.17 vH3    AQK.QG.......................................................
hSG16.17 vH4    AQK.QG.......................................................
hSG16.17 vH5    ................T........S...E...............................
hSG16.17 vH6    AQK.QG.V........T........S...E...............................
Kabat CDRs      ******                          *************
IMGT  CDRs                                      ++++++++++++++++
```

Fig. 10: Alignment of hSG16.17 Light Chain Variants with Human VK Acceptor Sequence; KV1-12/KJ5.

```
                        10        20        30        40        50        60
                ....|....|....|....|....|....|....|....|....|....|....|....|
Rat SG16.17 vK  ........A.L...L.ET.S.E.L...ED...DD.......S...S.QV.V.TT.R...D....
Hu KV1-12/KJ5   DIQMTQSPSSVSASVGDRVTITCRASQGISSWLAWYQQKPGKAPKLLIYAASSLQSGVPS
hSG16.17 vK2    .........................L...ED...DD..............V.V.TT........
hSG16.17 vK3    ..............................ED...DD..............V.V.TT........
hSG16.17 vK4    .........................L...ED...DD..............V.V.TT.R.......
hSG16.17 vK5    ..............................ED...DD.......S......V.V.TT........
Kabat CDRs                                 ***********              *******
IMGT  CDRs                                    ++++++                  +++

70        80        90       100
                ....|....|....|....|....|....|....|....|....|...
Rat SG16.17 vK  .........R.S.K.IVM....E.D.F.QQTYKFPPT...A...RLDL...
Hu KV1-12/KJ5   RFSGSGSGTDFTLTISSLQPEDFATYYC---------FGGGTKVEIKR
hSG16.17 vK2    ............................F.QQTYKFPPT...........
hSG16.17 vK3    ............................F.QQTYKFPPT...........
hSG16.17 vK4    .....................M......D.F.QQTYKFPPT...........
hSG16.17 vK5    ............................F.QQTYKFPPT...........
Kabat CDRs                                  *********
IMGT  CDRs                                  +++++++++
```

Fig. 11: Alignment of hSG16.17 Light Chain Variants

```
                          10        20        30        40        50        60
               ....|....|....|....|....|....|....|....|....|....|....|....|
hSG16.17 vK2   DIQMTQSPSSVSASVGDRVTITCLASEDISDDLAWYQQKPGKAPKVLVYTTSSLQSGVPS
hSG16.17 vK3   .......................R....................................
hSG16.17 vK4   .........................................................R..
hSG16.17 vK5   .......................R.............S......................
Kabat CDRs                            ***********           *******
IMGT  CDRs                              ++++++                +++

70        80        90       100
               ....|....|....|....|....|....|....|....|....|....|...
hSG16.17 vK2   RFSGSGSGTDFTLTISSLQPEDFATYFCQQTYKFPPTFGGGTKVEIKR
hSG16.17 vK3   ................................................
hSG16.17 vK4   ..................M......D.......................
hSG16.17 vK5   ................................................
Kabat CDRs                                 *********
IMGT  CDRs                                +++++++++
```

Fig. 13

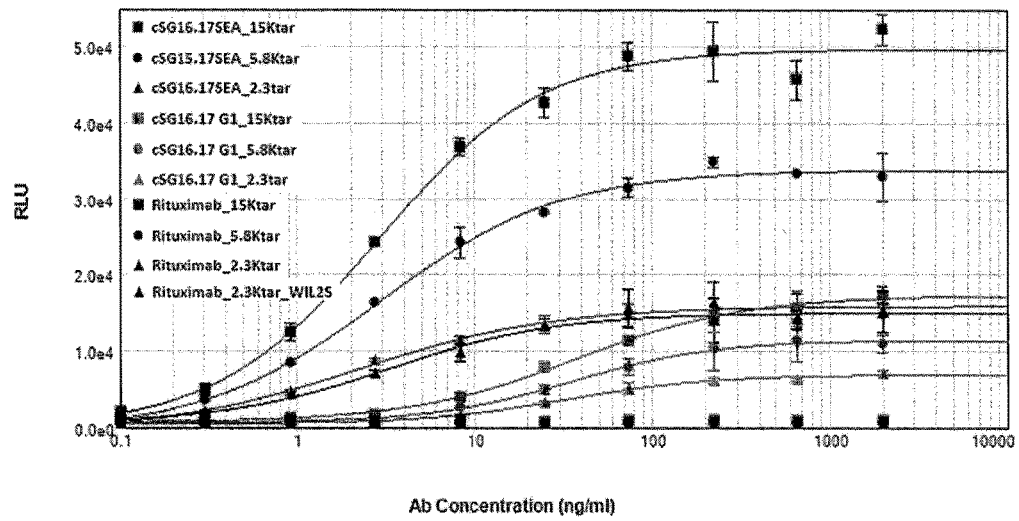

Fig. 14: Alignment of hSG16.45 Heavy Chain Variants with Human HV Acceptor Sequence, HV3-23/HJ3.

```
                        10        20        30        40        50
               ....|....|....|....|....|....|....|....|....|....|....
Rat SG16.45 vH ....V..........R..K...V......NDHW.T.I.....R....I.S.TNT..A...
Hu HV3-23/HJ3  EVQLLESGGGLVQPGGSLRLSCAASGFTFSSYAMSWVRQAPGKGLEWVSAISGSGGSTYY
hSG16.45 vH1   ..............................NDHW.T.I..........I.S.TNT..A...
hSG16.45 vH2   ..............................NDHW.T.I..........I...TNT..A...
hSG16.45 vH3   ..............................NDHW.T.I..........I...TNT..A...
hSG16.45 vH4   ..............................NDHW.T............I.S.TNT..A...
Kabat CDRs                                   *****            **********
IMGT CDRs                              ++++++++                 ++++++++

60        70        80        90       101       110
               ....|....|....|....|....|......|....|....|....|....|....|...
Rat SG16.45 vH L............A.S..........S....T...TSPGLYFDY....V......
Hu HV3-23/HJ3  ADSVKGRFTISRDNSKNTLYLQMNSLRAEDTAVYYCAK------WGQGTMVTVSS
hSG16.45 vH1   L...................................TSPGLYFDY....V......
hSG16.45 vH2   .....................................TSPGLYFDY....V......
hSG16.45 vH3   ................S....................TSPGLYFDY....V......
hSG16.45 vH4   ................S....................TSPGLYFDY...........
Kabat CDRs     ******                                *******
IMGT CDRs                                            +++++++++
```

Figure 15: Alignment of hSG16.45 Heavy Chain Variants with Human HV Acceptor Sequence; HV3-74/HJ3.

```
                        10        20        30        40        50
               ....|....|....|....|....|....|....|....|....|....|....|....
Rat SG16.45 vH ................R...K...V......NDH...T.I.....R...E.I.S.TNT.GA.Y.
Hu HV3-74/HJ3  EVQLVESGGGLVQPGGSLRLSCAASGFTFSSYWMHWVRQAPGKGLVWVSRINSDGSSTSY
hSG16.45 vH5   ................................NDH...T...............S.TNT.GA.Y.
Kabat CDRs                                     *****           ***********
IMGT CDRs                                  ++++++++          ++++++++

60        70        80        90       101       110
               |....|....|....|....|.......|....|....|....|...|....|...
Rat SG16.45 vH L................S..........S....T...TSPGLYFDY....V......
Hu HV3-74/HJ3  ADSVKGRFTISRDNAKNTLYLQMNSLRAEDTAVYYCAR-------WGQGTMVTVSS
hSG16.45 vH5   ....................................TSPGLYFDY...........
Kabat CDRs     ******                                *******
IMGT CDRs                                         ++++++++++
```

Figure 16: Alignment of hSG16.45 Heavy Chain Variants with Human HV Acceptor Sequence; HV3-9/HJ3.

```
                        10        20        30        40        50
               ....|....|....|....|....|....|....|....|....|....|....|....
Rat SG16.45 vH EVQLVESGGGLVQPGRSLKLSCVASGFTFNDHWMTWIRQAPGRGLEWISSITNTGGATYY
Hu HV3-9/HJ3   ....................R...A......D.YA.H.V.....K....V.G.SWNS.SIG.
hSG16.45 vH6   ....................R...A............V......K....V.G.........
Kabat CDRs                                     *****           ***********
IMGT CDRs                                  ++++++++          ++++++++

60        70        80        90       101       110
               |....|....|....|....|.......|....|....|....|...|....|...
Rat SG16.45 vH LDSVKGRFTISRDNAKSTLYLQMNSLRSEDTATYYCTSPGLYFDYWGQGVMVTVSS
Hu HV3-9/HJ3   A...............NS........A....L...AK-------....T......
hSG16.45 vH6   A...............NS........A....L................T......
Kabat CDRs     ******                                *******
IMGT CDRs                                         ++++++++++
```

Figure 17: Alignment of hSG16.45 Heavy Chain Variants.

```
                    10        20        30        40        50
              ....|....|....|....|....|....|....|....|....|....|....
hSG16.45 vH1  EVQLLESGGGLVQPGGSLRLSCAASGFTFNDHWMTWIRQAPGKGLEWISSITNTGGATYY
hSG16.45 vH2  ............................................A...........
hSG16.45 vH3  ............................................A...........
hSG16.45 vH4  ..........................................V.............
hSG16.45 vH5  ....V.....................................V.........V.V.
hSG16.45 vH6  ....V.........R...........................V.........V.G.
Kabat CDRs                                      *****           ***********
IMGT CDRs                                ++++++++            ++++++++

60        70        80        90       101       110
              |....|....|....|....|.........|....|....|....|...|....|...
hSG16.45 vH1  LDSVKGRFTISRDNSKNTLYLQMNSLRAEDTAVYYCTSPGLYFDYWGQGVMVTVSS
hSG16.45 vH2  A.......................................................
hSG16.45 vH3  A..............S........................................
hSG16.45 vH4  A..............S.................................T.....
hSG16.45 vH5  A............A...................................T.....
hSG16.45 vH6  A............A..S..................L.............T.....
Kabat CDRs    ******                                    *******
IMGT CDRs                                     +++++++++
```

Fig. 18: Alignment of hSG16.45 Light Chain Variants with Human KV Acceptor Sequence; KV3-20/KJ2.

```
                          10        20        30        40        50
60
                    ....|....|....|....|....|....|....|....|....|....|....|
Rat SG16.45 vK      ........T.TAA....KV.IT.L.TS...VM.--....H.S.AS.K....ST..L.S.V.
Hu KV3-20/KJ2       EIVLTQSPGTLSLSPGERATLSCRASQSVSSSYLAWYQQKPGQAPRLLIYGASSRATGIP
hSG16.45 vK1        .............A.....V.I.....S...VM.--....H...........ST..L.S.V.
hSG16.45 vK2        ...................S...VM.--...........ST..L.S...
hSG16.45 vK3        ..................I.....S...VM.--....H...........ST..L.S.V.
hSG16.45 vK5        ....................L.TS...VM.--....H...........ST..L.S...
Kabat CDRs                                ***********           *******
IMGT CDRs                              +++++++              +++

70        80        90       100
                    ....|....|....|....|....|....|....|....|....
Rat SG16.45 vK      ..........SYS...NTM.A..A.T...HQWSSDPPT...S........
Hu KV3-20/KJ2       DRFSGSGSGTDFTLTISRLEPEDFAVYYC---------FGQGTKLEIKR
hSG16.45 vK1        ............Y......M..........HQWSSDPPT..........
hSG16.45 vK2        ...............................HQWSSDPPT..........
hSG16.45 vK3        ............Y..................HQWSSDPPT..........
hSG16.45 vK5        ............Y..................HQWSSDPPT..........
Kabat CDRs                                    *********
IMGT CDRs                                     +++++++++
```

Fig. 19: Alignment of hSG16.45 Light Chain Variants.

```
                     10        20        30        40        50        60
                ....|....|....|....|....|....|....|....|....|....|....|....|
hSG16.45 vK1    EIVLTQSPGTLSASPGERVTISCRASSSVSVMYWYQHKPGQAPRLLIYSTSSLASGVPDR
hSG16.45 vK2    .............L.....A.L................Q....................I...
hSG16.45 vK3    .............L.....A............................................
hSG16.45 vK5    .............L.....A.L..L.T.................................I...
Kabat CDRs                             **********              *******
IMGT CDRs                                 +++++++              +++

70        80        90       100
                ....|....|....|....|....|....|....|....|....|..
hSG16.45 vK1    FSGSGSGTDYTLTISRMEPEDFAVYYCHQWSSDPPTFGQGTKLEIKR
hSG16.45 vK2    .........F......L..............................
hSG16.45 vK3    ................L..............................
hSG16.45 vK5    ................L..............................
Kabat CDRs                                  *********
IMGT CDRs                                   +++++++++
```

In Vivo Activity of Multi Dosed hSG16.17-SEA in MM1S Disseminated Tumor Model in SCID Mice.

In Vivo Activity of Single Dosed hSG16.17-SEA in EJM Disseminated Tumor Model in NSG Mice.

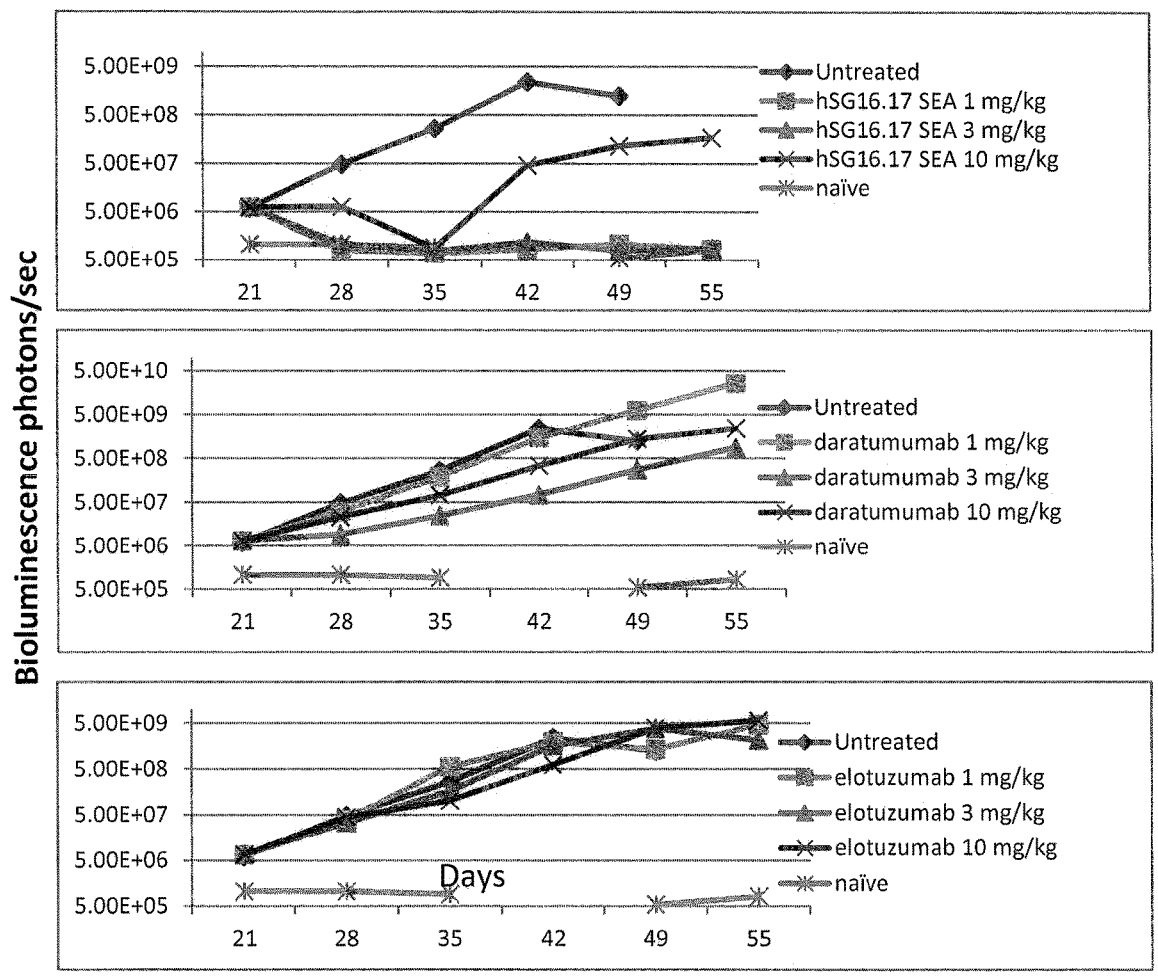
Fig. 22. In Vivo Activity of Multi Dosed hSG16.17-SEA in NCI-H929-luciferase Disseminated Tumor Model in NSG Mice.

In Vivo Activity of Single Dosed hSG16.17-SEA in NCI-H929-luciferase Disseminated Tumor Model in NSG Mice.

Fig. 24. In Vivo Activity of Single Dosed hSG16.17-SEA in MOLP-8-luciferase Disseminated Tumor Model in SCID Mice.
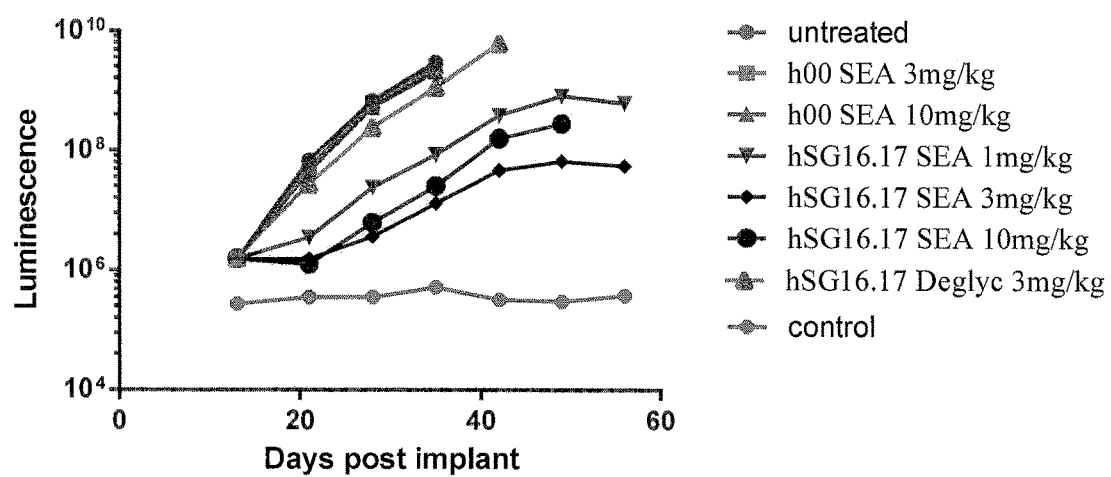

Fig. 25. The SG16.17 SEA Antibody Displays Improved ADCC Activity on MM1R Target Cells.
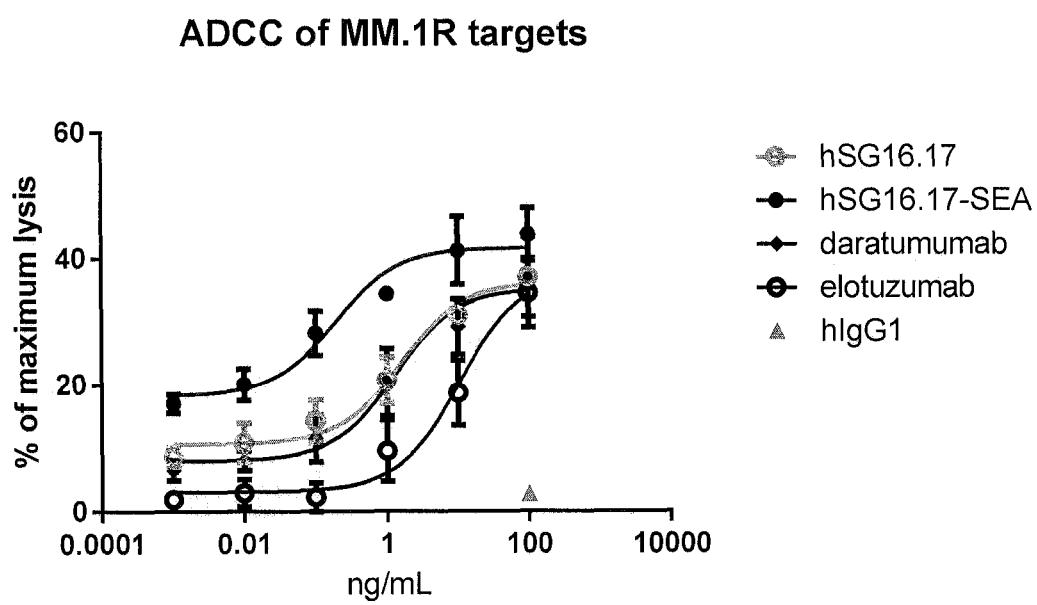

BCMA ANTIBODIES AND USE OF SAME TO TREAT CANCER AND IMMUNOLOGICAL DISORDERS

CROSS REFERENCE TO RELATED APPLICATION

This application is a continuation of U.S. application Ser. No. 15/434,921 filed Feb. 16, 2017, which claims the benefit of U.S. provisional application No. U.S. 62/296,594 filed Feb. 17, 2016, and U.S. provisional application No. 62/396,084 filed Sep. 16, 2016, all of which are incorporated herein by reference in their entirety for all purposes.

REFERENCE TO A SEQUENCE LISTING

This application includes an electronic sequence listing in a file named 0269_Sequence_Listing.txt created on May 9, 2019 and containing 73 KB, which is hereby incorporated by reference.

BACKGROUND

B-cell maturation antigen (BCMA, CD269) is a member of the TNF receptor superfamily. Expression of BCMA is restricted to the B-cell lineage where it is predominantly expressed in the interfollicular region of germinal centers and on differentiated plasma cells and plasma blasts. BCMA binds to two distinct ligands, a proliferation inducing ligand (APRIL) and B-cell activating factor (BAFF, also known as BlyS, TALL-1, and THANK). The ligands for BCMA bind two additional TNF receptors, transmembrane activator and calcium modulator and cyclophilin ligand interactor (TACI) and BAFF receptor (BAFF-R also called BR3). TACI binds APRIL and BAFF, whereas BAFF-R shows restricted but high-affinity binding to BAFF. Together, BCMA, TACI, BAFF-R, and their corresponding ligands regulate different aspects of humoral immunity, B-cell development, and homeostasis.

BCMA is virtually absent on naïve and memory B cells (Novak et al., Blood 103, 689-94 (2004)) but it is selectively induced during plasma cell differentiation where it may support humoral immunity by promoting the survival of normal plasma cells and plasma blasts (O'Conner et al., J. Exp Med. 199, 91-98 (2004)). BCMA has been reported to be expressed in primary multiple myeloma (MM) samples. BCMA has also been detected on the Reed-Sternberg cells (CD30$^+$) from patients with Hodgkin's disease. It has been reported based on knockdown experiments that that BCMA contributed to both proliferation and survival of a Hodgkin's disease cell line (Chiu et al., Blood 109, 729-39 (2007)).

SUMMARY OF THE CLAIMED INVENTION

The invention provides a humanized, chimeric or veneered antibody, which is a humanized or chimeric form of an antibody deposited as ATCC PTC-6937. Optionally the antibody comprises a mature heavy chain variable region having at least 90% sequence identity to hSG16.17 VH3 (SEQ ID NO: 13) and a mature light chain variable region having at least 90% sequence identity to hSG16.17 VK2 (SEQ ID NO: 19). Optionally, the antibody comprises a mature heavy chain variable region having at least 95% sequence identity to hSG16.17 VH3 (SEQ ID NO: 13) and a mature light chain variable region having at least 95% sequence identity to hSG16.17 VK2 (SEQ ID NO: 19). Optionally, the antibody comprising the three Kabat CDRs (SEQ ID NOs: 60-62) of hSG16.17 VH3 (SEQ ID NO: 13) and three Kabat CDRs (SEQ ID NOs: 90-92) of hSG16.17 VK2 (SEQ ID NO: 19) provided that position H58 can be occupied by N or K, position H60 can be occupied by A or N, position H61 can be occupied by Q or E, position H62 can be occupied by K or N, position H64 can be occupied by Q or K, position H65 can be occupied by G or T, position L24 can be occupied by R or L and position L53 can be occupied by S or R. Optionally, the antibody comprises the three Kabat CDRs (SEQ ID NOs: 60-62) of hSG16.17 VH3 (SEQ ID NO: 13) and three Kabat CDRs (SEQ ID NOs: 90-92) of hSG16.17 VK2 (SEQ ID NO: 19). Optionally, positions H58, H60, H61, H62, H64 and H65 are occupied by N, A, Q K, Q and G respectively and L24 and L53 are occupied by R and S respectively. Optionally, positions H20, H48, H69, H71, H73, H76, H80, H88, H91 and H93 are occupied by L, I, M, A, K, N, V, A, F, and T respectively, and positions L46, L48 and L87 are occupied by V, V and F respectively. Optionally, the mature heavy chain variable has the sequence of hSG16.17 VH3 (SEQ ID NO: 13) and the mature light chain variable region has the sequence of hSG16.17 VK2 (SEQ ID NO: 19).

The invention further provides a humanized, chimeric or veneered antibody, which is a humanized, chimeric or veneered form of the rat SG16.45 antibody having the VH (SEQ ID NO: 23) and VK (SEQ ID NO: 33) sequences. Optionally, the antibody comprises a heavy chain mature variable region having at least 90% sequence identity to hSG16.45 VH5 (SEQ ID NO: 31) and a mature light chain variable region having at least 90% sequence identity to hSG16.45 VK2 (SEQ ID NO: 36). Optionally, the antibody comprises a mature heavy chain variable region having at least 95% sequence identity to hSG16.45 VH5 (SEQ ID NO: 31) and a mature light chain variable region having at least 95% sequence identity to hSG16.45 VK2 (SEQ ID NO: 36). Optionally, the comprises the three Kabat CDRs (SEQ ID NOs: 152-154) of hSG16.45 VH5 (SEQ ID NO: 31) and three Kabat CDRs (SEQ ID NOs: 179-181) of hSG16.45 VK2 (SEQ ID NO: 36) provided that positions H50 can be occupied by A or S and position L24 can be occupied by R or L and position L26 can be occupied by S or T. Optionally, the antibody comprises the three Kabat CDRs (SEQ ID NOs: 152-154) of hSG16.45 VH5 (SEQ ID NO: 31) and three Kabat CDRs (SEQ ID NOs: 179-181) of hSG16.45 VK2 (SEQ ID NO: 36). Optionally positions H30, H93 and H94 are occupied by N, T and S respectively. Optionally, the mature heavy chain variable region has the sequence of hSG16.45 VH5 (SEQ ID NO: 31) and the mature light chain variable region has the sequence of hSG16.45 VK2 (SEQ ID NO: 36) or the mature heavy chain variable region has the sequence of hSG16.45 VH1 (SEQ ID NO: 27) and the mature light chain variable region has the sequence of hSG16.45 VK1 (SEQ ID NO: 35) or the mature heavy chain variable region has the sequence of hSG16.45 VH1 (SEQ ID NO: 27) and the mature light chain variable region has the sequence of hSG16.45 VK3 (SEQ ID NO: 37).

In any of the above antibodies, the mature heavy chain variable region can be fused to a heavy chain constant region and the mature light chain variable region can be fused to a light chain constant region. Optionally, the heavy chain constant region is a mutant form of natural human constant region which has reduced binding to an Fcγ receptor relative to the natural human constant region. Optionally, the heavy chain constant region is of IgG1 isotype. Optionally, the heavy chain constant region has an amino acid sequence comprising SEQ ID NO: 5 and the light chain constant region has an amino acid sequence comprising SEQ ID NO:

3. Optionally, the heavy chain constant region has an amino acid sequence comprising SEQ ID NO:7 (S239C) and the light chain constant region has an amino acid sequence comprising SEQ ID NO:3. Optionally, the antibody is a naked antibody. Optionally, the antibody is conjugated to a cytotoxic or cytostatic agent. Optionally, the antibody is conjugated to a cytotoxic agent. Optionally, the cytotoxic agent is conjugated to the via an enzyme cleavable linker. Optionally, the cytotoxic agent is a DNA minor groove binder, e.g., the cytotoxic agent having the formula

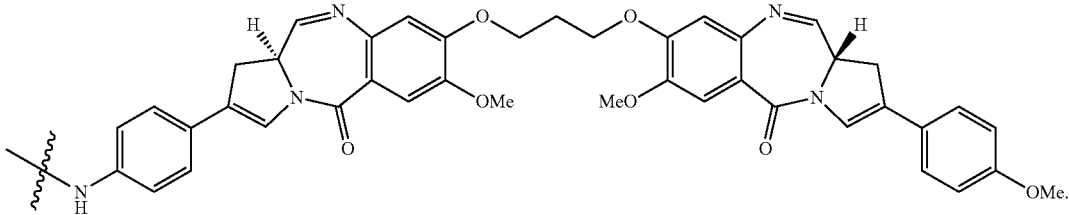 [SMILES: *Nc1ccc(C2=CN3C(=O)c4cc(OC)c(OCCCOc5cc6c(cc5OC)C(=O)N5C=C(c7ccc(OC)cc7)C[C@H]5C=N6)cc4N=C[C@@H]3C2)cc1]

Optionally, the cytotoxic agent is MMAE or MMAF.

The invention further provides pharmaceutical compositions comprising any of the antibodies described above and a pharmaceutically acceptable carrier.

In one embodiment, the invention provides an antibody comprising the three Kabat CDRs (SEQ ID NOs: 60-62) of hSG16.17 VH3 (SEQ ID NO: 13) and three Kabat CDRs (SEQ ID NOs: 90-92) of hSG16.17 VK2 (SEQ ID NO: 19). In a further embodiment, the invention provides an antibody having a mature heavy chain variable with the sequence of hSG16.17 VH3 (SEQ ID NO: 13) and a mature light chain variable region with the sequence of hSG16.17 VK2 (SEQ ID NO: 19). In another embodiment, the mature heavy chain variable region is fused to a heavy chain constant region and the mature light chain variable region is fused to a light chain constant region. The antibody can be, e.g., an IgG1 antibody. In another embodiment, the antibody lacks core fucosylation by fucose or a fucose analogue. The antibodies can by formulated into a pharmaceutical composition, e.g., with addition of a pharmaceutically acceptable carrier.

In a further embodiment, the pharmaceutical composition has a plurality of antibodies having a mature heavy chain variable with the sequence of hSG16.17 VH3 (SEQ ID NO: 13) and a mature light chain variable region with the sequence of hSG16.17 VK2 (SEQ ID NO: 19). The variable regions of these antibodies are preferably fused to appropriate heavy and light chain constant regions. In another embodiment the antibodies are IgG1 antibodies. In a further embodiment, the plurality of antibodies has less than about 5% of the antibodies have core fucosylation by fucose or a fucose analogue. In a further embodiment, the plurality of antibodies has less than about 10% of the antibodies have core fucosylation by fucose or a fucose analogue. In another embodiment, the plurality of antibodies includes about 2% antibodies with core fucosylation by fucose or a fucose analogue. In another embodiment, the plurality of antibodies includes 2% antibodies with core fucosylation by fucose or a fucose analogue.

The invention further provides a method of treating a patient having or at risk of having a cancer that expresses BCMA comprising administering to the patient an effective regime of an antibody as described above. Optionally, the cancer is a hematological cancer. Optionally, the hematological cancer is a myeloma, leukemia or a lymphoma. Optionally, the hematological cancer is multiple myeloma. Optionally the hematological cancer is non-Hodgkin's lymphoma (NHL) or Hodgkin's lymphoma. Optionally, the hematological cancer is myelodysplastic syndromes (MDS), myeloproliferative syndromes (MPS), Waldenström's macroglobulinemia or Burkett's lymphoma.

The invention further provides a method of treating a patient having or at risk of having an immune disorder mediated by immune cells expressing BCMA comprising administering to the patient an effective regime of any of the above described antibodies. Optionally, the disorder is a B cell mediated disorder. Optionally, the immune disorder is rheumatoid arthritis, systemic lupus E (SLE), Type I diabetes, asthma, atopic dermitus, allergic rhinitis, thrombocytopenic purpura, multiple sclerosis, psoriasis, Sjorgren's syndrome, Hashimoto's thyroiditis, Grave's disease, primary biliary cirrhosis, Wegener's granulomatosis, tuberculosis, and graft versus host disease.

BRIEF DESCRIPTION OF THE FIGURES

FIG. 7 shows alignment of hSG16.17 heavy chain variants with human VH acceptorsequence, HV1-2/HJ3. It shows rat SG16.17 vH (SEQ ID NO: 8) with Kabat CDRs (SEQ ID Nos: 39-41) and IMGT CDRs (SEQ ID NOs: 42 and 43); Hu HV1-2/HJ3 (SEQ ID NO: 9) with Kabat CDRs (SEQ ID NOs: 44 and 45) and IMGT CDRs (SEQ ID NO: 46 and "AR"); hSG16.17 vH1 (SEQ ID NO: 11) with Kabat CDRs (SEQ ID NOs: 50-52) and IMGT CDRs (SEQ ID NOs: 53 and 54); hSG16.17 vH2 (SEQ ID NO: 12) with Kabat CDRs (SEQ ID NOs: 55-57) and IMGT CDRs (SEQ ID NOs: 58 and 59); hSG16.17 vH3 (SEQ ID NO: 13) with Kabat CDRs (SEQ ID NOs: 60-62) and IMGT CDRs (SEQ ID NOs: 63 and 64); and hSG16.17 vH4 (SEQ ID NO: 14) with Kabat CDRs (SEQ ID NOs: 65-67) and IMGT CDRs (SEQ ID NOs: 68 and 69).

FIG. 8 shows alignment of hSG16.17 heavy chain variants with human VH acceptor sequence; HV1-46/HJ3. It shows the sequences of rat SG16.17 vH (SEQ ID NO: 8) with Kabat CDRs (SEQ ID NOs: 39-41) and IMGT CDRs (SEQ ID NOs: 42 and 43); Hu HV1-46/HJ3 (SEQ ID NO: 10) with Kabat CDRs (SEQ ID NOs: 47 and 48) and IMGT CDRs (SEQ ID NO: 49 and "AR"); hSG16.17 vH5 (SEQ ID NO: 15) with Kabat CDRs (SEQ ID NOs: 70-72) and IMGT CDRs (SEQ ID NOs: 73 and 74); and hSG16.17 vH6 (SEQ ID NO: 16) with Kabat CDRs (SEQ ID NOs: 75-77) and IMGT CDRs (SEQ ID NOs: 78 and 79).

FIG. 9 shows alignment of hSG16.17 heavy chain variants. It shows the sequences of hSG16.17 vH1-6 (SEQ ID NOs: 11-16).

FIG. 10 shows alignment of hSG16.17 light chain variants with human VK acceptor sequence; KV1-12/KJ5. It shows the sequences of rat SG16.17 vK (SEQ ID NO: 17) with Kabat CDRs (SEQ ID NOs: 80-82) and IMGT CDRs (SEQ ID NO: 83, "TTS", and SEQ ID NO: 84, respectively); Hu KV1-12/KJ5 (SEQ ID NO: 18) with Kabat CDRs (SEQ ID NOs: 85-87) and IMGT CDRs (SEQ ID NO: 88, "AAS", and SEQ ID NO: 89, respectively); hSG16.17 vK2 (SEQ ID NO: 19) with Kabat CDRs (SEQ ID NOs: 90-92) and IMGT CDRs (SEQ ID NO: 93, "TTS", and SEQ ID NO: 94, respectively); hSG16.17 vK3 (SEQ ID NO: 20) with Kabat CDRs (SEQ ID NOs: 95-97) and IMGT CDRs (SEQ ID NO: 98, "TTS", and SEQ ID NO: 99, respectively); hSG16.17 vK4 (SEQ ID NO: 21) with Kabat CDRs (SEQ ID NOs. 100-102) and IMGT CDRs (SEQ ID NO: 103, "TTS", and SEQ ID NO: 104, respectively); and hSG16.17 vK5(SEQ ID NO: 22) with Kabat CDRs (SEQ ID NOs: 105-107) and IMGT CDRs (SEQ ID NO: 108, "TTS", and SEQ ID NO: 109, respectively).

FIG. 11 shows alignment of hSG16.17 light chain variants. It shows the sequences of hSG16.17 vK2, vK3, vK4, vK5 (SEQ ID NOs: 19-22).

FIG. 13: shows chimeric SG16.17 induces signallying through FcγRIIIA.

FIG. 14 shows alignment of hSG16.45 heavy chain variants with human HV acceptor sequence HV3-23/HJ3. It shows the sequences of Rat SG16.45 vH (SEQ ID NO: 23) with Kabat CDRs (SEQ ID NOs: 110-112) and IMGT CDRs (SEQ ID NOs: 113-115); Hu HV3-23/HJ3 (SEQ ID NO: 24) with Kabat CDRs (SEQ ID NOs: 116 and 117) and IMGT CDRs (SEQ ID NOs: 118 and 119, and "AK", respectively); hSG16.45 vH1 (SEQ ID NO: 27) with Kabat CDRs (SEQ ID NOs: 128-130) and IMGT CDRs (SEQ ID NOs: 131-133); hSG16.45 vH2 (SEQ ID NO: 28) with Kabat CDRs (SEQ ID NOs: 134-136) and IMGT CDRs (SEQ ID NOs: 137-139); hSG16.45 vH3 (SEQ ID NO: 29) with Kabat CDRs (SEQ ID NOs: 140-142) and IMGT CDRs (SEQ ID NOs: 143-145); and hSG16.45 vH4 (SEQ ID NO: 30) with Kabat CDRs (SEQ ID NOs: 146-148) and IMGT CDRs (SEQ ID NOs: 149-151).

FIG. 15 shows alignment of hSG16.45 heavy chain variants with human HV acceptor sequence HV3-74/HJ3. It shows the sequences of Rat SG16.45 vH (SEQ ID NO: 23) with Kabat CDRs (SEQ ID NOs: 110-112) and IMGT CDRs (SEQ ID NOs: 113-115); Hu HV3-74/HJ3 (SEQ ID NO: 25) with Kabat CDRs (SEQ ID NOs: 120 and 121) and IMGT CDRs (SEQ ID NOs: 122 and 123, and "AR", respectively); hSG16.45 vH5 (SEQ ID NO: 31) with Kabat CDRs (SEQ ID NOs: 152-154) and IMGT CDRs (SEQ ID NOs: 155-157).

FIG. 16 shows alignment of hSG16.45 heavy chain variants with human HV acceptor sequence HV3-9/HJ3. It shows the sequences of Rat SG16.45 vH (SEQ ID NO: 23) with Kabat CDRs (SEQ ID NOs: 110-112) and IMGT CDRs (SEQ ID NOs: 113-115); Hu HV3-9/HJ3 (SEQ ID NO: 26) with Kabat CDRs (SEQ ID NOs: 124 and 125) and IMGT CDRs (SEQ ID NOs: 126 and 127, and "AR", respectively); hSG16.45 vH6 (SEQ ID NO: 32) with Kabat CDRs (SEQ ID NOs: 158-160) and IMGT CDRs (SEQ ID NOs: 161-163).

FIG. 17 shows alignment of hSG16.45 heavy chain variants. It shows the sequences of hSG16.45 vH1-6 (SEQ ID NOs: 27-32).

FIG. 18 shows alignment of hSG16.45 light chain variants with human KV acceptor sequence KV3-20/KJ2. It shows the sequences of Rat SG16.45 vK (SEQ ID NO: 33) with Kabat CDRs (SEQ ID NOs: 164-166) and IMGT CDRs (SEQ ID NO: 167, "STS", and SEQ ID NO: 168, respectively); Hu KV3-20/KJ2 (SEQ ID NO: 34) with Kabat CDRs (SEQ ID NOs: 169-171) and IMGT CDRs (SEQ ID NO: 172, "STS", and SEQ ID NO: 173, respectively); hSG16.45 vK1 (SEQ ID NO: 35) with Kabat CDRs (SEQ ID NOs: 174-176) and IMGT CDRs (SEQ ID NO: 177, "STS", and SEQ ID NO: 178, respectively); hSG16.45 vK2 (SEQ ID NO: 36) with Kabat CDRs (SEQ ID NOs: 179-181) and IMGT CDRs (SEQ ID NO: 182, "STS", and SEQ ID NO: 183, respectively); hSG16.45 vK3 (SEQ ID NO: 37) with Kabat CDRs (SEQ ID NOs: 184-186) and IMGT CDRs (SEQ ID NO: 187, "STS", and SEQ ID NO: 188, respectively); and hSG16.45 vK5 (SEQ ID NO: 38) with Kabat CDRs (SEQ ID NOs: 189-191) and IMGT CDRs (SEQ ID NO: 192, "STS", and SEQ ID NO: 193, respectively).

FIG. 19. shows alignment of hSG16.45 light chain variants. It shows the sequences of hSG16.45 vK1, vK2, vK3, vK5 (SEQ ID NOs: 35-38).

FIG. 22 show in vivo activity of multi dosed hSG16.17-SEA in NCI-H929-luciferase disseminated tumor model in NSG mice.

FIG. 24 provides in vivo activity of single dosed hSG16.17-SEA in MOLP-8-luciferase disseminated tumor model in SCID mice.

FIG. 25 provides ADCC activity of the SG16.17 SEA antibody on MM1R target cells.

DEFINITIONS

Figure 1A:
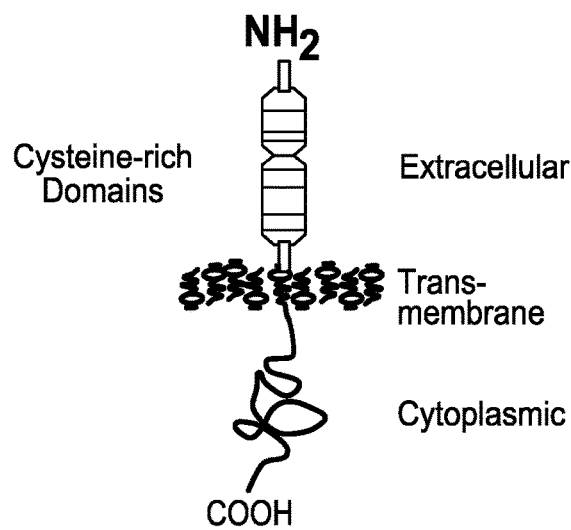
FIG. 1A shows the structure of BCMA.

An "isolated" antibody refers to an antibody that has been identified and separated and/or recovered from components of its natural environment and/or an antibody that is recombinantly produced. A "purified antibody" is an antibody that is typically at least 50% w/w pure of interfering proteins and other contaminants arising from its production or purification but does not exclude the possibility that the monoclonal antibody is combined with an excess of pharmaceutical acceptable carrier(s) or other vehicle intended to facilitate its use. Interfering proteins and other contaminants can include, for example, cellular components of the cells from which an antibody is isolated or recombinantly produced. Sometimes monoclonal antibodies are at least 60%, 70%, 80%, 90%, 95 or 99% w/w pure of interfering proteins and contaminants from production or purification. The antibodies described herein, including rat, chimeric, veneered and humanized antibodies can be provided in isolated and/or purified form.

A "monoclonal antibody" refers to an antibody obtained from a population of substantially homogeneous antibodies, i.e., the individual antibodies comprising the population are identical except for possible naturally occurring mutations that may be present in minor amounts. The modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by the hybridoma method first described by Kohler et al. (1975) Nature 256:495, or may be made by recombinant DNA methods (see, for example, U.S. Pat. No. 4,816,567). The "monoclonal antibodies" may also be isolated from phage antibody libraries using the techniques described in Clackson et al. (1991) Nature, 352:624-628 and Marks et al. (1991) J. Mol. Biol., 222:581-597, for example or may be made by other methods. The antibodies described herein are monoclonal antibodies.

Specific binding of a monoclonal antibody to its target antigen means an affinity of at least $10^6$, $10^7$, $10^8$, $10^9$, or $10^{10}$ $M^{-1}$. Specific binding is detectably higher in magnitude and distinguishable from non-specific binding occurring to at least one unrelated target. Specific binding can be the result of formation of bonds between particular functional groups or particular spatial fit (e.g., lock and key type) whereas nonspecific binding is usually the result of van der Waals forces.

The basic antibody structural unit is a tetramer of subunits. Each tetramer includes two identical pairs of polypeptide chains, each pair having one "light" (about 25 kDa) and one "heavy" chain (about 50-70 kDa). The amino-terminal portion of each chain includes a variable region of about 100 to 110 or more amino acids primarily responsible for antigen recognition. This variable region is initially expressed linked to a cleavable signal peptide. The variable region without the signal peptide is sometimes referred to as a mature variable region. Thus, for example, a light chain mature variable region, means a light chain variable region without the light chain signal peptide. The carboxy-terminal portion of each chain defines a constant region primarily responsible for effector function.

Light chains are classified as either kappa or lambda. Heavy chains are classified as gamma, mu, alpha, delta, or epsilon, and define the antibody's isotype as IgG, IgM, IgA, IgD and IgE, respectively. Within light and heavy chains, the variable and constant regions are joined by a "J" region of about 12 or more amino acids, with the heavy chain also including a "D" region of about 10 or more amino acids. (See generally, *Fundamental Immunology* (Paul, W., ed., 2nd ed. Raven Press, N.Y., 1989, Ch. 7, incorporated by reference in its entirety for all purposes).

The mature variable regions of each light/heavy chain pair form the antibody binding site. Thus, an intact antibody has two binding sites. Except in bifunctional or bispecific antibodies, the two binding sites are the same. The chains all exhibit the same general structure of relatively conserved framework regions (FR) joined by three hypervariable regions, also called complementarity determining regions or CDRs. The CDRs from the two chains of each pair are aligned by the framework regions, enabling binding to a specific epitope. From N-terminal to C-terminal, both light and heavy chains comprise the domains FR1, CDR1, FR2, CDR2, FR3, CDR3 and FR4. The assignment of amino acids to each domain is in accordance with the definitions of Kabat, *Sequences of Proteins of Immunological Interest* (National Institutes of Health, Bethesda, Md., 1987 and 1991), or Chothia & Lesk, *J. Mol. Biol.* 196:901-917 (1987); Chothia et al., *Nature* 342:878-883 (1989), or a composite of Kabat and Chothia, or IMGT, AbM or Contact or other conventional definition of CDRs. Kabat also provides a widely used numbering convention (Kabat numbering) in which corresponding residues between different heavy chains or between different light chains are assigned the same number. Unless otherwise apparent from the context, Kabat numbering is used to designate the position of amino acids in the variable regions. Unless otherwise apparent from the context EU numbering is used to designated positions in constant regions.

The term "antibody" includes intact antibodies and binding fragments thereof. Typically, antibody fragments compete with the intact antibody from which they were derived for specific binding to the target including separate heavy chains, light chains Fab, Fab', F(ab')$_2$, F(ab)c, diabodies, Dabs, nanobodies, and Fv. Fragments can be produced by recombinant DNA techniques, or by enzymatic or chemical separation of intact immunoglobulins. The term "antibody" also includes a diabody (homodimeric Fv fragment) or a minibody ($V_L$-$V_H$-$C_H3$), a bispecific antibody or the like. A bispecific or bifunctional antibody is an artificial hybrid antibody having two different heavy/light chain pairs and two different binding sites (see, e.g., Songsivilai and Lachmann, Clin. Exp. Immunol., 79:315-321 (1990); Kostelny et al., J. Immunol., 148:1547-53 (1992)).

The term "antibody" includes an antibody by itself (naked antibody) or an antibody conjugated to a cytotoxic or cytostatic drug.

A chimeric antibody is an antibody in which the mature variable regions of light and heavy chains of a non-human antibody (e.g., a mouse) are combined with human light and heavy chain constant regions. Such antibodies substantially or entirely retain the binding specificity of the mouse antibody, and are about two-thirds human sequence.

A veneered antibody is a type of humanized antibody that retains some and usually all of the CDRs and some of the non-human variable region framework residues of a non-human antibody but replaces other variable region framework residues that may contribute to B- or T-cell epitopes, for example exposed residues (Padlan, Mol. Immunol. 28:489, 1991) with residues from the corresponding positions of a human antibody sequence. The result is an antibody in which the CDRs are entirely or substantially from a non-human antibody and the variable region frameworks of the non-human antibody are made more human-like by the substitutions.

The term "epitope" refers to a site on an antigen to which an antibody binds. An epitope can be formed from contiguous amino acids or noncontiguous amino acids juxtaposed by tertiary folding of one or more proteins. Epitopes formed from contiguous amino acids are typically retained on exposure to denaturing solvents whereas epitopes formed by tertiary folding are typically lost on treatment with denaturing solvents. An epitope typically includes at least 3, and more usually, at least 5 or 8-10 amino acids in a unique spatial conformation. Methods of determining spatial conformation of epitopes include, for example, x-ray crystallography and 2-dimensional nuclear magnetic resonance. See, e.g., Epitope Mapping Protocols, in Methods in Molecular Biology, Vol. 66, Glenn E. Morris, Ed. (1996).

Antibodies that recognize the same or overlapping epitopes can be identified in a simple immunoassay showing the ability of one antibody to compete with the binding of another antibody to a target antigen. The epitope of an antibody can also be defined by X-ray crystallography of the antibody bound to its antigen to identify contact residues. Alternatively, two antibodies have the same epitope if all amino acid mutations in the antigen that reduce or eliminate binding of one antibody reduce or eliminate binding of the other. Two antibodies have overlapping epitopes if some amino acid mutations that reduce or eliminate binding of one antibody reduce or eliminate binding of the other.

Competition between antibodies is determined by an assay in which an antibody under test inhibits specific binding of a reference antibody to a common antigen (see, e.g., Junghans et al., *Cancer Res.* 50:1495, 1990). A test antibody competes with a reference antibody if an excess of a test antibody (e.g., at least 2×, 5×, 10×, 20× or 100×) inhibits binding of the reference antibody by at least 50% but preferably 75%, 90% or 99% as measured in a competitive binding assay. Antibodies identified by competition assay (competing antibodies) include antibodies binding to the same epitope as the reference antibody and antibodies binding to an adjacent epitope sufficiently proximal to the epitope bound by the reference antibody for steric hindrance to occur. Antibodies that compete with the h2H12 antibody for binding to the human BCMA protein are included in this disclosure.

The term "patient" includes human and other mammalian subjects that receive either prophylactic or therapeutic treatment.

For purposes of classifying amino acids substitutions as conservative or nonconservative, amino acids are grouped as follows: Group I (hydrophobic side chains): met, ala, val, leu, ile; Group II (neutral hydrophilic side chains): cys, ser, thr; Group III (acidic side chains): asp, glu; Group IV (basic side chains): asn, gln, his, lys, arg; Group V (residues influencing chain orientation): gly, pro; and Group VI (aromatic side chains): trp, tyr, phe. Conservative substitutions involve substitutions between amino acids in the same class. Nonconservative substitutions constitute exchanging a member of one of these classes for a member of another.

Percentage sequence identities are determined with antibody sequences maximally aligned by the Kabat numbering convention. After alignment, if a subject antibody region (e.g., the entire mature variable region of a heavy or light chain) is being compared with the same region of a reference antibody, the percentage sequence identity between the subject and reference antibody regions is the number of positions occupied by the same amino acid in both the subject and reference antibody region divided by the total number of aligned positions of the two regions, with gaps not counted, multiplied by 100 to convert to percentage.

Compositions or methods "comprising" one or more recited elements may include other elements not specifically recited. For example, a composition that comprises antibody may contain the antibody alone or in combination with other ingredients.

Designation of a range of values includes all integers within or defining the range.

An antibody effector function refers to a function contributed by an Fc domain(s) of an Ig. Such functions can be, for example, antibody-dependent cellular cytotoxicity, antibody-dependent cellular phagocytosis or complement-dependent cytotoxicity. Such function can be effected by, for example, binding of an Fc effector domain(s) to an Fc receptor on an immune cell with phagocytic or lytic activity or by binding of an Fc effector domain(s) to components of the complement system. Typically, the effect(s) mediated by the Fc-binding cells or complement components result in inhibition and/or depletion of the BCMA targeted cell. Fc regions of antibodies can recruit Fc receptor (FcR)-expressing cells and juxtapose them with antibody-coated target cells. Cells expressing surface FcR for IgGs including FcγRIII (CD16), FcγRII (CD32) and FcγRIII (CD64) can act as effector cells for the destruction of IgG-coated cells. Such effector cells include monocytes, macrophages, natural killer (NK) cells, neutrophils and eosinophils. Engagement of FcγR by IgG activates antibody-dependent cellular cytotoxicity (ADCC) or antibody-dependent cellular phagocytosis (ADCP). ADCC is mediated by $CD16^+$ effector cells through the secretion of membrane pore-forming proteins and proteases, while phagocytosis is mediated by $CD32^+$ and $CD64^+$ effector cells (see *Fundamental Immunology*, 4th ed., Paul ed., Lippincott-Raven, N.Y., 1997, Chapters 3, 17 and 30; Uchida et al., 2004, *J. Exp. Med.* 199:1659-69; Akewanlop et al., 2001, *Cancer Res.* 61:4061-65; Watanabe et al., 1999, *Breast Cancer Res. Treat.* 53:199-207). In addition to ADCC and ADCP, Fc regions of cell-bound antibodies can also activate the complement classical pathway to elicit complement-dependent cytotoxicity (CDC). C1q of the complement system binds to the Fc regions of antibodies when they are complexed with antigens. Binding of C1q to cell-bound antibodies can initiate a cascade of events involving the proteolytic activation of C4 and C2 to generate the C3 convertase. Cleavage of C3 to C3b by C3 convertase enables the activation of terminal complement components including C5b, C6, C7, C8 and C9. Collectively, these proteins form membrane-attack complex pores on the antibody-coated cells. These pores disrupt the cell membrane integrity, killing the target cell (see *Immunobiology*, 6th ed., Janeway et al., Garland Science, N.Y., 2005, Chapter 2).

The term "antibody-dependent cellular cytotoxicity", or ADCC, is a mechanism for inducing cell death that depends upon the interaction of antibody-coated target cells with immune cells possessing lytic activity (also referred to as effector cells). Such effector cells include natural killer cells, monocytes/macrophages and neutrophils. The effector cells attach to an Fc effector domain(s) of Ig bound to target cells via their antigen-combining sites. Death of the antibody-coated target cell occurs as a result of effector cell activity.

The term "antibody-dependent cellular phagocytosis", or ADCP, refers to the process by which antibody-coated cells are internalized, either in whole or in part, by phagocytic immune cells (e.g., macrophages, neutrophils and dendritic cells) that bind to an Fc effector domain(s) of Ig.

The term "complement-dependent cytotoxicity", or CDC, refers to a mechanism for inducing cell death in which an Fc effector domain(s) of a target-bound antibody activates a series of enzymatic reactions culminating in the formation of holes in the target cell membrane. Typically, antigen-antibody complexes such as those on antibody-coated target cells bind and activate complement component C1q which in turn activates the complement cascade leading to target cell death. Activation of complement may also result in deposition of complement components on the target cell surface that facilitate ADCC by binding complement receptors (e.g., CR3) on leukocytes.

A "cytotoxic effect" refers to the depletion, elimination and/or the killing of a target cell. A "cytotoxic agent" refers to an agent that has a cytotoxic effect on a cell.

Cytotoxic agents can be conjugated to an antibody or administered in combination with an antibody.

A "cytostatic effect" refers to the inhibition of cell proliferation. A "cytostatic agent" refers to an agent that has a cytostatic effect on a cell, thereby inhibiting the growth and/or expansion of a specific subset of cells. Cytostatic agents can be conjugated to an antibody or administered in combination with an antibody.

The term "pharmaceutically acceptable" means approved or approvable by a regulatory agency of the Federal or a state government or listed in the U.S. Pharmacopeia or other generally recognized pharmacopeia for use in animals, and more particularly in humans. The term "pharmaceutically compatible ingredient" refers to a pharmaceutically acceptable diluent, adjuvant, excipient, or vehicle with which an anti-BCMA antibody is administered to a subject.

The phrase "pharmaceutically acceptable salt," refers to pharmaceutically acceptable organic or inorganic salts of an anti-BCMA-1 antibody or conjugate thereof or agent administered with an anti-BCMA-1 antibody. Exemplary salts include sulfate, citrate, acetate, oxalate, chloride, bromide, iodide, nitrate, bisulfate, phosphate, acid phosphate, isonicotinate, lactate, salicylate, acid citrate, tartrate, oleate, tannate, pantothenate, bitartrate, ascorbate, succinate, maleate, gentisinate, fumarate, gluconate, glucuronate, saccharate, formate, benzoate, glutamate, methanesulfonate, ethanesulfonate, benzenesulfonate, p toluenesulfonate, and pamoate (i.e., 1,1' methylene bis-(2 hydroxy 3 naphthoate)) salts. A pharmaceutically acceptable salt may involve the inclusion of another molecule such as an acetate ion, a succinate ion or other counterion. The counterion may be any organic or inorganic moiety that stabilizes the charge on the parent compound. Furthermore, a pharmaceutically acceptable salt may have more than one charged atom in its structure. Instances where multiple charged atoms are part of the pharmaceutically acceptable salt can have multiple counter ions. Hence, a pharmaceutically acceptable salt can have one or more charged atoms and/or one or more counterion.

Unless otherwise apparent from the context, the term "about" encompasses insubstantial variation having no significant effect on functional properties (e.g., within a margin of error or experimental measurement).

DETAILED DESCRIPTION

I. General

The invention provides monoclonal antibodies that specifically bind to BCMA. The antibodies are useful for treatment and diagnoses of various cancers and immunological disorders as well as detecting BCMA.

II. Target Molecules

Unless otherwise indicated, BCMA means a human BCMA. Exemplary human nucleic acid and amino acid sequences are provided by SEQ ID NOS:1 and 2. Unless otherwise apparent from the context reference to BMCA means at least an extracellular domain of the protein (approximately residues 1-54 of SEQ ID NO: 2) and sometimes the complete protein. Likewise, unless otherwise apparent from the context reference to BAFF and APRIL and their receptors other than BCMA refers to wild type human sequences e.g., as provided in the Swiss Prot Database.

III. Antibodies of the Invention

A. Binding Specificity and Functional Properties

The SG16.17 antibody is a rat monoclonal antibody that specifically binds to human BCMA as described in the examples. An ATCC deposit was made on Aug. 15, 2005 under the Budapest Treaty. The ATCC is located at 10801 University Boulevard, Manassas, Va. 20110-2209, USA. The ATCC deposit was assigned accession number of PTA-6937. The SG16.17 antibody inhibits binding of BCMA to both of its ligands, APRIL and BAFF. The SG16.17 antibody when linked to a human IgG1 elicits ADCC, binds to and elicits signaling through Fcγ receptors. The SG16.17 antibody can also be incorporated into an antibody drug conjugate to deliver a linked drug into the interior of cells expressing BCMA. The SG16.45 antibody is another rat monoclonal antibody that specifically binds to human BCMA, inhibits its binding to its ligands and can deliver a linked drug to the interior of cells expressing BCMA.

The invention provides humanized, chimeric and veneered forms of the SG16.17 antibody (designated hSG16.17, cSG16.17 or vSG16.17) and SG16.45 (analogously designated). Such antibodies typically retain some or all of the properties for SG16.17 or SG16.45 noted above. For any given property, humanized, chimeric or veneered antibodies may exhibit the property to the same extent within experimental error or more or less than rat SG16.17 or SG16.45. The affinity of humanized, chimeric or veneered forms of the rat SG16.17 antibody (i.e., Ka) can be greater than that of the rat SG16.17 antibody, or within a factor of five or a factor of two (i.e., more than or less than) than that of the rat SG16.17 antibody for human BCMA. Preferred humanized, chimeric or veneered SG16.17 antibodies bind to the same epitope and/or compete with rat SG16.17 antibodies for binding to human BCMA. The affinity of humanized, chimeric or veneered forms of the rat SG16.45 antibody (i.e., Ka) can be greater than that of the rat SG16.45 antibody, or within a factor of five or a factor of two (i.e., more than or less than) than that of the rat SG16.45 antibody for human BCMA. Preferred humanized, chimeric or veneered SG16.45 antibodies bind to the same epitope and/or compete with rat SG16.45 antibodies for binding to human BCMA.

Preferred humanized, chimeric and veneered antibodies inhibit cancer (e.g., growth of cells, metastasis and/or lethality to the organisms) or B-cell mediated immune disorders as shown in vitro, in an animal model or clinical trial.

B. Antibodies

A humanized antibody is a genetically engineered antibody in which CDRs from a non-human "donor" antibody are grafted into human "acceptor" antibody sequences (see, e.g., Queen, U.S. Pat. Nos. 5,530,101 and 5,585,089; Winter, U.S. Pat. No. 5,225,539; Carter, U.S. Pat. No. 6,407,213; Adair, U.S. Pat. No. 5,859,205; and Foote, U.S. Pat. No. 6,881,557). The acceptor antibody sequences can be, for example, a mature human antibody sequence, a composite of such sequences, a consensus sequence of human antibody sequences, or a germline region sequence. For humanization of SG16.17, a preferred acceptor sequence for the heavy chain is the germline $V_H$ exon $V_H$1-2 and for the J exon ($J_H$), exon $J_H$-3. For the light chain, a preferred acceptor sequence is exon $V_L$1-12 and J exon $J_K$5. For humanization of SG16.45, a preferred heavy chain acceptor sequence is HV3-23/HJ3 (SEQ ID NO: 24) and a preferred light chain acceptor sequence is KV3-20/KJ2 (SEQ ID NO: 34).

Thus, a humanized antibody is an antibody having at least four CDRs entirely or substantially from a non-human donor antibody and variable region framework sequences and constant regions, if present, entirely or substantially from human antibody sequences. Similarly a humanized heavy chain has at least two and usually all three CDRs entirely or substantially from a donor antibody heavy chain, and a heavy chain variable region framework sequence and heavy chain constant region, if present, substantially from human heavy chain variable region framework and constant region sequences. Similarly a humanized light chain has at least two and usually all three CDRs entirely or substantially from a donor antibody light chain, and a light chain variable region framework sequence and light chain constant region, if present, substantially from human light chain variable region framework and constant region sequences. Other than nanobodies and dAbs, a humanized antibody comprises a humanized heavy chain and a humanized light chain. A CDR in a humanized or human antibody is substantially from or substantially identical to a corresponding CDR in a non-human antibody when at least 60%, 85%, 90%, 95% or 100% of corresponding residues (as defined by Kabat) are identical between the respective CDRs. The variable region framework sequences of an antibody chain or the constant region of an antibody chain are substantially from a human variable region framework sequence or human constant region respectively when at least 70%, 80%, 85%, 90%, 95% or 100% of corresponding residues defined by Kabat are identical.

Although humanized antibodies often incorporate all six CDRs (preferably as defined by Kabat, but alternatively as defined by IMGT, Chothia, composite Kabat-Chothia, AbM or Contact or other conventional definition) from a mouse antibody, they can also be made with less than all CDRs (e.g., at least 4, or 5) CDRs from a mouse antibody (e.g., Pascalis et al., *J. Immunol.* 169:3076, 2002; Vajdos et al., *Journal of Molecular Biology*, 320: 415-428, 2002; Iwahashi et al., *Mol. Immunol.* 36:1079-1091, 1999; Tamura et al, *Journal of Immunology*, 164:1432-1441, 2000).

Certain amino acids from the human variable region framework residues can be selected for substitution based on their possible influence on CDR conformation and/or binding to antigen. Investigation of such possible influences is by modeling, examination of the characteristics of the amino acids at particular locations, or empirical observation of the effects of substitution or mutagenesis of particular amino acids.

For example, when an amino acid differs between a murine variable region framework residue and a selected human variable region framework residue, the human framework amino acid can be substituted by the equivalent framework amino acid from the mouse antibody when it is reasonably expected that the amino acid:

(1) noncovalently binds antigen directly,
(2) is adjacent to a CDR region,
(3) otherwise interacts with a CDR region (e.g. is within about 6 Å of a CDR region); or
(4) mediates interaction between the heavy and light chains.

The invention provides humanized forms of the rat SG16.17 antibody including six exemplified humanized heavy chain mature variable regions (hSG16.17 VH1-6) (SEQ ID Nos: 11-16) and four exemplified humanized light chain mature variable regions (hSG16.17 VK2-5) (SEQ ID NOs: 19-22). The heavy and light chains can be combined in any permutations, with permutations including any of hSG16.17 VH1, VH3 or VH5 being preferred. The permutation having the best combination of binding affinity, percentage sequence identity to human germline, expression and percentage of monomeric content was hSG16.17 VH3 VK2. This antibody shows similar affinity within experimental error as the rat SG16.17, greater than 85% sequence identity with human germline in both heavy and light chain variable regions (thus, qualifying for "humanized" designation under the new INN guidelines), high expression in CHO cells, and high proportion of monomers. Compared with most other humanized antibodies hSG16.17 VH3 VK2 is unusual in having a large number of variable region framework mutations in which human acceptor residues are changed to the corresponding rat residue (13) but also having a large number of "forward" CDR mutations, in which a rat residue in the Kabat CDRs is changed to the corresponding residue in the human acceptor sequence, such that overall the antibody has sufficient sequence identity to human germline sequences to be classified as humanized under INN guidelines. Most previous humanized antibodies have had Kabat CDR entirely from the donor antibody.

The invention provides antibodies in which the heavy chain variable region shows at least 90% identity to hSG16.17 VH3 (SEQ ID NO: 13) and a light chain variable region at least 90% identical to hSG16.17 VK2 (SEQ ID NO: 19). Some antibodies show at least 95%, 96%, 97%, 98% or 99% sequence identity to HV3 and at least 95%, 96%, 97%, 98% or 99% sequence identity to VK2. Some such antibodies include the three Kabat CDRs (SEQ ID NOs: 60-62) of hSG16.17 VH3 (SEQ ID NO: 13) and three Kabat CDRs (SEQ ID NOs: 90-92) of hSG16.17 VK2 (SEQ ID NO: 19). Some such antibodies include the three Kabat CDRs (SEQ ID NOs: 60-62) of hSG16.17 VH3 (SEQ ID NO: 13) and three Kabat CDRs (SEQ ID NOs: 90-92) of hSG16.17 VK2 (SEQ ID NO: 19) provided that position H58 can be occupied by N or K, position H60 can be occupied by A or N, position H61 can be occupied by Q or E, position H62 can be occupied by K or N, position H64 can be occupied by Q or K, position H65 can be occupied by G or T, position L24 can be occupied by R or L and position L53 can be occupied by S or R. Preferably positions H58, H60, H61, H62, H64 and H65 are occupied by N, A, Q, K, Q and G respectively and L24 and L53 are occupied by R and S respectively. These recited residues represent amino acids from a human acceptor sequence occupying positions within the Kabat CDRs. Some antibodies have at least 1, 2, 3, 4, 5, 6, 7 or 8 rat residues in the human Kabat CDRs replaced with corresponding residues from a human acceptor sequence. In some antibodies positions H58, H60, H61, H62, H64 and H65 are occupied by N, A, Q, K, Q and G respectively and L24 and L53 are occupied by R and S respectively. Some antibodies include at least 1, 2, 3, 4, 5, 6, 7, 8, 9, 10, 11, 12, 13 or 14 backmutations representing replacement of variable region human acceptor sequence residues with corresponding rat residues.

In some antibodies at least 1, 2, 3, 4, 5, 6, 7, 8, 9, 10, or 11 of positions H20, H48, H69, H71, H73, H76, H80, H88, H91 and H93 are occupied by L, I, M, A, K, N, V, A, F, and T respectively. In some antibodies at least 1, 2 or 3 of positions L46, L48 and L87 are occupied by V, V and F respectively. In some antibodies, each of positions H20, H48, H69, H71, H73, H76, H80, H88, H91 and H93 are occupied by L, I, M, A, K, N, V, A, F, and T respectively and each of L46, L48 and L87 are occupied by V, V and F respectively.

Insofar as humanized antibodies show any variation from the exemplified hSG16.17 VH3 VK2 humanized antibody, one possibility for such additional variation is additional backmutations in the variable region frameworks. Any or all of the positions backmutated in other exemplified humanized heavy or light chain mature variable regions can also be made (i.e., 1, 2, 3, 4, 5 or all 6) of H8 occupied by R, H67 occupied by A and H78 occupied by A, L40 occupied by S, L78 occupied by M and L85 occupied by D, or all 5 of H38 occupied by N, H40 occupied by R, H73 occupied by K, H82A occupied by S, and H83 occupied by T in the heavy chain and 1 or both of L3 occupied by K, and L20 occupied by I in the light chain. However, such additional backmutations are not preferred because they in general do not improve affinity and introducing more mouse residues may give increased risk of immunogenicity.

Another possible variation is to substitute more or fewer residues in the CDRs of the mouse antibody with corresponding residues from human CDRs sequences, typically from the CDRs of the human acceptor sequences used in designing the exemplified humanized antibodies. In some antibodies only part of the CDRs, namely the subset of CDR residues required for binding, termed the SDRs, are needed to retain binding in a humanized antibody. CDR residues not contacting antigen and not in the SDRs can be identified based on regions of Kabat CDRs lying outside CDRs according to other definitions, such as Chothia hypervariable loops (Chothia, *J. Mol. Biol.* 196:901, 1987), by molecular modeling and/or empirically, or as described in Gonzales et al., Mol. Immunol. 41: 863 (2004). In such humanized antibodies at positions in which one or more donor CDR residues is absent or in which an entire donor CDR is omitted, the amino acid occupying the position can be an amino acid occupying the corresponding position (by Kabat numbering) in the acceptor antibody sequence. The number of such substitutions of acceptor for donor amino acids in the CDRs to include reflects a balance of competing considerations. Such substitutions are potentially advantageous in decreasing the number of mouse amino acids in a humanized antibody and consequently decreasing potential immunogenicity. However, substitutions can also cause changes of affinity, and significant reductions in affinity are preferably avoided. Positions for substitution within CDRs and amino acids to substitute can also be selected empirically.

Although not preferred other amino acid substitutions can be made, for example, in framework residues not in contact with the CDRs, or even some potential CDR-contact residues amino acids within the CDRs. Often the replacements made in the variant humanized sequences are conservative with respect to the replaced hSG16.17 VH3 VK2 amino. Preferably, replacements relative to hSG16.17 VH3 VK2 (whether or not conservative) have no substantial effect on the binding affinity or potency of the humanized mAb, that is, its ability to bind human BCMA and inhibit growth of cancer cells.

Variants typically differ from the heavy and light chain mature variable region sequences of hSG16.17 VH3 VK2 by a small number (e.g., typically no more than 1, 2, 3, 5 or 10 in either the light chain or heavy chain mature variable region, or both) of replacements, deletions or insertions.

Other preferred combinations of humanized heavy and light chains include any of hSG16.17 VH1 VK2, VH1 VK3, VH1 VK4, VH1 VK4, VH3 VK2, VH3 VK3, VH3 VK4, and VH3 VK5, and VH5 VK2, VH5 VK3, VH5 VK4, VH5 VK5, as well as humanized antibodies in which the heavy and light chain variable regions show at least 90, 95, 96, 97, 98, or 99% identity with the heavy and light chain variable regions of any of these antibodies.

The invention provides humanized forms of the rat SG16.45 antibody including six exemplified humanized heavy chain mature variable regions (hSG16.45 VH1-6) (SEQ ID NOs: 27-32) and four exemplified humanized light chain mature variable regions (hSG16.45 VK1, 2, 3, and 5) (SEQ ID NOs: 35-38). The heavy and light chains can be combined in any permutations, with permutations hSG16.45 VH5 VK2, VH1 VK1 and VH1 VK5 being preferred. hSG16.45 HV5 VK2 shows greater than 85% sequence identity with human germline in both heavy and light chain variable regions (thus, qualifying for "humanized" designation under the new INN guidelines), high expression in CHO cells, a high proportion of monomers and adequate binding albeit slightly less than that of rat or chimeric SG16.45. hSG16.45 VH5 VK2 has 3 variable region backmutations (all in the heavy chain) and 3 Kabat CDR forward mutations, in which a rat residue in the Kabat CDRs is changed to the corresponding residue in the human acceptor sequence, such that overall the antibody has sufficient sequence identity to human germline sequences to be classified as humanized under INN guidelines.

The invention provides antibodies in which the heavy chain variable region shows at least 90% identity to hSG16.45 VH5 (SEQ ID NO: 31) and a light chain variable region at least 90% identical to hSG16.45 VK2. Some antibodies show at least 95%, 96%, 97%, 98% or 99% sequence identity to hSG16.45 VH5 and at least 95%, 96%, 97%, 98% or 99% sequence identity to VK2. Some such antibodies include the three Kabat CDRs (SEQ ID NOs: 152-154) of hSG16.45 VH5 (SEQ ID NO: 31) and three Kabat CDRs (SEQ ID NOs: 179-181) of hSG16.45 VK2 (SEQ ID NO: 36). Some such antibodies include the three Kabat CDRs (SEQ ID NOs: 152-154) of hSG16.45 VH5 (SEQ ID NO: 31) and three Kabat CDRs (SEQ ID NOs: 179-181) of hSG16.45 VK2 (SEQ ID NO: 36) provided that position H50 can be occupied by A or S and position L24 can be occupied by R or L and position L26 can be occupied by S or T. Preferably positions H50 is occupied by A and positions L24 and L26 are occupied by R and S. These recited residues represent amino acids from a human acceptor sequence occupying positions within the Kabat CDRs. Some antibodies have at least 1, 2, or 3 rat residues in the human Kabat CDRs replaced with corresponding residues from a human acceptor sequence. In some antibodies positions H50, L24 and L26 are occupied by A, R and S respectively. Some antibodies include at least 1, 2, or 3 backmutations representing replacement of variable region human acceptor sequence residues with corresponding rat residues.

In some antibodies at least 1, 2, or 3, of positions H30, H93 and H94 are occupied by N, T and S respectively. In some antibodies, each of positions H30, H93 and H94 are occupied by N, T and S respectively Insofar as humanized antibodies show any variation from the exemplified hSG16.45 VH5 VK2 humanized antibody, one possibility for such additional variation is additional backmutations in the variable region frameworks. Any or all of the positions backmutated in other exemplified humanized heavy or light chain mature variable regions can also be made (i.e., 1, 2, 3, or 4) of H37, H48, H76, H107 occupied by I, I, N, and V respectively and/or 1, 2, 3, 4, 5, 6 or 7 of L14, L19, L21, L38, L58, L71 and L78 occupied by A, V, I, H, V, Y, and M respectively. However, such additional backmutations are not preferred because they in general do not improve affinity and introducing more mouse residues may give increased risk of immunogenicity.

Another possible variation is to substitute more or fewer residues in the CDRs of the mouse antibody with corresponding residues from human CDRs sequences, typically from the CDRs of the human acceptor sequences used in designing the exemplified humanized antibodies. In some antibodies only part of the CDRs, namely the subset of CDR residues required for binding, termed the SDRs, are needed to retain binding in a humanized antibody. CDR residues not contacting antigen and not in the SDRs can be identified based on regions of Kabat CDRs lying outside CDRs according to other definitions, such as Chothia hypervariable loops (Chothia, *J. Mol. Biol.* 196:901, 1987), by molecular modeling and/or empirically, or as described in Gonzales et al., Mol. Immunol. 41: 863 (2004). In such humanized antibodies at positions in which one or more donor CDR residues is absent or in which an entire donor CDR is omitted, the amino acid occupying the position can be an amino acid occupying the corresponding position (by Kabat numbering) in the acceptor antibody sequence. The number of such substitutions of acceptor for donor amino acids in the CDRs to include reflects a balance of competing considerations. Such substitutions are potentially advantageous in decreasing the number of mouse amino acids in a humanized antibody and consequently decreasing potential immunogenicity. However, substitutions can also cause changes of affinity, and significant reductions in affinity are preferably avoided. Positions for substitution within CDRs and amino acids to substitute can also be selected empirically.

Although not preferred other amino acid substitutions can be made, for example, in framework residues not in contact with the CDRs, or even some potential CDR-contact residues amino acids within the CDRs. Often the replacements made in the variant humanized sequences are conservative with respect to the replaced hSG16.45 VH3 VK2. Preferably, replacements relative to hSG16.45 VH5 VK2 (whether or not conservative) have no substantial effect on the binding affinity or potency of the humanized mAb, that is, its ability to bind human BCMA and inhibit growth of cancer cells.

Variants typically differ from the heavy and light chain mature variable region sequences of SG16.45 VH5 VK2 by a small number (e.g., typically no more than 1, 2, 3, 5 or 10 in either the light chain or heavy chain mature variable region, or both) of replacements, deletions or insertions.

Other preferred combinations of humanized heavy and light chains include any of hSG16.45 VH1 VK1 and VH1 VK5, as well as humanized antibodies in which the heavy and light chain variable regions show at least 90, 95, 96, 97, 98, or 99% identity with the heavy and light chain variable regions of any of these antibodies.

C. Selection of Constant Region

Heavy and light chain variable regions of humanized antibodies can be linked to at least a portion of a human constant region. The choice of constant region depends, in part, whether antibody-dependent cell-mediated cytotoxicity, antibody dependent cellular phagocytosis and/or complement dependent cytotoxicity are desired. For example, human isotypes IgG1 and IgG3 have strong complement-dependent cytotoxicity, human isotype IgG2 weak complement-dependent cytotoxicity and human IgG4 lacks complement-dependent cytotoxicity. Human IgG1 and IgG3 also induce stronger cell mediated effector functions than human IgG2 and IgG4. Light chain constant regions can be lambda or kappa. Antibodies can be expressed as tetramers containing two light and two heavy chains, as separate heavy chains, light chains, as Fab, Fab', F(ab')2, and Fv, or as single chain antibodies in which heavy and light chain variable domains are linked through a spacer.

Human constant regions show allotypic variation and isoallotypic variation between different individuals, that is, the constant regions can differ in different individuals at one or more polymorphic positions. Isoallotypes differ from allotypes in that sera recognizing an isoallotype binds to a non-polymorphic region of a one or more other isotypes. Exemplary wild type human kappa and IgG1 constant region sequences (the latter with or without the C-terminal lysine) are provide in SEQ ID NOS: 3-5.

One or several amino acids at the amino or carboxy terminus of the light and/or heavy chain, such as the C-terminal lysine of the heavy chain, may be missing or derivatized in a proportion or all of the molecules. Substitutions can be made in the constant regions to reduce or increase effector function such as complement-mediated cytotoxicity or ADCC (see, e.g., Winter et al., U.S. Pat. No. 5,624,821; Tso et al., U.S. Pat. No. 5,834,597; and Lazar et al., Proc. Natl. Acad. Sci. USA 103:4005, 2006), or to prolong half-life in humans (see, e.g., Hinton et al., J. Biol. Chem. 279:6213, 2004).

Exemplary substitution include the amino acid substitution of the native amino acid to a cysteine residue is introduced at amino acid position 234, 235, 237, 239, 267, 298, 299, 326, 330, or 332, preferably an S239C mutation in a human IgG1 isotype (numbering is according to the EU index (Kabat, *Sequences of Proteins of Immunological Interest* (National Institutes of Health, Bethesda, Md., 1987 and 1991); see US 20100158909, which is herein incorporated reference). Sequences of a heavy chain constant regions with S239C with and without a C-terminal lysine are provided by SEQ ID NOS: 6 and 7. The presence of an additional cysteine residue allows interchain disulfide bond formation. Such interchain disulfide bond formation can cause steric hindrance, thereby reducing the affinity of the Fc region-FcγR binding interaction. The cysteine residue(s) introduced in or in proximity to the Fc region of an IgG constant region can also serve as sites for conjugation to therapeutic agents (i.e., coupling cytotoxic drugs using thiol specific reagents such as maleimide derivatives of drugs. The presence of a therapeutic agent causes steric hindrance, thereby further reducing the affinity of the Fc region-FcγR binding interaction. Other substitutions at any of positions 234, 235, 236 and/or 237 reduce affinity for Fcγ receptors, particularly FcγRI receptor (see, e.g., U.S. Pat. Nos. 6,624,821, 5,624, 821.) A preferred combination of mutations is S239D, A330L and I332E, which increases the affinity of the Fc domain for FcγRIIIA and consequently increases ADCC.

The in vivo half-life of an antibody can also impact its effector functions. The half-life of an antibody can be increased or decreased to modify its therapeutic activities. FcRn is a receptor that is structurally similar to MHC Class I antigen that non-covalently associates with β2-microglobulin. FcRn regulates the catabolism of IgGs and their transcytosis across tissues (Ghetie and Ward, 2000, *Annu. Rev. Immunol.* 18:739-766; Ghetie and Ward, 2002, *Immunol. Res.* 25:97-113). The IgG-FcRn interaction takes place at pH 6.0 (pH of intracellular vesicles) but not at pH 7.4 (pH of blood); this interaction enables IgGs to be recycled back to the circulation (Ghetie and Ward, 2000, *Ann. Rev. Immunol.* 18:739-766; Ghetie and Ward, 2002, *Immunol. Res.* 25:97-113). The region on human IgG1 involved in FcRn binding has been mapped (Shields et al., 2001, *J. Biol. Chem.* 276:6591-604). Alanine substitutions at positions Pro238, Thr256, Thr307, Gln311, Asp312, Glu380, Glu382, or Asn434 of human IgG1 enhance FcRn binding (Shields et al., 2001, *J. Biol. Chem.* 276:6591-604). IgG1 molecules harboring these substitutions have longer serum half-lives. Consequently, these modified IgG1 molecules may be able to carry out their effector functions, and hence exert their therapeutic efficacies, over a longer period of time compared to unmodified IgG1. Other exemplary substitutions for increasing binding to FcRn include a Gln at position 250 and/or a Leu at position 428. EU numbering is used for all positions in the constant region.

Oligosaccharides covalently attached to the conserved Asn297 are involved in the ability of the Fc region of an IgG to bind FcγR (Lund et al., 1996, *J. Immunol.* 157:4963-69; Wright and Morrison, 1997, *Trends Biotechnol.* 15:26-31). Engineering of this glycoform on IgG can significantly improve IgG-mediated ADCC. Addition of bisecting N-acetylglucosamine modifications (Umana et al., 1999, *Nat. Biotechnol.* 17:176-180; Davies et al., 2001, *Biotech. Bioeng.* 74:288-94) to this glycoform or removal of fucose (Shields et al., 2002, *J. Biol. Chem.* 277:26733-40;

Shinkawa et al., 2003, *J. Biol. Chem.* 278:6591-604; Niwa et al., 2004, *Cancer Res.* 64:2127-33) from this glycoform are two examples of IgG Fc engineering that improves the binding between IgG Fc and FcγR, thereby enhancing Ig-mediated ADCC activity.

A systemic substitution of solvent-exposed amino acids of human IgG1 Fc region has generated IgG variants with altered FcγR binding affinities (Shields et al., 2001, *J. Biol. Chem.* 276:6591-604). When compared to parental IgG1, a subset of these variants involving substitutions at Thr256/Ser298, Ser298/Glu333, Ser298/Lys334, or Ser298/Glu333/Lys334 to Ala demonstrate increased in both binding affinity toward FcγR and ADCC activity (Shields et al., 2001, *J. Biol. Chem.* 276:6591-604; Okazaki et al., 2004, *J. Mol. Biol.* 336:1239-49).

Complement fixation activity of antibodies (both C1q binding and CDC activity) can be improved by substitutions at Lys326 and Glu333 (Idusogie et al., 2001, *J. Immunol.* 166:2571-2575). The same substitutions on a human IgG2 backbone can convert an antibody isotype that binds poorly to C1q and is severely deficient in complement activation activity to one that can both bind C1q and mediate CDC (Idusogie et al., 2001, *J. Immunol.* 166:2571-75). Several other methods have also been applied to improve complement fixation activity of antibodies. For example, the grafting of an 18-amino acid carboxyl-terminal tail piece of IgM to the carboxyl-termini of IgG greatly enhances their CDC activity. This is observed even with IgG4, which normally has no detectable CDC activity (Smith et al., 1995, *J. Immunol.* 154:2226-36). Also, substituting Ser444 located close to the carboxy-terminal of IgG1 heavy chain with Cys induced tail-to-tail dimerization of IgG1 with a 200-fold increase of CDC activity over monomeric IgG1 (Shopes et al., 1992, *J. Immunol.* 148:2918-22). In addition, a bispecific diabody construct with specificity for C1q also confers CDC activity (Kontermann et al., 1997, *Nat. Biotech.* 15:629-31).

Complement activity can be reduced by mutating at least one of the amino acid residues 318, 320, and 322 of the heavy chain to a residue having a different side chain, such as Ala. Other alkyl-substituted non-ionic residues, such as Gly, Ile, Leu, or Val, or such aromatic non-polar residues as Phe, Tyr, Trp and Pro in place of any one of the three residues also reduce or abolish C1q binding. Ser, Thr, Cys, and Met can be used at residues 320 and 322, but not 318, to reduce or abolish C1q binding activity. Replacement of the 318 (Glu) residue by a polar residue may modify but not abolish C1q binding activity. Replacing residue 297 (Asn) with Ala results in removal of lytic activity but only slightly reduces (about three fold weaker) affinity for C1q. This alteration destroys the glycosylation site and the presence of carbohydrate that is required for complement activation. Any other substitution at this site also destroys the glycosylation site. The following mutations and any combination thereof also reduce C1q binding: D270A, K322A, P329A, and P311S (see WO 06/036291).

Reference to a human constant region includes a constant region with any natural allotype or any permutation of residues occupying polymorphic positions in natural allotypes. Also, up to 1, 2, 5, or 10 mutations may be present relative to a natural human constant region, such as those indicated above to reduce Fcγ receptor binding or increase binding to FcRN.

D. Expression of Recombinant Antibodies

Humanized, chimeric or veneered antibodies are typically produced by recombinant expression. Recombinant polynucleotide constructs typically include an expression control sequence operably linked to the coding sequences of antibody chains, including naturally-associated or heterologous promoter regions. Preferably, the expression control sequences are eukaryotic promoter systems in vectors capable of transforming or transfecting eukaryotic host cells. Once the vector has been incorporated into the appropriate host, the host is maintained under conditions suitable for high level expression of the nucleotide sequences, and the collection and purification of the crossreacting antibodies.

Mammalian cells are a preferred host for expressing nucleotide segments encoding immunoglobulins or fragments thereof. See Winnacker, *From Genes to Clones*, (VCH Publishers, NY, 1987). A number of suitable host cell lines capable of secreting intact heterologous proteins have been developed in the art, and include CHO cell lines (e.g., DG44), various COS cell lines, HeLa cells, HEK293 cells, L cells, and non-antibody-producing myelomas including Sp2/0 and NS0. Preferably, the cells are nonhuman. Expression vectors for these cells can include expression control sequences, such as an origin of replication, a promoter, an enhancer (Queen et al., *Immunol. Rev.* 89:49 (1986)), and necessary processing information sites, such as ribosome binding sites, RNA splice sites, polyadenylation sites, and transcriptional terminator sequences. Preferred expression control sequences are promoters derived from endogenous genes, cytomegalovirus, SV40, adenovirus, bovine papillomavirus, and the like. See Co et al., *J. Immunol.* 148:1149 (1992).

Once expressed, antibodies can be purified according to standard procedures of the art, including HPLC purification, column chromatography, gel electrophoresis and the like (see generally, Scopes, *Protein Purification* (Springer-Verlag, NY, 1982)).

E. Glycosylation Variants

Antibodies may be glycosylated at conserved positions in their constant regions (Jefferis and Lund, (1997) Chem. Immunol. 65:111-128; Wright and Morrison, (1997) TibTECH 15:26-32). The oligosaccharide side chains of the immunoglobulins affect the protein's function (Boyd et al., (1996) Mol. Immunol. 32:1311-1318; Wittwe and Howard, (1990) Biochem. 29:4175-4180), and the intramolecular interaction between portions of the glycoprotein which can affect the conformation and presented three-dimensional surface of the glycoprotein (Hefferis and Lund, supra; Wyss and Wagner, (1996) Current Opin. Biotech. 7:409-416). Oligosaccharides may also serve to target a given glycoprotein to certain molecules based upon specific recognition structures. For example, it has been reported that in agalactosylated IgG, the oligosaccharide moiety 'flips' out of the inter-CH2 space and terminal N-acetylglucosamine residues become available to bind mannose binding protein (Malhotra et al., (1995) Nature Med. 1:237-243). Removal by glycopeptidase of the oligosaccharides from CAMPATH-1H (a recombinant humanized murine monoclonal IgG1 antibody which recognizes the CDw52 antigen of human lymphocytes) produced in Chinese Hamster Ovary (CHO) cells resulted in a complete reduction in complement mediated lysis (CMCL) (Boyd et al., (1996) Mol. Immunol. 32:1311-1318), while selective removal of sialic acid residues using neuraminidase resulted in no loss of DMCL. Glycosylation of antibodies has also been reported to affect antibody-dependent cellular cytotoxicity (ADCC). In particular, CHO cells with tetracycline-regulated expression of β(1,4)-N-acetylglucosaminyltransferase III (GnTIII), a glycosyltransferase catalyzing formation of bisecting GlcNAc, was reported to have improved ADCC activity (Umana et al. (1999) Mature Biotech. 17:176-180).

Glycosylation of antibodies is typically either N-linked or O-linked. N-linked refers to the attachment of the carbohydrate moiety to the side chain of an asparagine residue. The tripeptide sequences asparagine-X-serine and asparagine-X-threonine, where X is any amino acid except proline, are the recognition sequences for enzymatic attachment of the carbohydrate moiety to the asparagine side chain. Thus, the presence of either of these tripeptide sequences in a polypeptide creates a potential glycosylation site. O-linked glycosylation refers to the attachment of one of the sugars N-aceylgalactosamine, galactose, or xylose to a hydroxyamino acid, most commonly serine or threonine, although 5-hydroxyproline or 5-hydroxylysine may also be used.

Glycosylation variants of antibodies are variants in which the glycosylation pattern of an antibody is altered. By altering is meant deleting one or more carbohydrate moieties found in the antibody, adding one or more carbohydrate moieties to the antibody, changing the composition of glycosylation (glycosylation pattern), the extent of glycosylation, etc.

Addition of glycosylation sites to the antibody can be accomplished by altering the amino acid sequence such that it contains one or more of the above-described tripeptide sequences (for N-linked glycosylation sites). The alteration may also be made by the addition of, or substitution by, one or more serine or threonine residues to the sequence of the original antibody (for O-linked glycosylation sites). Similarly, removal of glycosylation sites can be accomplished by amino acid alteration within the native glycosylation sites of the antibody.

The amino acid sequence is usually altered by altering the underlying nucleic acid sequence. These methods include isolation from a natural source (in the case of naturally-occurring amino acid sequence variants) or preparation by oligonucleotide-mediated (or site-directed) mutagenesis, PCR mutagenesis, and cassette mutagenesis of an earlier prepared variant or a non-variant version of the antibody.

The glycosylation (including glycosylation pattern) of antibodies may also be altered without altering the amino acid sequence or the underlying nucleotide sequence. Glycosylation largely depends on the host cell used to express the antibody. Since the cell type used for expression of recombinant glycoproteins, e.g., antibodies, as potential therapeutics is rarely the native cell, significant variations in the glycosylation pattern of the antibodies can be expected. See, e.g., Hse et al., (1997) J. Biol. Chem. 272:9062-9070. In addition to the choice of host cells, factors which affect glycosylation during recombinant production of antibodies include growth mode, media formulation, culture density, oxygenation, pH, purification schemes and the like. Various methods have been proposed to alter the glycosylation pattern achieved in a particular host organism including introducing or overexpressing certain enzymes involved in oligosaccharide production (U.S. Pat. Nos. 5,047,335; 5,510,261; 5,278,299). Glycosylation, or certain types of glycosylation, can be enzymatically removed from the glycoprotein, for example using endoglycosidase H (Endo H). In addition, the recombinant host cell can be genetically engineered, e.g., make defective in processing certain types of polysaccharides. These and similar techniques are well known in the art.

The glycosylation structure of antibodies can be readily analyzed by conventional techniques of carbohydrate analysis, including lectin chromatography, NMR, Mass spectrometry, HPLC, GPC, monosaccharide compositional analysis, sequential enzymatic digestion, and HPAEC-PAD, which uses high pH anion exchange chromatography to separate oligosaccharides based on charge. Methods for releasing oligosaccharides for analytical purposes are also known, and include, without limitation, enzymatic treatment (commonly performed using peptide-N-glycosidase F/endo-β-galactosidase), elimination using harsh alkaline environment to release mainly O-linked structures, and chemical methods using anhydrous hydrazine to release both N- and O-linked oligosaccharides A preferred form of modification of glycosylation of antibodies is reduced core fucosylation. "Core fucosylation" refers to addition of fucose ("fucosylation") to N-acetylglucosamine ("GlcNAc") at the reducing terminal of an N-linked glycan.

A "complex N-glycoside-linked sugar chain" is typically bound to asparagine 297 (according to the number of Kabat). As used herein, the complex N-glycoside-linked sugar chain has a biantennary composite sugar chain, mainly having the following structure:

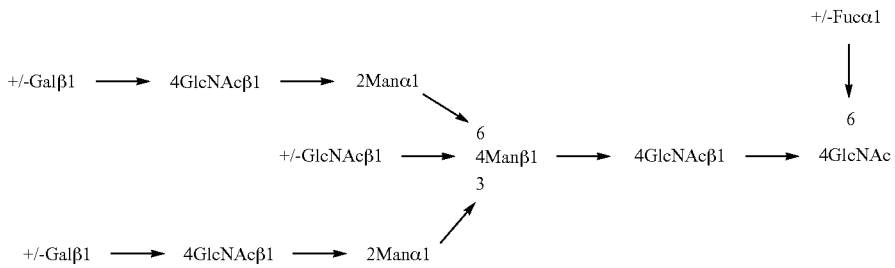

where ± indicates the sugar molecule can be present or absent, and the numbers indicate the position of linkages between the sugar molecules. In the above structure, the sugar chain terminal which binds to asparagine is called a reducing terminal (at right), and the opposite side is called a non-reducing terminal. Fucose is usually bound to N-acetylglucosamine ("GlcNAc") of the reducing terminal, typically by an α1,6 bond (the 6-position of GlcNAc is linked to the 1-position of fucose). "Gal" refers to galactose, and "Man" refers to mannose.

A "complex N-glycoside-linked sugar chain" includes 1) a complex type, in which the non-reducing terminal side of the core structure has one or more branches of galactose-N-acetylglucosamine (also referred to as "gal-GlcNAc") and the non-reducing terminal side of Gal-GlcNAc optionally has a sialic acid, bisecting N-acetylglucosamine or the like; or 2) a hybrid type, in which the non-reducing terminal side of the core structure has both branches of a high mannose N-glycoside-linked sugar chain and complex N-glycoside-linked sugar chain.

In some embodiments, the "complex N-glycoside-linked sugar chain" includes a complex type in which the non-reducing terminal side of the core structure has zero, one or more branches of galactose-N-acetylglucosamine (also referred to as "gal-GlcNAc") and the non-reducing terminal side of Gal-GlcNAc optionally further has a structure such as a sialic acid, bisecting N-acetylglucosamine or the like.

According to the present methods, typically only a minor amount of fucose is incorporated into the complex N-glycoside-linked sugar chain(s) of humanized, chimeric or veneered SG16.17 or SG16.45 antibodies. For example, in various embodiments, less than about 60%, less than about 50%, less than about 40%, less than about 30%, less than about 20%, less than about 15%, less than about 10%, less than about 5%, or less than about 3% of the molecules of an antibody have core fucosylation by fucose. In some embodiments, about 2% of the molecules of the antibody has core fucosylation by fucose.

In certain embodiments, only a minor amount of a fucose analog (or a metabolite or product of the fucose analog) is incorporated into the complex N-glycoside-linked sugar chain(s). For example, in various embodiments, less than about 60%, less than about 50%, less than about 40%, less than about 30%, less than about 20%, less than about 15%, less than about 10%, less than about 5%, or less than about 3% of humanized, chimeric or veneered SG16.17 or SG16.45 antibodies have core fucosylation by a fucose analog or a metabolite or product of the fucose analog. In some embodiments, about 2% of humanized, chimeric or veneered SG16.17 antibodies have core fucosylation by a fucose analog or a metabolite or product of the fucose analog.

Methods of making non-fucosylated antibodies by incubating antibody-producing cells with a fucose analogue are described, e.g., in WO2009/135181. Briefly, cells that have been engineered to express humanized, chimeric or veneered SG16.17 antibodies antibody are incubated in the presence of a fucose analogue or an intracellular metabolite or product of the fucose analog. An intracellular metabolite can be, for example, a GDP-modified analog or a fully or partially de-esterified analog. A product can be, for example, a fully or partially de-esterified analog. In some embodiments, a fucose analogue can inhibit an enzyme(s) in the fucose salvage pathway. For example, a fucose analog (or an intracellular metabolite or product of the fucose analog) can inhibit the activity of fucokinase, or GDP-fucose-pyrophosphorylase. In some embodiments, a fucose analog (or an intracellular metabolite or product of the fucose analog) inhibits fucosyltransferase (preferably a 1,6-fucosyltransferase, e.g., the FUT8 protein). In some embodiments, a fucose analog (or an intracellular metabolite or product of the fucose analog) can inhibit the activity of an enzyme in the de novo synthetic pathway for fucose. For example, a fucose analog (or an intracellular metabolite or product of the fucose analog) can inhibit the activity of GDP-mannose 4,6-dehydratase or/or GDP-fucose synthetase. In some embodiments, the fucose analog (or an intracellular metabolite or product of the fucose analog) can inhibit a fucose transporter (e.g., GDP-fucose transporter).

In one embodiment, the fucose analogue is 2-flurofucose. Methods of using fucose analogues in growth medium and other fucose analogues are disclosed, e.g., in WO/2009/135181, which is herein incorporated by reference.

Other methods for engineering cell lines to reduce core fucosylation included gene knock-outs, gene knock-ins and RNA interference (RNAi). In gene knock-outs, the gene encoding FUT8 (alpha 1,6-fucosyltransferase enzyme) is inactivated. FUT8 catalyzes the transfer of a fucosyl residue from GDP-fucose to position 6 of Asn-linked (N-linked) GlcNac of an N-glycan. FUT8 is reported to be the only enzyme responsible for adding fucose to the N-linked biantennary carbohydrate at Asn297. Gene knock-ins add genes encoding enzymes such as GNTIII or a golgi alpha mannosidase II. An increase in the levels of such enzymes in cells diverts monoclonal antibodies from the fucosylation pathway (leading to decreased core fucosylation), and having increased amount of bisecting N-acetylglucosamines. RNAi typically also targets FUT8 gene expression, leading to decreased mRNA transcript levels or knocking out gene expression entirely. Any of these methods can be used to generate a cell line that would be able to produce a non-fucosylated antibody, e.g., a humanized, chimeric or veneered SG16.17 antibody.

Many methods are available to determine the amount of fucosylation on an antibody. Methods include, e.g., LC-MS via PLRP-S chromatography and electrospray ionization quadrupole TOF MS.

IV. Nucleic Acids

The invention further provides nucleic acids encoding any of the humanized heavy and light chains described above. Typically, the nucleic acids also encode a signal peptide fused to the mature heavy and light chains. Coding sequences on nucleic acids can be in operable linkage with regulatory sequences to ensure expression of the coding sequences, such as a promoter, enhancer, ribosome binding site, transcription termination signal and the like. The nucleic acids encoding heavy and light chains can occur in isolated form or can be cloned into one or more vectors. The nucleic acids can be synthesized by for example, solid state synthesis or PCR of overlapping oligonucleotides. Nucleic acids encoding heavy and light chains can be joined as one contiguous nucleic acid, e.g., within an expression vector, or can be separate, e.g., each cloned into its own expression vector.

V. Antibody Drug Conjugates

Anti-MCMA antibodies can be conjugated to cytotoxic moieties to form antibody-drug conjugates (ADCs). Particularly suitable moieties for conjugation to antibodies are cytotoxic agents (e.g., chemotherapeutic agents), prodrug converting enzymes, radioactive isotopes or compounds, or toxins (these moieties being collectively referred to as therapeutic agents or drugs). For example, an anti-BCMA antibody can be conjugated to a cytotoxic agent such as a chemotherapeutic agent, or a toxin (e.g., a cytostatic or cytocidal agent such as, e.g., abrin, ricin A, pseudomonas exotoxin, or diphtheria toxin). Examples of useful classes of cytotoxic agents include, for example, DNA minor groove binders, DNA alkylating agents, and tubulin inhibitors. Exemplary cytotoxic agents include, for example, auristatins, camptothecins, duocarmycins, etoposides, maytansines and maytansinoids (e.g., DM1 and DM4), taxanes, benzodiazepines (e.g., pyrrolo[1,4]benzodiazepines (PBDs), indolinobenzodiazepines, and oxazolidinobenzodiazepines) and vinca alkaloids. Techniques for conjugating therapeutic agents to proteins, and in particular to antibodies, are well-known. (See, e.g., Alley et al., *Current Opinion in Chemical Biology* 2010 14:1-9; Senter, *Cancer J.*, 2008, 14(3):154-169.)

The therapeutic agent (e.g., cytotoxic agent) can be conjugated to the antibody in a manner that reduces its activity unless it is detached from the antibody (e.g., by hydrolysis, by antibody degradation, or by a cleaving agent). Such therapeutic agent can be attached to the antibody via a linker. A therapeutic agent conjugated to a linker is also referred to herein as a drug linker. The nature of the linker can vary widely. The components that make up the linker are chosen on the basis of their characteristics, which may be dictated in part, by the conditions at the site to which the conjugate is delivered.

The therapeutic agent can be attached to the antibody with a cleavable linker that is sensitive to cleavage in the intracellular environment of the anti-BCMA-expressing cancer cell but is not substantially sensitive to the extracellular environment, such that the conjugate is cleaved from the antibody when it is internalized by the anti-BCMA-expressing cancer cell (e.g., in the endosomal or, for example by virtue of pH sensitivity or protease sensitivity, in the lysosomal environment or in the caveolear environment). The therapeutic agent can also be attached to the antibody with a non-cleavable linker.

As indicated, the linker may comprise a cleavable unit. In some such embodiments, the structure and/or sequence of the cleavable unit is selected such that it is cleaved by the action of enzymes present at the target site (e.g., the target cell). In other embodiments, cleavable units that are cleavable by changes in pH (e.g. acid or base labile), temperature or upon irradiation (e.g. photolabile) may also be used.

In some embodiments, the cleavable unit may comprise one amino acid or a contiguous sequence of amino acids. The amino acid sequence may be the target substrate for an enzyme.

In some aspects, the cleavable unit is a peptidyl unit and is at least two amino acids long. Cleaving agents can include cathepsins B and D and plasmin (see, e.g., Dubowchik and Walker, 1999, *Pharm. Therapeutics* 83:67-123). Most typical are cleavable unit that are cleavable by enzymes that are present in anti-BCMA expressing cells, i.e., an enzyme cleavable linker. Accordingly, the linker can be cleaved by an intracellular peptidase or protease enzyme, including a lysosomal or endosomal protease. For example, a linker that is cleavable by the thiol-dependent protease cathepsin-B, which is highly expressed in cancerous tissue, can be used (e.g., a linker comprising a Phe-Leu or a Val-Cit peptide or a Val-Ala peptide).

In some embodiments, the linker will comprise a cleavable unit (e.g., a peptidyl unit) and the cleavable unit will be directly conjugated to the therapeutic agent. In other embodiments, the cleavable unit will be conjugated to the therapeutic agent via an additional functional unit, e.g., a self-immolative spacer unit or a non-self-immolative spacer unit. A non self-immolative spacer unit is one in which part or all of the spacer unit remains bound to the drug unit after cleavage of a cleavable unit (e.g., amino acid) from the antibody drug conjugate. To liberate the drug, an independent hydrolysis reaction takes place within the target cell to cleave the spacer unit from the drug.

With a self-immolative spacer unit, the drug is released without the need for drug for a separate hydrolysis step. In one embodiment, wherein the linker comprises a cleavable unit and a self immolative group, the cleavable unit is cleavable by the action of an enzyme and after cleavage of the cleavable unit, the self-immolative group(s) release the therapeutic agent. In some embodiments, the cleavable unit of the linker will be directly or indirectly conjugated to the therapeutic agent on one end and on the other end will be directly or indirectly conjugated to the antibody. In some such embodiments, the cleavable unit will be directly or indirectly (e.g., via a self-immolative or non-self-immolative spacer unit) conjugated to the therapeutic agent on one end and on the other end will be conjugated to the antibody via a stretcher unit. A stretcher unit links the antibody to the rest of the drug and/or drug linker. In one embodiment, the connection between the antibody and the rest of the drug or drug linker is via a maleimide group, e.g., via a maleimidocaproyl linker. In some embodiments, the antibody will be linked to the drug via a disulfide, for example the disulfide linked maytansinoid conjugates SPDB-DM4 and SPP-DM1.

The connection between the antibody and the linker can be via a number of different routes, e.g., through a thioether bond, through a disulfide bond, through an amide bond, or through an ester bond. In one embodiment, the connection between the anti-BCMA antibody and the linker is formed between a thiol group of a cysteine residue of the antibody and a maleimide group of the linker. In some embodiments, the interchain bonds of the antibody are converted to free thiol groups prior to reaction with the functional group of the linker. In some embodiments, a cysteine residue is an introduced into the heavy or light chain of an antibody and reacted with the linker. Positions for cysteine insertion by substitution in antibody heavy or light chains include those described in Published U.S. Application No. 2007-0092940 and International Patent Publication WO2008070593, each of which are incorporated by reference herein in its entirety and for all purposes.

In some embodiments, the antibody-drug conjugates have the following formula I:

$$L-(LU-D)_p \qquad (I)$$

wherein L is an anti-BCMA antibody, LU is a Linker unit and D is a Drug unit (i.e., the therapeutic agent). The subscript p ranges from 1 to 20. Such conjugates comprise an anti-BCMA antibody covalently linked to at least one drug via a linker. The Linker Unit is connected at one end to the antibody and at the other end to the drug.

The drug loading is represented by p, the number of drug molecules per antibody. Drug loading may range from 1 to 20 Drug units (D) per antibody. In some aspects, the subscript p will range from 1 to 20 (i.e., both integer and non-integer values from 1 to 20). In some aspects, the subscript p will be an integer from 1 to 20, and will represent the number of drug-linkers on a singular antibody. In other aspects, p represents the average number of drug-linker molecules per antibody, e.g., the average number of drug-linkers per antibody in a reaction mixture or composition (e.g., pharmaceutical composition), and can be an integer or non-integer value. Accordingly, in some aspects, for compositions (e.g., pharmaceutical compositions), p represents the average drug loading of the antibody-drug conjugates in the composition, and p ranges from 1 to 20.

In some embodiments, p is from about 1 to about 8 drugs per antibody. In some embodiments, p is 1. In some embodiments, p is 2. In some embodiments, p is from about 2 to about 8 drugs per antibody. In some embodiments, p is from about 2 to about 6, 2 to about 5, or 2 to about 4 drugs per antibody. In some embodiments, p is about 2, about 4, about 6 or about 8 drugs per antibody.

The average number of drugs per antibody unit in a preparation from a conjugation reaction may be characterized by conventional means such as mass spectroscopy, ELISA assay, HIC, and HPLC. The quantitative distribution of conjugates in terms of p may also be determined.

Exemplary antibody-drug conjugates include auristatin based antibody-drug conjugates, i.e., conjugates wherein the drug component is an auristatin drug. Auristatins bind tubulin, have been shown to interfere with microtubule dynamics and nuclear and cellular division, and have anticancer activity. Typically the auristatin based antibody-drug conjugate comprises a linker between the auristatin drug and the anti-BCMA antibody. The auristatins can be linked to the anti-BCMA antibody at any position suitable for conjugation to a linker. The linker can be, for example, a cleavable linker (e.g., a peptidyl linker) or a non-cleavable linker (e.g., linker released by degradation of the antibody). The auristatin can be auristatin E or a derivative thereof. The auristatin can be, for example, an ester formed between auristatin E and a keto acid. For example, auristatin E can be reacted with paraacetyl benzoic acid or benzoylvaleric acid to produce AEB and AEVB, respectively. Other typical auristatins include MMAF (monomethyl auristatin F), and MMAE (monomethyl auristatin E). The synthesis and structure of exemplary auristatins are described in U.S. Pat. Nos. 7,659,241, 7,498,298, 2009-0111756, 2009-0018086, and 7,968,687 each of which is incorporated herein by reference in its entirety and for all purposes.

Exemplary auristatin based antibody-drug conjugates include vcMMAE, vcMMAF and mcMMAF antibody-drug conjugates as shown below wherein Ab is an antibody as described herein and val-cit represents the valine-citrulline dipeptide:

Exemplary antibody-drug conjugates include PBD based antibody-drug conjugates; i.e., antibody-drug conjugates wherein the drug component is a PBD drug.

PBDs are of the general structure:

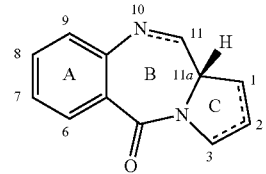

They differ in the number, type and position of substituents, in both their aromatic A rings and pyrrolo C rings, and in the degree of saturation of the C ring. In the B-ring there is either an imine (N=C), a carbinolamine (NH—CH(OH)), or a carbinolamine methyl ether (NH—CH(OMe)) at the N10-C11 position, which is the electrophilic center responsible for alkylating DNA. All of the known natural products have an (S)-configuration at the chiral C11a position which

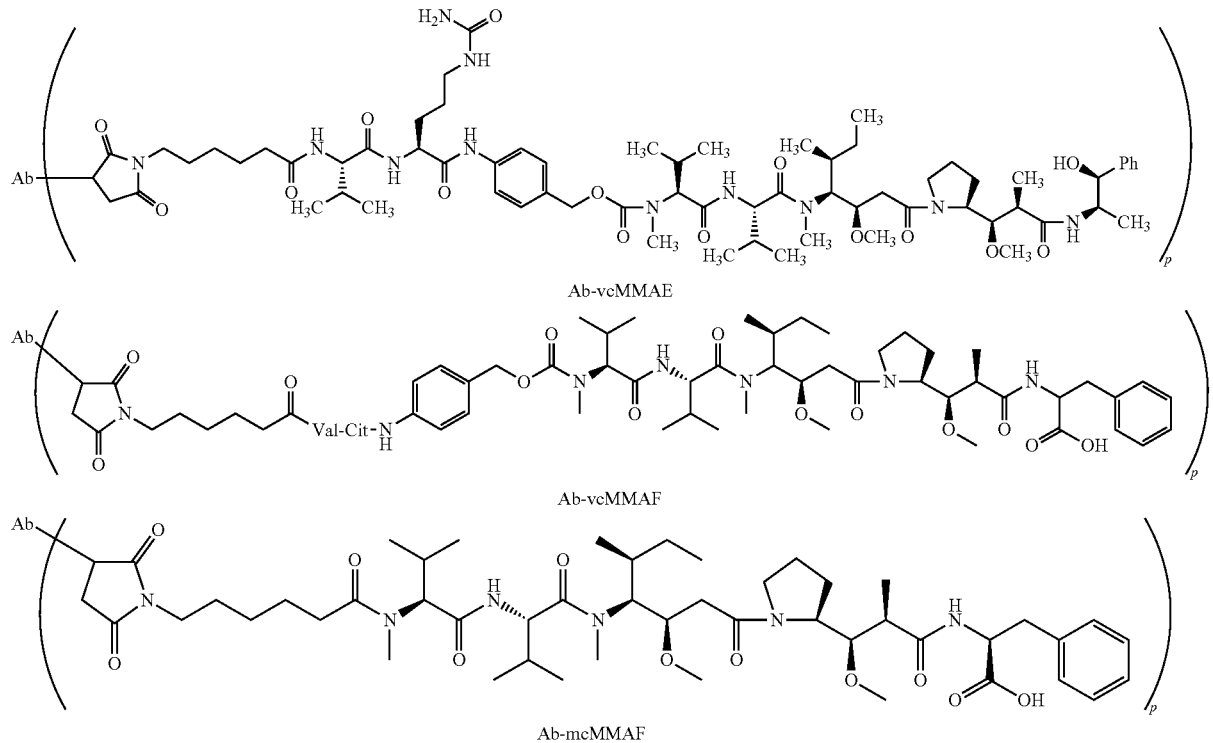

or a pharmaceutically acceptable salt thereof. The drug loading is represented by p, the number of drug-linker molecules per antibody. Depending on the context, p can represent the average number of drug-linker molecules per antibody, also referred to the average drug loading. The variable p ranges from 1 to 20 and is preferably from 1 to 8. In some preferred embodiments, when p represents the average drug loading, p ranges from about 2 to about 5. In some embodiments, p is about 2, about 3, about 4, or about 5. In some aspects, the antibody is conjugated to the linker via a sulfur atom of a cysteine residue. In some aspects, the cysteine residue is one that is engineered into the antibody. In other aspects, the cysteine residue is an interchain disulfide cysteine residue.

provides them with a right-handed twist when viewed from the C ring towards the A ring. This gives them the appropriate three-dimensional shape for isohelicity with the minor groove of B-form DNA, leading to a snug fit at the binding site. The ability of PBDs to form an adduct in the minor groove enables them to interfere with DNA processing, hence their use as antitumor agents.

The biological activity of these molecules can be potentiated by joining two PBD units together through their C8/C'-hydroxyl functionalities via a flexible alkylene linker. The PBD dimers are thought to form sequence-selective DNA lesions such as the palindromic 5'-Pu-GATC-Py-3' interstrand cross-link, which is thought to be mainly responsible for their biological activity.

In some embodiments, PBD based antibody-drug conjugates comprise a PBD dimer linked to an anti-BCMA antibody. The monomers that form the PBD dimer can be the same or different, i.e., symmetrical or unsymmetrical. The PBD dimer can be linked to the anti-BCMA antibody at any position suitable for conjugation to a linker. For example, in some embodiments, the PBD dimer will have a substituent at the C2 position that provides an anchor for linking the compound to the anti-BCMA antibody. In alternative embodiments, the N10 position of the PBD dimer will provide the anchor for linking the compound to the anti-BCMA antibody.

Typically the PBD based antibody-drug conjugate comprises a linker between the PBD drug and the anti-BCMA antibody. The linker may comprise a cleavable unit (e.g., an amino acid or a contiguous sequence of amino acids that is a target substrate for an enzyme) or a non-cleavable linker (e.g., linker released by degradation of the antibody). The linker may further comprise a maleimide group for linkage to the antibody, e.g., maleimidocaproyl. The linker may, in some embodiments, further comprise a self-immolative group, such as, for example, a p-aminobenzyl alcohol (PAB) unit.

An exemplary PBD for use as a conjugate is described in International Application No. WO 2011/130613 and is as follows wherein the wavy line indicates the site of attachment to the linker:

or a pharmaceutically acceptable salt thereof. The drug loading is represented by p, the number of drug-linker molecules per antibody. Depending on the context, p can represent the average number of drug-linker molecules per antibody, also referred to the average drug loading. The variable p ranges from 1 to 20 and is preferably from 1 to 8. In some preferred embodiments, when p represents the average drug loading, p ranges from about 2 to about 5. In some embodiments, p is about 2, about 3, about 4, or about 5. In some aspects, the antibody is conjugated to the drug linker via a sulfur atom of a cysteine residue that is engineered into the antibody. In some aspects, the cysteine residue is engineered into the antibody at position 239 (IgG1) as determined by the EU index (Kabat, *Sequences of Proteins of Immunological Interest* (National Institutes of Health, Bethesda, Md., 1987 and 1991).

VI. Animal Models of Immunological Disorders or BCMA-Expressing Cancers

The anti-BCMA antibodies or derivatives can be tested or validated in animal models of immunological disorders or BCMA-expressing cancers. Examples for animal models of systemic and organ-specific autoimmune diseases including diabetes, lupus, systemic sclerosis, Sjögren's Syndrome, experimental autoimmune encephalomyelitis (multiple sclerosis), thyroiditis, myasthenia gravis, arthritis, uveitis, inflammatory bowel disease have been described by Bigazzi, "Animal Models of Autoimmunity: Spontaneous and

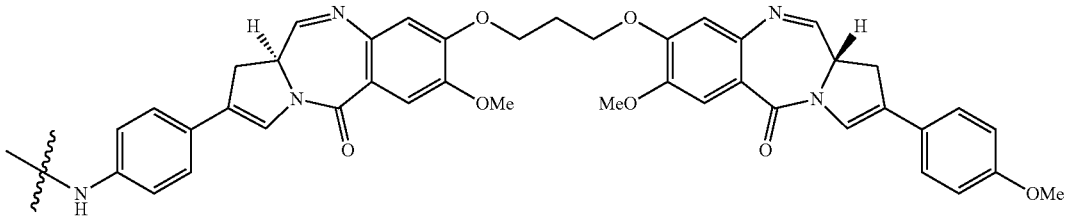 [SMILES: *Nc1ccc(C2=CN3C(=O)c4cc(OC)c(OCCCOc5cc6c(cc5OC)C(=O)N5C=C(c7ccc(OC)cc7)C[C@H]5C=N6)cc4N=C[C@@H]3C2)cc1]

or a pharmaceutically acceptable salt thereof. An exemplary linker is as follows wherein the wavy line indicates the site of attachment to the drug and the antibody is linked via the maleimide group.

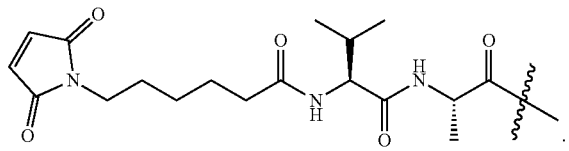 [SMILES: *C(=O)[C@H](C)NC(=O)[C@@H](NC(=O)CCCCCN1C(=O)C=CC1=O)C(C)C]

Exemplary PBDs based antibody-drug conjugates include antibody-drug conjugates as shown below wherein Ab is an antibody as described herein:

Induced," in The Autoimmune Diseases (Rose and Mackay eds., Academic Press, 1998) and in "Animal Models for Autoimmune and Inflammatory Disease," in Current Protocols in Immunology (Coligan et al. eds., Wiley and Sons, 1997).

Allergic conditions, e.g., asthma and dermatitis, can also be modeled in rodents. Airway hypersensitivity can be induced in mice by ovalbumin (Tomkinson et al., 2001, J. Immunol. 166:5792-800) or Schistosoma mansoni egg antigen (Tesciuba et al., 2001, J. Immunol. 167:1996-2003). The Nc/Nga strain of mice show marked increase in serum IgE and spontaneously develop atopic dermatitis-like leisons (Vestergaard et al., 2000, Mol. Med. Today 6:209-10; Watanabe et al., 1997, Int. Immunol. 9:461-66; Saskawa et al., 2001, Int. Arch. Allergy Immunol. 126:239-47).

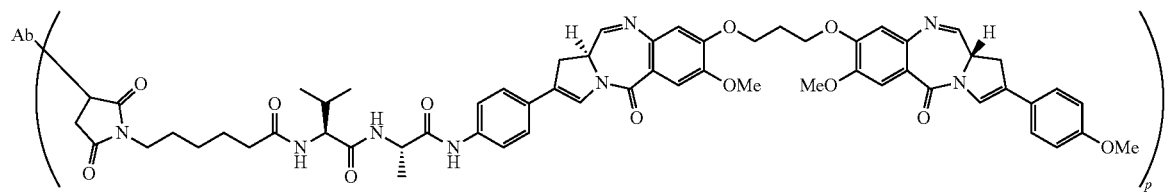

Injection of immuno-competent donor lymphocytes into a lethally irradiated histo-incompatible host is a classical approach to induce GVHD in mice. Alternatively, the parent B6D2F1 murine model provides a system to induce both acute and chronic GVHD. In this model the B6D2F1 mice are F1 progeny from a cross between the parental strains of C57BL/6 and DBA/2 mice. Transfer of DBA/2 lymphoid cells into non-irradiated B6D2F1 mice causes chronic GVHD, whereas transfer of C57BL/6, C57131110 or B10.D2 lymphoid cells causes acute GVHD (Slayback et al., 2000, Bone Marrow Transpl. 26:931-938; Kataoka et al., 2001, Immunology 103:310-318).

Additionally, both human hematopoietic stem cells and mature peripheral blood lymphoid cells can be engrafted into SCID mice, and these human lympho-hematopoietic cells remain functional in the SCID mice (McCune et al., 1988, Science 241:1632-1639; Kamel-Reid and Dick, 1988, Science 242:1706-1709; Mosier et al., 1988, Nature 335: 256-259). This has provided a small animal model system for the direct testing of potential therapeutic agents on human lymphoid cells. (See, e.g., Tournoy et al., 2001, J. Immunol. 166:6982-6991).

Moreover, small animal models to examine the in vivo efficacies of the anti-BCMA antibodies or derivatives can be created by implanting BCMA-expressing human tumor cell lines into appropriate immunodeficient rodent strains, e.g., athymic nude mice or SCID mice. Examples of BCMA-expressing human lymphoma cell lines include, for example, Daudi (Ghetie et al., 1994, Blood 83:1329-36; Ghetie et al., 1990, Int. J. Cancer 15:481-85; de Mont et al., 2001, Cancer Res. 61:7654-59), Ramos (Ma et al., 2002, Leukemia 16:60-6; Press et al., 2001, Blood 98:2535-43), HS-Sultan (Cattan and Maung, 1996, Cancer Chemother. Pharmacol. 38:548-52; Cattan and Douglas, 1994, Leuk. Res. 18:513-22), Raji (Ochakovskaya et al., 2001, Clin. Cancer Res. 7:1505-10; Breisto et al., 1999, Cancer Res. 59:2944-49), and CA46 (Kreitman et al., 1999, Int. J. Cancer 81:148-55). Non-limiting example of a BCMA-expressing Hodgkin's lymphoma line is L540cy (Barth et al., 2000, Blood 95:3909-14; Wahl et al., 2002, Cancer Res. 62:3736-42). Non-limiting examples of BCMA expressing human renal cell carcinoma cell lines include 786-0 (Ananth et al., 1999, Cancer Res. 59:2210-16; Datta et al., 2001, Cancer Res. 61:1768-75), ACHN (Hara et al., 2001, J. Urol. 166:2491-94; Miyake et al., 2002, *J. Urol.* 167:2203-08), Caki-1 (Prewett et al., 1998, Clin. Cancer Res. 4:2957-66; Shi and Siemann, 2002, Br. J. Cancer 87:119-26), and Caki-2 (Zellweger et al., 2001, Neoplasia 3:360-67). Non-limiting examples of BCMA-expressing nasopharyngeal carcinoma cell lines include C15 and C17 (Burson et al., 1988, Int. J. Cancer 42:599-606; Bernheim et al., 1993, Cancer Genet. Cytogenet. 66:11-5). Non-limiting examples of BCMA-expressing human glioma cell lines include U373 (Palma et al., 2000, Br. J. Cancer 82:480-7) and U87MG (Johns et al., 2002, Int. J. Cancer 98:398-408). These tumor cell lines can be established in immunodeficient rodent hosts either as solid tumor by subcutaneous injections or as disseminated tumors by intravenous injections. Once established within a host, these tumor models can be applied to evaluate the therapeutic efficacies of the anti-BCMA antibody or derivatives as described herein on modulating in vivo tumor growth.

VII. Therapeutic Applications

The anti-BCMA antibodies of the invention can be used to treat cancer. Some such cancers show detectable levels of BCMA measured at either the protein (e.g., by immunoassay using one of the exemplified antibodies) or mRNA level. Some such cancers show elevated levels of BCMA relative to noncancerous tissue of the same type, preferably from the same patient. An exemplary level of BCMA on cancer cells amenable to treatment is 5000-150000 BCMA molecules per cell, although higher or lower levels can be treated. Optionally, a level of BCMA in a cancer is measured before performing treatment.

Cancers treatable with antibodies of the invention include solid tumors and hematological cancers, such as leukemias and lymphomas. The antibodies are particularly suitable for cancers of B-cells. Examples of cancers treatable with the antibodies include: adult and pediatric acute myeloid leukemia (AML), chronic myeloid leukemia (CML), acute lymphocytic leukemia (ALL), chronic lymphocytic leukemia (CLL) and secondary leukemia; non-Hodgkin's lymphoma (NHL) and Hodgkin's disease; myelodysplastic syndromes (MDS), myeloproliferative syndromes (MPS) multiple myeloma, Waldenström's macroglobulinemia or Burkett's lymphoma., malignant plasma cell neoplasms, BCMA+high-grade lymphoma, Kahler's disease and myelomatosis; plasma cell leukemia; plasmacytoma; B-cell prolymphocytic leukemia; hairy cell leukemia; follicular lymphoma (including follicular non-Hodgkin's lymphoma types); Burkitt's lymphoma (Endemic Burkitt's lymphoma; sporadic Burkitt's lymphoma): marginal zone lymphoma (Mucosa-Associated Lymphoid Tissue: MALT 1 MALToma; Monocytoid B cell lymphoma; splenic lymphoma with villous lymphocytes); mantle cell lymphoma; large cell lymphoma (diffuse large cell; diffuse mixed cell; immunoblastic lymphoma; primary mediastinal B cell cymphoma; angiocentric lymphoma pulmonary B cell): small lymphocytic lymphoma (SLL); recursor B-lymphoblastic lymphoma; myeloid leukemia (granulocytic; myelogenous; acute myeloid leukemia; chronic myeloid leukemia; sub-acute myeloid leukemia; myeloid sarcoma; chloroma; granulocytic sarcoma; acute promyelocytic leukemia; acute myelomonocytic leukemia); Waldenstrom's macroglobulinemia, or other B-cell leukemia or lymphoma.

The antibodies of the invention are also useful for immune disorders mediated by immune cells expressing BCMA, particularly B-cell mediated disorders. Examples of such diseases include rheumatoid arthritis, systemic lupus E (SLE), Type I diabetes, asthma, atopic dermitus, allergic rhinitis, thrombocytopenic purpura, multiple sclerosis, psoriasis, Sjorgren's syndrome, Hashimoto's thyroiditis, Grave's disease, primary biliary cirrhosis, Wegener's granulomatosis, tuberculosis, and graft versus host disease immune-mediated thrombocytopenia, haemolytic anaemia, bullous pemphigoid, myasthenia gravis, Graves' disease, Addison's disease, pemphigus foliaceus, psoriasis, psoriatic arthritis, and ankylosing spondylitis.

Anti-BCMA antibodies alone or as drug-conjugates thereof, are administered in an effective regime meaning a dosage, route of administration and frequency of administration that delays the onset, reduces the severity, inhibits further deterioration, and/or ameliorates at least one sign or symptom of cancer. If a patient is already suffering from cancer, the regime can be referred to as a therapeutically effective regime. If the patient is at elevated risk of the cancer relative to the general population but is not yet experiencing symptoms, the regime can be referred to as a prophylactically effective regime. In some instances, therapeutic or prophylactic efficacy can be observed in an individual patient relative to historical controls or past experience in the same patient. In other instances, therapeutic or prophylactic efficacy can be demonstrated in a preclinical or clinical trial in a population of treated patients relative to a control population of untreated patients.

Exemplary dosages for a monoclonal antibody are 0.1 mg/kg to 50 mg/kg of the patient's body weight, more typically 1 mg/kg to 30 mg/kg, 1 mg/kg to 20 mg/kg, 1 mg/kg to 15 mg/kg, 1 mg/kg to 12 mg/kg, or 1 mg/kg to 10 mg/kg1, or 2 mg/kg to 30 mg/kg, 2 mg/kg to 20 mg/kg, 2 mg/kg to 15 mg/kg, 2 mg/kg to 12 mg/kg, or 2 mg/kg to 10 mg/kg, or 3 mg/kg to 30 mg/kg, 3 mg/kg to 20 mg/kg, 3 mg/kg to 15 mg/kg, 3 mg/kg to 12 mg/kg, or 3 mg/kg to 10 mg/kg. Exemplary dosages for active monoclonal antibody drug conjugates thereof, e.g., auristatins, are 1 mg/kg to 7.5 mg/kg, or 2 mg/kg to 7.5 mg/kg or 3 mg/kg to 7.5 mg/kg of the subject's body weight, or 0.1-20, or 0.5-5 mg/kg body weight (e.g., 0.5, 1, 2, 3, 4, 5, 6, 7, 8, 9 or 10 mg/kg) or 10-1500 or 200-1500 mg as a fixed dosage. Exemplary dosages for highly active monoclonal antibody drug conjugates thereof, e.g., PBDs, are 1.0 µg/kg to 1.0 mg/kg, or 1.0 µg/kg to 500.0 µg/kg of the subject's body weight. In some methods, the patient is administered then antibody or ADC every two, three or four weeks. The dosage depends on the frequency of administration, condition of the patient and response to prior treatment, if any, whether the treatment is prophylactic or therapeutic and whether the disorder is acute or chronic, among other factors.

Administration can be parenteral, intravenous, oral, subcutaneous, intra-arterial, intracranial, intrathecal, intraperitoneal, topical, intranasal or intramuscular. Administration can also be localized directly into a tumor. Administration into the systemic circulation by intravenous or subcutaneous administration is preferred. Intravenous administration can be, for example, by infusion over a period such as 30-90 min or by a single bolus injection.

The frequency of administration depends on the half-life of the antibody or antibody-drug conjugate in the circulation, the condition of the patient and the route of administration among other factors. The frequency can be daily, weekly, monthly, quarterly, or at irregular intervals in response to changes in the patient's condition or progression of the cancer being treated. An exemplary frequency for intravenous administration is between twice a week and quarterly over a continuous course of treatment, although more or less frequent dosing is also possible. Other exemplary frequencies for intravenous administration are between once weekly or once monthly over a continuous course of treatment, although more or less frequent dosing is also possible. For subcutaneous administration, an exemplary dosing frequency is daily to monthly, although more or less frequent dosing is also possible.

The number of dosages administered depends on the nature of the cancer or autoimmune disease (e.g., whether presenting acute or chronic symptoms) and the response of the disorder to the treatment. For acute disorders or acute exacerbations of a chronic disorder between 1 and 10 doses are often sufficient. Sometimes a single bolus dose, optionally in divided form, is sufficient for an acute disorder or acute exacerbation of a chronic disorder. Treatment can be repeated for recurrence of an acute disorder or acute exacerbation. For chronic disorders, an antibody can be administered at regular intervals, e.g., weekly, fortnightly, monthly, quarterly, every six months for at least 1, 5 or 10 years, or the life of the patient.

Pharmaceutical compositions for parenteral administration are preferably sterile and substantially isotonic and manufactured under GMP conditions. Pharmaceutical compositions can be provided in unit dosage form (i.e., the dosage for a single administration). Pharmaceutical compositions can be formulated using one or more physiologically acceptable carriers, diluents, excipients or auxiliaries. The formulation depends on the route of administration chosen.

For injection, antibodies can be formulated in aqueous solutions, preferably in physiologically compatible buffers such as Hank's solution, Ringer's solution, or physiological saline or acetate buffer (to reduce discomfort at the site of injection). The solution can contain formulatory agents such as suspending, stabilizing and/or dispersing agents. Alternatively antibodies can be in lyophilized form for constitution with a suitable vehicle, e.g., sterile pyrogen-free water, before use. The concentration of antibody in a liquid formulation can be e.g., 0.01-10 mg/ml, such as 1.0 mg/ml.

Treatment with antibodies of the invention can be combined with chemotherapy, radiation, stem cell treatment, surgery other treatments effective against the disorder being treated. Useful classes of other agents that can be administered with antibodies to BCMA include, for example, antibodies to other receptors expressed on cancerous cells, antitubulin agents (e.g., auristatins), DNA minor groove binders (e.g., PBDs), DNA replication inhibitors, alkylating agents (e.g., platinum complexes such as cis-platin, mono (platinum), bis(platinum) and tri-nuclear platinum complexes and carboplatin), anthracyclines, antibiotics, antifolates, antimetabolites, chemotherapy sensitizers, duocarmycins, etoposides, fluorinated pyrimidines, ionophores, lexitropsins, nitrosoureas, platinols, pre-forming compounds, purine antimetabolites, puromycins, radiation sensitizers, steroids, taxanes, topoisomerase inhibitors, vinca alkaloids, and the like. The same additional treatments just mentioned for cancer can also be used for immune mediated disorders. Additional agents for immune mediate disorders include immune suppressors such as mast cell degranulation inhibitors, anti-histamines, corticosteroids, NSAIDs, azathioprine, cyclophosphamide, leukeran, and cyclosporine and biologic anti-inflammatory agents, such as Tysabri® or Humira®.

Treatment with anti-BCMA antibodies, optionally in combination with any of the other agents or regimes described above alone or as an antibody drug conjugate, can increase the median progression-free survival or overall survival time of patients with cancer, especially when relapsed or refractory, by at least 30% or 40% but preferably 50%, 60% to 70% or even 100% or longer, compared to the same treatment (e.g., chemotherapy) but without the anti-BCMA antibody. In addition or alternatively, treatment (e.g., standard chemotherapy) including the anti-BCMA antibody, alone or as an antibody-drug conjugate, can increase the complete response rate, partial response rate, or objective response rate (complete+partial) of patients with tumors by at least 30% or 40% but preferably 50%, 60% to 70% or even 100% compared to the same treatment (e.g., chemotherapy) but without the anti-BCMA antibody.

Typically, in a clinical trial (e.g., a phase II, phase II/III or phase III trial), the aforementioned increases in median progression-free survival and/or response rate of the patients treated with standard therapy plus the anti-BCMA antibody, relative to the control group of patients receiving standard therapy alone (or plus placebo), are statistically significant, for example at the p=0.05 or 0.01 or even 0.001 level. The complete and partial response rates are determined by objective criteria commonly used in clinical trials for cancer, e.g., as listed or accepted by the National Cancer Institute and/or Food and Drug Administration.

VIII. Other Applications

The anti-BCMA antibodies disclosed herein can be used for detecting BCMA in the context of clinical diagnosis or treatment or in research. Expression of BCMA on a cancer provides an indication that the cancer is amenable to treatment with the antibodies of the present invention. The antibodies can also be sold as research reagents for laboratory research in detecting cells bearing BCMA and their response to various stimuli. In such uses, monoclonal antibodies can be labeled with fluorescent molecules, spin-labeled molecules, enzymes or radioisotypes, and can be provided in the form of kit with all the necessary reagents to perform the assay for BCMA. The antibodies can also be used to purify BCMA protein, e.g., by affinity chromatography.

Any feature, step, element, embodiment, or aspect of the invention can be used in combination with any other unless specifically indicated otherwise. Although the present invention has been described in some detail by way of illustration and example for purposes of clarity and understanding, it will be apparent that certain changes and modifications may be practiced within the scope of the appended claims.

EXAMPLES

Example 1: Antibody Development

Preparation of Recombinant BCMA Extracellular Domain (BCMA ECD)

The extracellular domain (ECD) of human (amino acids 1-51) and mouse BCMA (amino acids 1-46) were cloned and expressed as a GST fusion protein (pGEX4T1; Amersham Biosciences). Purified BCMA ECD was obtained by capturing the BCMA fusion protein with glutathione-Sepharose and releasing the BCMA ECD by protease digestion with thrombin. Thrombin was subsequently removed by benzamidine sepharose.

Identification of BCMA Expression on Malignant B-Cell Lines

Quantitative flow cytometry was performed on multiple myeloma cell lines using Vicky-1, a commercial antibody for BCMA (Alexis Biotechnology). Results showed that BCMA is prevalent among myeloma lines tested. NCI H929 showed positive cell surface staining for BCMA but lacked expression of either BR3 or TACI. Because NCI H929 expressed BCMA but not BR3 or TACI, it was used for cell-based screening of the BCMA hybridomas.

Development of a Transfected BCMA Cell Line.

Stable cell lines were developed by transfecting HEK 293 cells with either a full-length BCMA clone or an empty vector. Flow cytometry confirmed positive expression of BCMA on the surface of the BCMA transfected (293: BCMA) but not the vector empty control plasmid (293: vector). These cell lines were subsequently used as a tool to confirm the specificity of cloned BCMA antibodies.

Example 2: Immunization and Screening of Uncloned Hybridoma Wells

Immunization and Screening of Antiserum

Figure 1B:
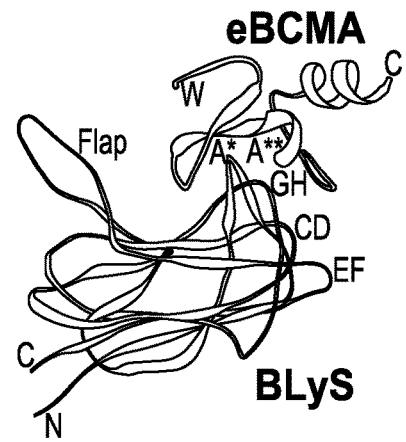
FIG. 1B shows the structural interaction of the extracellular domain of BCMA with BAFF.

Our immunization strategy used amino acids 1-50 of the BCMA ECD so that epitopes internal and external to ligand binding domain could be targeted by antibodies (FIGS. 1A and 1B) KLH-conjugated BCMA ECD was generated from a commercial source (Alexis Biochemicals). Rats were immunized KLH-conjugated BCMA using Titermax adjuvant until a maximum immune response was detected by ELISA. Immunized rats serum was also screened for ability to block APRIL binding in a plate-based assay. Rat 2-3 was selected for fusion because the antiserum had a significant titer of human BCMA antibodies and it displayed robust blocking activity.

Figure 2:
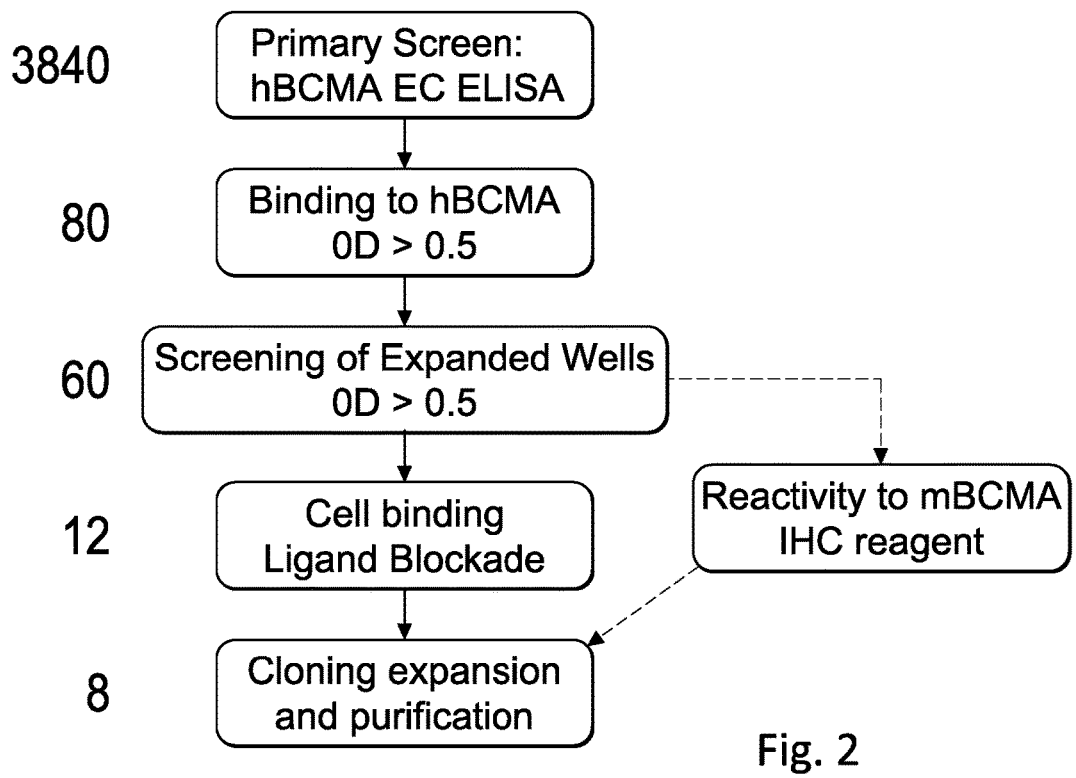
FIG. 2 shows an antibody selection procedure.
Figure 3:
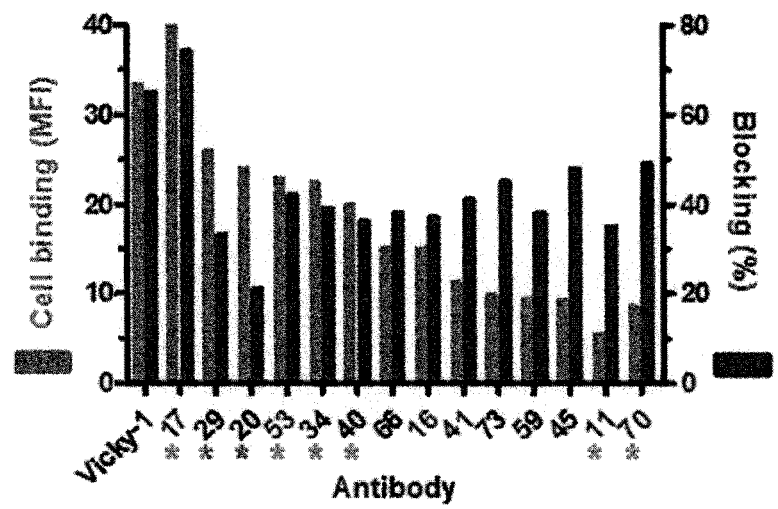
FIG. 3 shows cell binding data and ligand blockade activity for uncloned hybridoma wells.

Spleen cells from rat 2-3 were harvested, fused to X-63.Ag8.653.3.12.11 mouse myeloma cells and selected as described (Goding, 1989). Culture supernatants from the resulting hybridomas were screened by ELISA using purified hBCMA-GST (see flow chart in FIG. 2). Eighty positive wells were identified and selected for expansion. Sixty of the eighty positives wells continued to showed an OD>0.5 by ELISA following expansion. These sixty uncloned hybridoma wells were then screened in secondary assays for cell-based binding, ligand blockade activity, and cross-reactivity to mouse BCMA. This led to the identification of twelve lead BCMA hybridoma wells. Cell binding data and ligand blockade activity from these twelve lead wells is summarized in FIG. 3. Hybridoma well 17 showed cell binding and ligand blockade activity that superseded the commercial monoclonal Vicky-1 (Alexis Biochemicals). Eight wells (indicated with a red asterisk in FIG. 3) were taken forward for cloning based on their ability to bind BCMA-positive cells or block ligand binding.

Example 3: Characterization of Clonal Hybridomas

Cell Binding and Ligand Blockade Activity.

Hybridoma wells 11, 17, 20, 29, 40, 45 and 70 were taken through 2 rounds of limited dilution cloning. From this point forward, the antibodies will be designated with the formal clone ID shown in Table 1. The specific binding of the antibodies to 293: BCMA cells but not to the 293: vector control cells confirms that the antibodies are binding to BCMA.

TABLE 1

Formal Clone IDs.

| Uncloned Designation | Cloned ID |
| --- | --- |
| 11 | SG16.11 |
| 17 | SG16.17 |
| 20 | SG16.20 |
| 29 | SG16.29 |
| 40 | SG16.40 |
| 45 | SG16.45 |
| 70 | SG16.70 |

Figure 4:
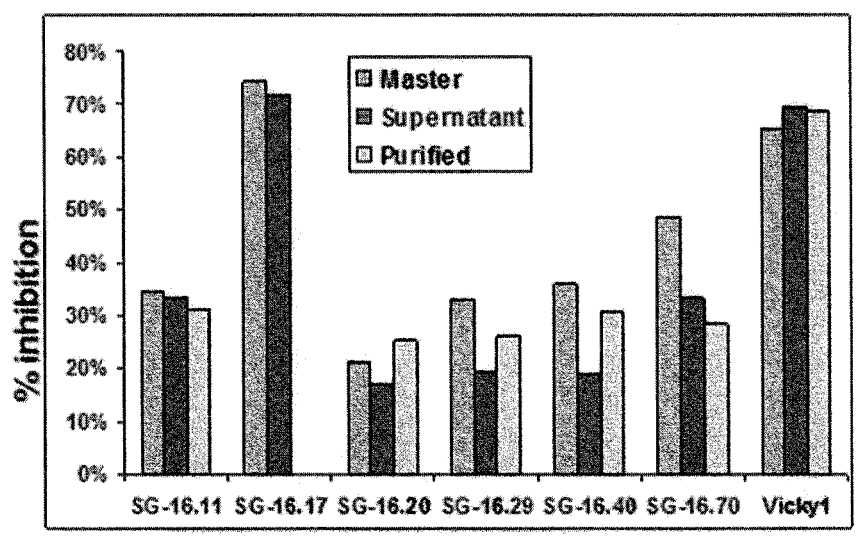
FIG. 4 shows blocking activity/percent inhibition of anti-BCMA antibodies.
Figure 5:
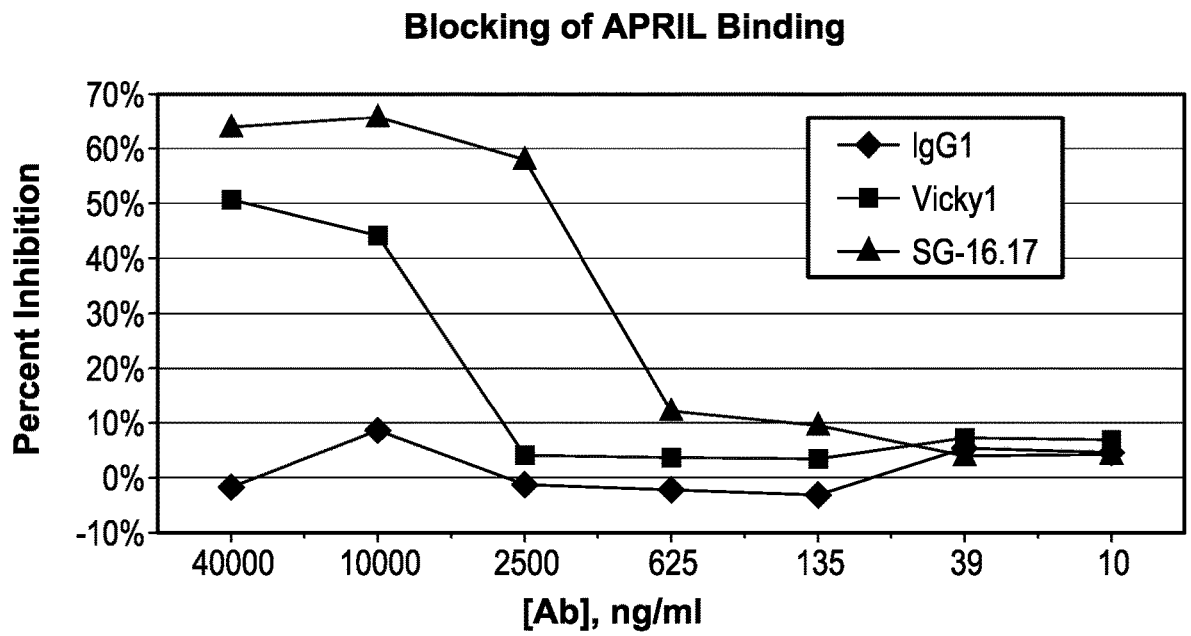
FIG. 5 shows inhibition of APRIL blocking titrated with anti-BCMA antibodies.

Ligand blockade activity of the new BCMA antibodies was compared using supernatant from the uncloned master well, supernatant from the cloned well and purified antibody from a cloned well (FIG. 4). A commercial antibody was used as a positive control. SG-16.17 gave significant blocking of APRIL binding using culture supernatant from the cloned hybridoma well. A titration of the SG16.17 blockade of APRIL binding was performed in a separate experiment using purified SG16.17 and the commercial antibody (FIG. 5). Purified SG16.17 displayed improved blocking activity across similar concentrations when compared to the commercial antibody. SG-16.45 showed dose-dependent inhibition of April binding although not as strongly as SG-16.17. Ligand blockade activity for the remaining BCMA antibodies (SG-16.11, SG16.20, SG16.29, SG16.40, and SG16.70) was more modest. Certain blocking BCMA antibodies show >75% inhibition of APRIL binding as was observed with SG-16.17. More "modest" blocking antibodies including SG-16.11, SG-16.20, SG-16.29, SG-16.40, and SG-16.70 showed about 30% inhibition for APRIL binding (FIG. 4).

Figure 6:
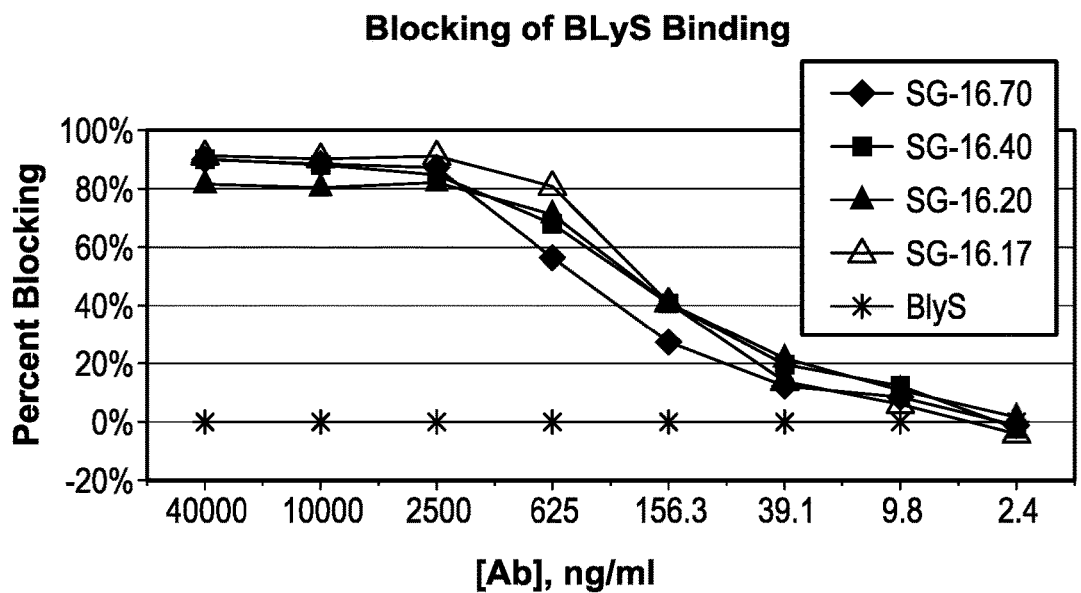
FIG. 6 shows a titration of BAFF blocking using anti-BCMA antibodies.

The ability of BAFF to bind immobilized BCMA was also analyzed in the presence and absence of purified BCMA antibodies. Pretreatment with BCMA antibodies SG16.17, SG16.40, SG16.20 and SG17.70 all resulted in a titratable inhibition of BAFF binding to BCMA (FIG. 6). The relative inhibition was determined by binding BAFF to immobilized BCMA in the absence of antibody treatment (FIG. 6, asterisk). Taken together, the data in FIGS. 5 and 6 shows that BCMA antibodies can block ligand binding of APRIL and BAFF to BCMA and thereby interfere with B cell survival signals.

Example 4: Testing SG16.17 and SG16.45 Antibodies for ADCC and Cytotoxicity as an ADC The SG16.17 antibody was converted into a rat-human chimeric IgG by fusing the rat $V_H$ and $V_L$ domains to wild-type human IgG1 heavy chain and K light chain constant domains, respectively. The chimerized antibody, designated cSG16.17 wild-type, showed similar antigen binding properties when compared with the parental antibody SG16.17. Next, we installed Fc mutations, S239D: A330L:I332E, known to enhance ADCC, to generate cSG16.17 mutant. Similar to cSG16.17 wild-type, generation of the Fc triple mutant did not alter the antigen-binding properties of cSG16.17 mutant. Evaluation of cSG16.17 wild-type and cSG16.17 mutant in an ADCC assay with purified natural killer cells resulted in dose-dependent lysis of JJN3 and U266 cells whereas no significant lysis was observed with a nonbinding human IgG control. The cSG16.17 wild-type antibody displayed limited ADCC activity on JJN3 cells, which was increased ~100-fold in potency and >2-fold in efficacy (maximal lysis) by cSG16.17 mutant. Similarly, for U266 cells, the ADCC activity of cSG16.17 mutant was enhanced ~100-fold in potency and 2-fold in efficacy compared with the parent chimeric antibody. The concentration of cSG16.17 mutant required for maximal lysis of both JJN3 and U266 cells was ~100 pmol/L. In contrast, the dissociation constant ($K_D$) of cSG16.17 on JJN3 and U266 cells was estimated as 15 and 10 nmol/L, respectively. Thus, maximal lysis by cSG16.17 mutant was achieved at concentrations well below those required to reach saturation binding.

We assessed the ability of SG16.17 and SG16.45 to induce cytotoxicity as ADCs using vcMMAF with a stoichiometry of eight drugs per antibody. SG16.17 or SG16.45-vcMMAF8 was potently cytotoxic against H929 cells. No decline in cell viability was observed using a nonbinding control ADC or unconjugated antibodies. We also examined the potency of SG16.17 ADC across other MM cell lines, including JJN3 and U266 cell lines. SG16.17-vcMMAF8 showed consistent and high potency (IC$_{50}$ values≤130 pmol/L) across all three MM cell lines whereas SG16.45-vcMMAF8 showed more variability and less overall potency.

Figure 12:
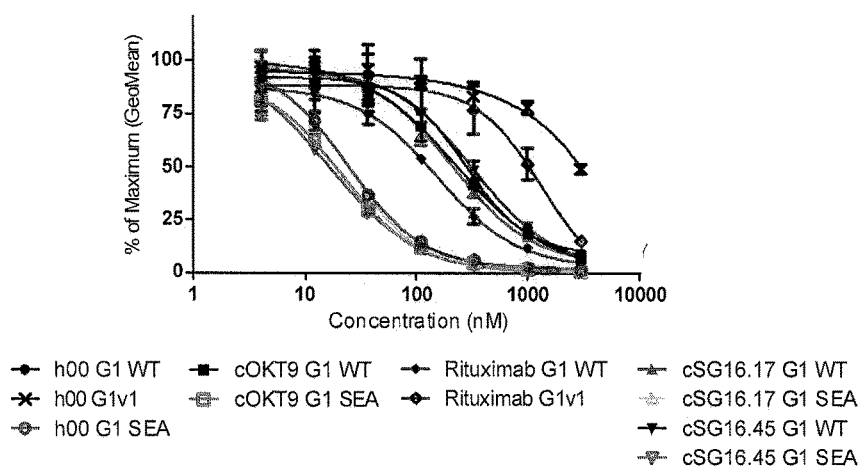
FIG. 12 shows competition binding assay showing binding of chimeric SG16.17 to human FcRIIIa.

Example 5: Testing SG16.17 Antibody for Binding to FcγRIIIa, and Signaling Through FcγRIIIa For the binding assay, CHO cells were transfected with FcγRIIIa (hCD16) and binding of labelled h00 antibody measured in competition with chimeric SG16.17 with wild type IgG1 and IgG1 S239D, A330L, I332E genotype, and various IgG1 control antibodies. FIG. 12 shows that chimeric SG16.17 competed more strongly than two control antibodies, rituximab and cOKT9. The mutant form of SG16.17 competed more strongly than the wild type IgG1 form. The signaling assay uses U266 target cells expressing BCMA, Jurkat effector cells expressing FcγRIIIa and engineered to express a luciferase reporter from a NFAT response element and Bio-Glo indicator. cSG16.17 G1 WT & S239D, A330L, I332E both elicited FcγRIIIa signaling with that from the S239D, A330L, I332E form being stronger (FIG. 13).

Example 6: Humanization of SG16.17

TABLE 2

Humanizing Mutations in hSG16.17 Heavy Chain Variants

| vH Variant | HV Exon Acceptor Sequence | Donor Framework Residues | Acceptor CDR Residues |
|---|---|---|---|
| hvH1 | HV1-2/HJ3 | H8, H20, H48, H67, H69, H71, H73, H76, H80, H88, H91, H93 | none |
| hvH2 | HV1-2/HJ3 | H20, H48, H69, H71, H73, H76, H80, H88, H91, H93 | H34, H50, H58, H60, H61, H62, H64, H65 |
| hvH3 | HV1-2/HJ3 | H20, H48, H67, H69, H71, H73, H76, H80, H88, H91, H93 | H58, H60, H61, H62, H64, H65 |
| hvH4 | HV1-2/HJ3 | H48, H67, H69, H71, H73, H76, H80, H88, H91, H93 | H34, H50, H58, H60, H61, H62, H64, H65 |
| hvH5 | HV1-46/HJ3 | H48, H67, H71, H73, H76, H78, H80, H91, H93 | none |
| hvH6 | HV1-46/HJ3 | H8, H20, H48, H71, H73, H76, H78, H80, H91, H93 | none |

TABLE 3

Humanizing Mutations in hSG16.17 Kappa Light Chain Variants

| vK Variant | KV Exon Acceptor Sequence | Donor Framework Residues | Acceptor CDR Residues |
|---|---|---|---|
| hVK2 | KV1-12/KJ5 | L46, L48, L87 | L53 |
| hVK3 | KV1-12/KJ5 | L46, L48, L87 | L24, L53 |
| hVK4 | KV1-12/KJ5 | L46, L48, L78, L85, L87 | none |
| hVK5 | KV1-12/KJ5 | L40, L46, L48, L87 | L24, L53 |

TABLE 4

Specific Framework Mutations in hSG16.17 Heavy Chain Variants

| Variant | H8 | H20 | H48 | H67 | H69 | H71 | H73 | H76 | H78 | H80 | H88 | H91 | H93 | % Human |
|---|---|---|---|---|---|---|---|---|---|---|---|---|---|---|
| hvH1 | R* | L* | I* | A* | M* | A* | K* | N* | A | V* | A* | F* | T* | 79.6 |
| hvH2 | G | L* | I* | V | M* | A* | K* | N* | A | V* | A* | F* | T* | 88.8 |
| hvH3 | G | L* | I* | A* | M* | A* | K* | N* | A | V* | A* | F* | T* | 86.7 |
| hvH4 | G | V | I* | A* | M* | A* | K* | N* | A | V* | A* | F* | T* | 88.8 |
| hvH5 | G | V | I* | A* | M | A* | K* | N* | A* | V* | A | F* | T* | 78.6 |
| hvH6 | R* | L* | I* | V | M | A* | K* | N* | A* | V* | A | F* | T* | 85.7 |

*Rat residues

TABLE 5

Specific Framework Mutations in hSG16.17 Kappa Light Chain Variants

| Variant | L40 | L46 | L48 | L78 | L85 | L87 | % Human |
|---|---|---|---|---|---|---|---|
| hvK2 | P | V* | V* | L | T | F* | 86.3 |
| hvK3 | P | V* | V* | L | T | F* | 87.4 |
| hvK4 | P | V* | V* | M* | D* | F* | 83.2 |
| hvK5 | S* | V* | V* | L | T | F* | 86.3 |

*Rat residues

The rat heavy and light chain variable regions of the rat hybridoma expressing SG16.17 were sequenced. HV1-2/HJ3 (SEQ ID NO: 9) or HV1-46/HJ3 (SEQ ID NO: 10) was used as the human acceptor sequence for the heavy chain and KV1-12/KJ5 (SEQ ID NO: 18) was used as the human acceptor sequence for the light chain.

Positions differing between rat donor and human acceptor sequences included H8, H20, H48, H67, H69, H71, H76, H78, H80, H88, H91, H93, L40, L46, L48, L78, L85 and L87. Different permutations of these residues were included as back mutations in different humanized heavy chain and light chain sequences. Several rat residues in the Kabat CDRs were also tested for replacement with corresponding residues of the human acceptor sequences. The positions of these residues were H34, H50, H58, H60, H61, H62, H64 and H65, and L24 and L53. Six humanized heavy chain variants and four humanized light chain variants were designed and expressed. Tables 2 and 3 indicate the human acceptor sequence, back mutations (donor framework residues), and CDR substitutions (Acceptor CDR residues) in each humanized variant chain. Tables 4 and 5 indicate the amino acids occupying each of the positions considered for back mutation in each of the humanized variant chain. These tables also indicate the percent of residue identical to the closest human germline sequence. According to recent INN Guidelines only antibodies with at least 85% identity to a human germline sequence in both heavy and light chains can be referred to as humanized. FIGS. 7-9 show alignments of humanized heavy chain variable regions with the rat variable region and human acceptor sequences. FIGS. 10 and 11 show alignment of the humanized light chain variable regions with the rat variable region and human acceptor sequences. The C-terminal arginine (R) of the variable light chains can alternatively be regarded as the N-terminal arginine of the light chain constant region.

The six humanized heavy chains and four humanized light chains were tested in all 24 possible permutations for binding to BCMA expressed on NCI-H929 cells, which express about 50,000 molecules of BCMA per cell. The results are shown in Table 6 below. In brief, all of the humanized light chains showed good binding. Of the humanized heavy chains, variants VH1, VH3 and VH5 all showed improved binding compared with either chimeric or rat SG16.17 antibody.

TABLE 6

Humanized Antibodies hSG16.17 Binding to BCMA Expressed on NCI-H929 Cells

| hSG16.17 | vH | vK | NCI-H929 3-pt Assay |
|---|---|---|---|
| 1 | vH1 | vK2 | ++++ |
| 2 | vH1 | vK3 | ++++ |
| 3 | vH1 | vK4 | ++++ |
| 4 | vH1 | vK5 | ++++ |
| 5 | vH2 | vK2 | − |
| 6 | vH2 | vK3 | − |
| 7 | vH2 | vK4 | − |
| 8 | vH2 | vK5 | − |
| 9 | vH3 | vK2 | ++++ |
| 10 | vH3 | vK3 | ++++ |
| 11 | vH3 | vK4 | ++++ |
| 12 | vH3 | vK5 | ++++ |
| 13 | vH4 | vK2 | − |
| 14 | vH4 | vK3 | − |
| 15 | vH4 | vK4 | − |
| 16 | vH4 | vK5 | − |
| 17 | vH5 | vK2 | ++++ |
| 18 | vH5 | vK3 | ++++ |
| 19 | vH5 | vK4 | ++++ |
| 20 | vH5 | vK5 | ++++ |
| 21 | vH6 | vK2 | ++ |
| 22 | vH6 | vK3 | ++ |
| 23 | vH6 | vK4 | ++ |
| 24 | vH6 | vK5 | ++ |
| cSG16.17 | | | +++ |
| rSG16.17 | | | +++ |

The humanized antibodies performing best on the NCI-H929 assay (i.e., those containing VH1, VH3 or VH5 heavy chains, were further tested for binding to U266 cells at a full range of concentration points. In this assay, humanized antibodies containing VH1 heavy chains (regardless of which humanized light chain variant was included) showed enhanced binding relative to rat or chimeric SG16.17. Humanized antibodies containing VH3 or VH5 heavy chains (regardless of which humanized light chain variant was included) showed the same binding within experimental error as rat or chimeric SG16.17 binding. Humanized antibodies containing VH2 or VH6 variable regions showed reduced binding relative to rat or chimeric SG16.17 regardless of which humanized light chain variant was included.

The humanized antibodies performing best on the NCI-H929 assay were also compared for protein expression level, monomer level and percentage sequence identity to human germ line as shown in Table 7 below.

TABLE 7

| hSG16.17 | vH | vK | hBCMA Binding | Transient Titer (mg/L) | aSEC (% Monomer) | ≥85% human (vH, vK) & INN Designation | | Lead Selection |
|---|---|---|---|---|---|---|---|---|
| 1 | vH1 | vK2 | ++++ | 139 | 90.4 | 79.6 | 86.3 Mix | Y |
| 2 | vH1 | vK3 | ++++ | 126 | 89.6 | 79.6 | 87.4 Mix | Y |
| 3 | vH1 | vK4 | ++++ | 80 | 94.6 | 79.6 | 83.2 Chimeric | N |
| 4 | vH1 | vK5 | ++++ | 119 | 89.5 | 79.6 | 86.3 Mix | N |
| 9 | vH3 | vK2 | ++++ | 129 | 94.1 | 86.7 | 86.3 Humanized | Y |
| 10 | vH3 | vK3 | ++++ | 116 | 94.1 | 86.7 | 87.4 Humanized | Y |
| 11 | vH3 | vK4 | ++++ | 82 | 95.2 | 86.7 | 83.2 Mix | Y |
| 12 | vH3 | vK5 | ++++ | 117 | 93.5 | 86.7 | 86.3 Humanized | Y |

TABLE 7-continued

| hSG16.17 | vH | vK | hBCMA Binding | Transient Titer (mg/L) | aSEC (% Monomer) | ≥85% human (vH, vK) & INN Designation | | Lead Selection |
|---|---|---|---|---|---|---|---|---|
| 17 | vH5 | vK2 | ++++ | 97 | 96.2 | 78.6 86.3 | Mix | Y |
| 18 | vH5 | vK3 | ++++ | 86 | 96.1 | 78.6 87.4 | Mix | Y |
| 19 | vH5 | vK4 | ++++ | 65 | 96.5 | 78.6 83.2 | Chimeric | N |
| 20 | vH5 | vK5 | ++++ | 73 | 95.0 | 78.6 86.3 | Mix | Y |

The VH3 VK2 humanized antibody was selected as the lead humanized antibody based on it having the same binding affinity for human BCMA as rat and mouse SG16.17 antibodies (within experimental error); greater than 85% identity to human germline sequence in both heavy and light chain variable regions, good expression and high percentage of monomers.

Example 7: Humanization of SG16.45

TABLE 8

Humanizing Mutations in hSG16.45 Heavy Chain Variants

| vH Variant | HV Exon Acceptor Sequence | Donor Framework Residues | Acceptor CDR Residues |
|---|---|---|---|
| hvH1 | HV3-23/HJ3 | H30, H37, H48, H93, H94, H107 | none |
| hvH2 | HV3-23/HJ3 | H30, H37, H48, H93, H94, H107 | H50, H60 |
| hvH3 | HV3-23/HJ3 | H30, H37, H48, H76, H93, H94, H107 | H50, H60 |
| hvH4 | HV3-23/HJ3 | H30, H48, H76, H93, H94 | H50 |
| hvH5 | HV3-74/HJ3 | H30, H93, H94 | H50 |
| hvH6 | HV3-9/HJ3 | H30, H93, H94 | H50, H60 |

TABLE 9

Humanizing Mutations in hSG16.45 Kappa Light Chain Variants

| vK Variant | KV Exon Acceptor Sequence | Donor Framework Residues | Acceptor CDR Residues |
|---|---|---|---|
| hvK1 | KV3-20/KJ2 | L14, L19, L21. L38, L58, L71, L78 | L24, L26 |
| hvK2 | KV3-20/KJ2 | none | L24, L26 |
| hvK3 | KV3-20/KJ2 | L21, L38, L58, L71 | L24, L26 |
| hvK5 | KV3-20/KJ2 | L38, L71 | none |

TABLE 10

Specific Framework Mutations in hSG16.45 Heavy Chain Variants

| Variant | H30 | H37 | H48 | H76 | H93 | H94 | H107 | % Human |
|---|---|---|---|---|---|---|---|---|
| hvH1 | N* | I* | I* | N | T* | S* | V* | 86.5 |
| hvH2 | N* | I* | I* | N | T* | S* | V* | 88.5 |
| hvH3 | N* | I* | I* | S* | T* | S* | V* | 87.5 |
| hvH4 | N* | V | I* | S* | T* | S* | T | 87.5 |
| hvH5 | N* | V | V | N | T* | S* | T | 88.5 |
| hvH6 | N* | V | V | N | T* | S* | T | 88.5 |

*Rat residues

TABLE 11

Specific Framework Mutations in hSG16.45 Kappa Light Chain Variants

| Variant | L14 | L19 | L21 | L38 | L58 | L71 | L78 | % Human |
|---|---|---|---|---|---|---|---|---|
| hvK1 | A* | V* | I* | H* | V* | Y* | M* | 79.2 |
| hvK2 | L | A | L | Q | I | F | L | 86.5 |
| hvK3 | L | A | I* | H* | V* | Y* | L | 82.3 |
| hvK5 | L | A | L | H* | I | Y* | L | 82.3 |

*Rat residues

The rat heavy and light chain variable regions of the rat hybridoma expressing SG16.45 were sequenced. HV3-23/HJ3 (SEQ ID NO: 24) was used as the human acceptor sequence for the heavy chain and KV3-20/KJ2 (SEQ ID NO: 34) was used as the human acceptor sequence for the light chain.

Variable region framework positions differing between rat donor and human acceptor sequences included H30, H37, H48, H67, H93, H94 and H107 and positions L14, L19, L21, L38, L58, L71 and L78. Different permutations of these residues were included as back mutations in different humanized heavy chain and light chain sequences. Several rat residues in the Kabat CDRs were also tested for replacement with corresponding residues of the human acceptor sequences. The positions of these residues were H50, H60, L24 and L26. Six humanized heavy chain variants and four humanized light chain variants were designed and expressed. Tables 8 and 9 indicate the human acceptor sequence, back mutations (donor framework residues), and CDR substitutions (Acceptor CDR residues) in each humanized variant chain. Tables 10 and 11 indicate the amino acids occupying each of the positions considered for back mutation in each of the humanized variant chain. These tables also indicate the percent of residue identical to the closest human germline sequence. According to recent INN Guidelines only antibodies with at least 85% identity to a human germline sequence in both heavy and light chains can be referred to as humanized. FIGS. 14-17 show an alignment of humanized heavy chain variable regions with the rat variable region and human acceptor sequences. FIGS. 18 and 19 show alignments of the light chain variable regions. The C-terminal arginine (R) of the variable light chains can alternatively be regarded as the N-terminal arginine of the light chain constant region.

The six humanized heavy chains and four humanized light chains were tested in all 24 possible permutations for binding to BCMA expressed on NCI-H929 cells, which express about 50,000 molecules of BCMA per cell. The results are shown in Table 12 below.

TABLE 12

Humanized Antibodies hSG16.45 Binding to BCMA Expressed on NCI-H929 Cells

| hSG16.45 | vH | vK | NCI-H929 3-pt Assay |
|---|---|---|---|
| 1 | vH1 | vK1 | +++ |
| 2 | vH1 | vK2 | +++ |
| 3 | vH1 | vK3 | +++ |
| 4 | vH1 | vK5 | +++ |
| 5 | vH2 | vK1 | − |
| 6 | vH2 | vK2 | − |
| 7 | vH2 | vK3 | − |
| 8 | vH2 | vK5 | − |
| 9 | vH3 | vK1 | − |
| 10 | vH3 | vK2 | − |
| 11 | vH3 | vK3 | − |
| 12 | vH3 | vK5 | ++ |
| 13 | vH4 | vK1 | + |
| 14 | vH4 | vK2 | + |
| 15 | vH4 | vK3 | + |
| 16 | vH4 | vK5 | ++ |
| 17 | vH5 | vK1 | ++ |
| 18 | vH5 | vK2 | ++ |
| 19 | vH5 | vK3 | ++ |
| 20 | vH5 | vK5 | ++ |
| 21 | vH6 | vK1 | + |
| 22 | vH6 | vK2 | + |
| 23 | vH6 | vK3 | + |
| 24 | vH6 | vK5 | ++ |
| cSG16.45 | | | +++ |
| rSG16.45 | | | +++ |

The humanized antibodies performing best on the NCI-H929 assay, were further tested for binding to U266 cells at a full range of concentration points, as well as for expression and monomer content, as well as sequence identity to human germline (Table 13).

TABLE 13

| hSG16.45 | VH | VK | hBCMA | IgG mg | aSEC % | VH % | VK % | INN |
|---|---|---|---|---|---|---|---|---|
| 1 | VH1 | VK1 | +++ | 0.67 | 94.5 | 86.5 | 79.2 | Mix |
| 3 | VH1 | VK3 | +++ | 0.54 | 94.6 | 86.5 | 82.3 | Mix |
| 4 | VH1 | VK5 | +++ | 0.16 | 76.0 | 86.5 | 82.3 | Mix |
| 17 | VH5 | VK1 | ++ | 0.64 | 94.4 | 88.5 | 79.2 | Mix |
| 18 | VH5 | VK2 | ++ | 0.65 | 93.7 | 88.5 | 86.5 | Hu |
| 19 | VH5 | VK3 | ++ | 0.64 | 94.1 | 88.5 | 82.3 | Mix |

The VH5 VK2, VH1 VK1 and VH1 VK3 were the best antibodies overall based on binding affinity for human, sequence identity to human germline sequence in both heavy and light chain variable regions, good expression and high percentage of monomers VH1 VK1 and VH1 VK3 have somewhat higher binding (the same as rat or chimeric within experimental error) but lower sequence identity to human germline.

Example 8: Synthesis of a Reduced-Fucosylated hSG16.17 or hSG16.45 Antibody

The hSG16.17 VH3 VK2 or hSG16.45 VH5 VK2 antibody was expressed in CHO cells. A fucosylation inhibitor, 2-fluorofucose, was included in the cell culture media during the production of antibodies resulted in non-fucosylated antibody. See, e.g., Okeley et al., Proc. Nat'l Acad. Sci. 110:5404-55409 (2013). The base media for cell growth was fucose free and 2-flurofucose was added to the media to inhibit protein fucosylation. Ibid. Incorporation of fucose into antibodies was measured by LC-MS via PLRP-S chromatography and electrospray ionization quadrople TOF MS. Ibid.

Example 9: In Vivo Activity of hSG16.17-SEA in SCID or NSG Mice

Figure 20A:
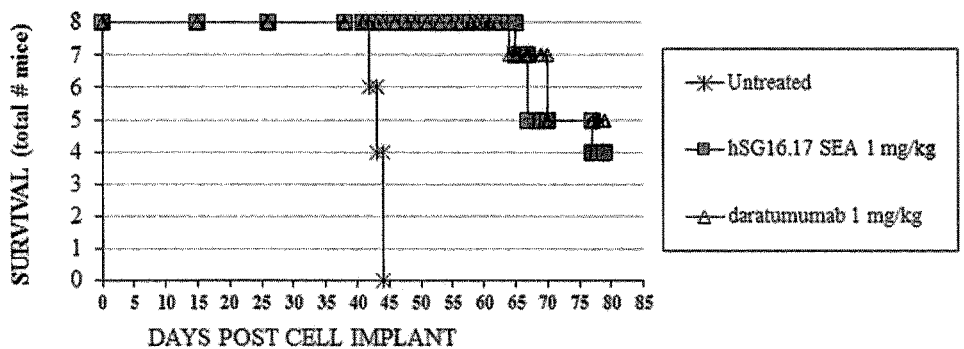
FIGS. 20A-C show in vivo activity of multi dosed hSG16.17-SEA in MM1S disseminated tumor model in SCID mice.
Figure 20B:
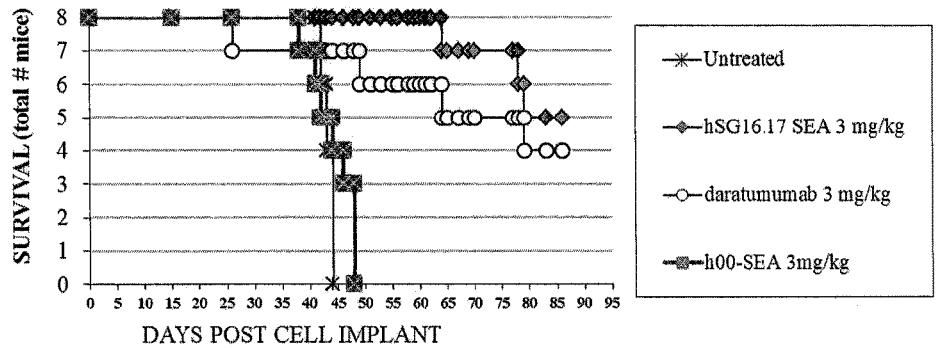
Figure 20C:
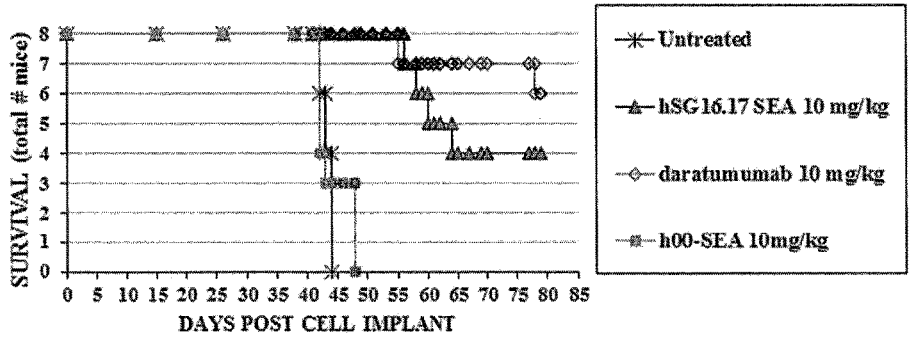

FIGS. 20A-C showed in vivo activity of multi dosed hSG16.17-SEA in MM1S disseminated tumor model in SCID mice. Animals were implanted with MM1S cells IV, and antibody dosing was initiated 9 days post implant. Animal survival was followed over time. N=8 animals per group. BCMA copy #=7,000, CD38 copy #=14,000. A) 1 mg/kg weekly ip for 5 weeks B) 3 mg/kg weekly ip for 5 weeks and C) 10 mg/kg weekly ip for 5 weeks. SCID animals contain effector cells to mediate ADCC and ADCP. Data in this figure show that hSG16.17 SEA improves survival comparable to daratumumab (CD38 targeted Ab. Non-binding h00 control showed no activity.

Figure 21A:
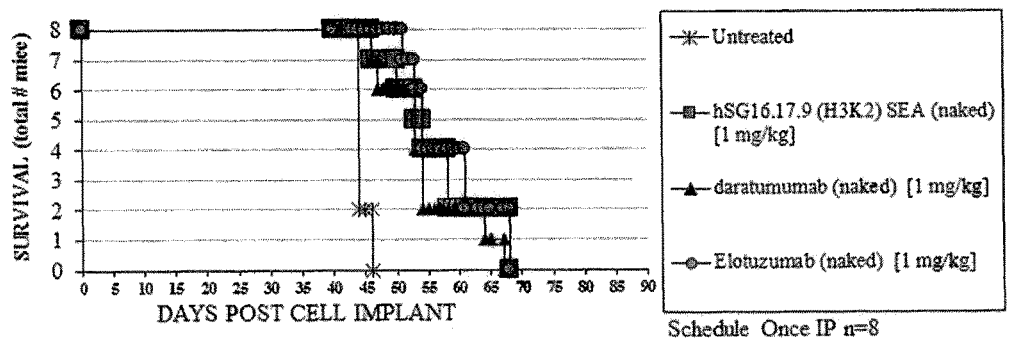
FIGS. 21A-C show in vivo activity of single dosed hSG16.17-SEA in EJM disseminated tumor model in NSG mice.
Figure 21B:
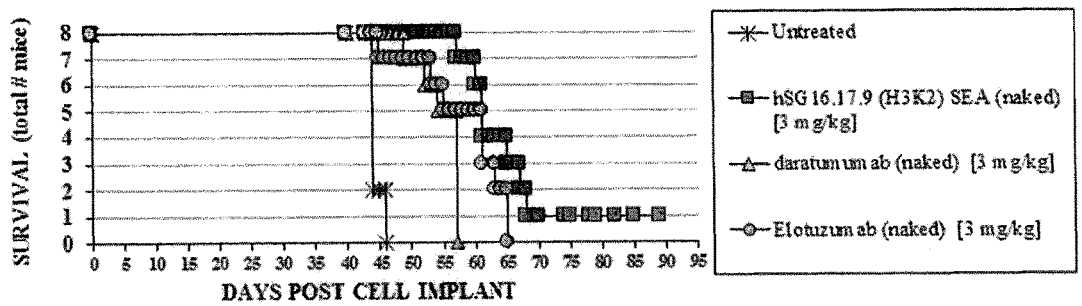
Figure 21C:
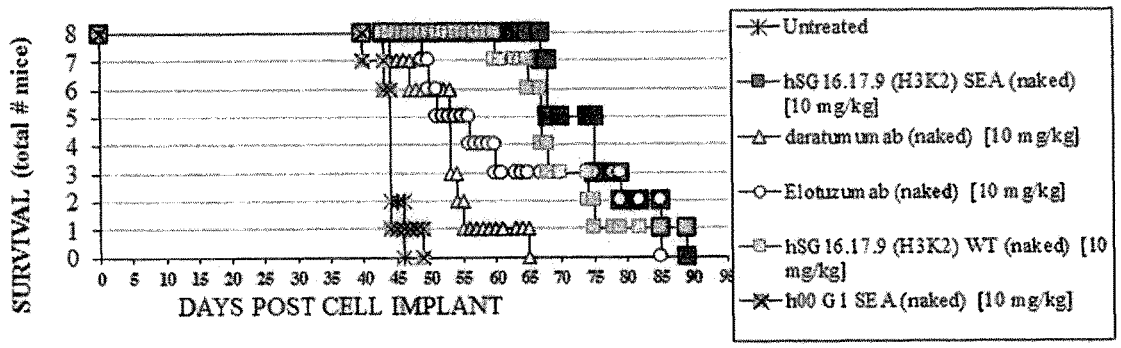

FIGS. 21A-C showed In vivo activity of single dosed hSG16.17-SEA in EJM disseminated tumor model in NSG mice. NSG animals contain no NK cells and minimally active macrophages Animals were implanted with EJM cells IV, and a single dose of antibody was given ip 5 days post implant. Animal survival was followed over time. N=8 animals per group. BCMA copy #=45,000. CD38 copy #=47,000. CS1 copy #=14,000. A) 1 mg/kg dose B) 3 mg/kg dose C) 10 mg/kg dose. Data in this figure show that hSG16.17 SEA increases survival to an equal or greater extent than daratumumab (CD38 targeted Ab) and elotuzumab (CS1 targeted Ab). WT SG16.17 can also induce increased survival. Non-binding h00 control showed no activity at the highest dose. Since there are minimal effector cells in these animals, activity of WT and SEA hSG16.17 antibodies is likely due to blocking of the APRIL and BAFF proliferation signals.

FIG. 22 showed in vivo activity of multi dosed hSG16.17-SEA in NCI-H929-luciferase disseminated tumor model in NSG mice. NSG animals were implanted with NCI-H929 luciferase cells. Antibody dosing was initiated 21 days post implant when bioluminescence was observed in the bone marrow. Dosed ip weekly for 5 doses total. N=5 animals per group. BCMA copy #=25,000. CD38 copy #=45,000. CS1 copy #=3,000. Average luminescence is plotted over time in comparison to untreated and naïve animals. hSG16.17 SEA displayed much better activity compared to daratumumab (CD38 targeted Ab) and elotuzumab (CS1 targeted Ab). The increased luminescence observed in the hSG16.17-SEA 10 mg/kg group is driven by a single animal.

Figure 23A:
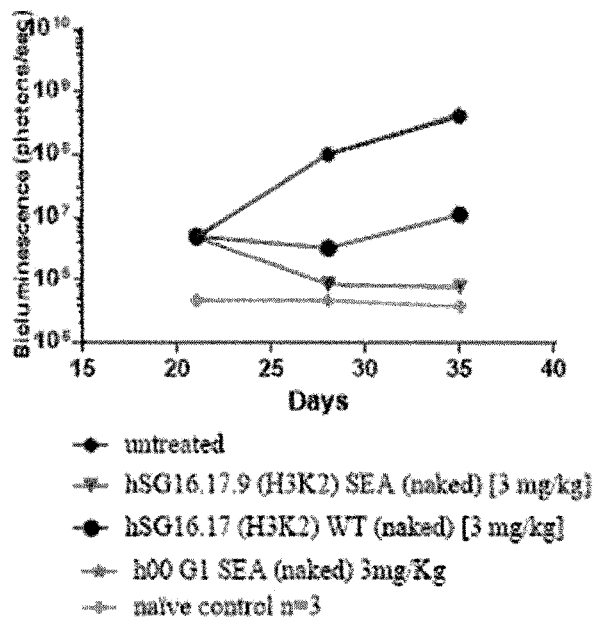
FIGS. 23A-B show in vivo activity of single dosed hSG16.17-SEA in NCI-H929-luciferase disseminated tumor model in NSG mice.
Figure 23B:
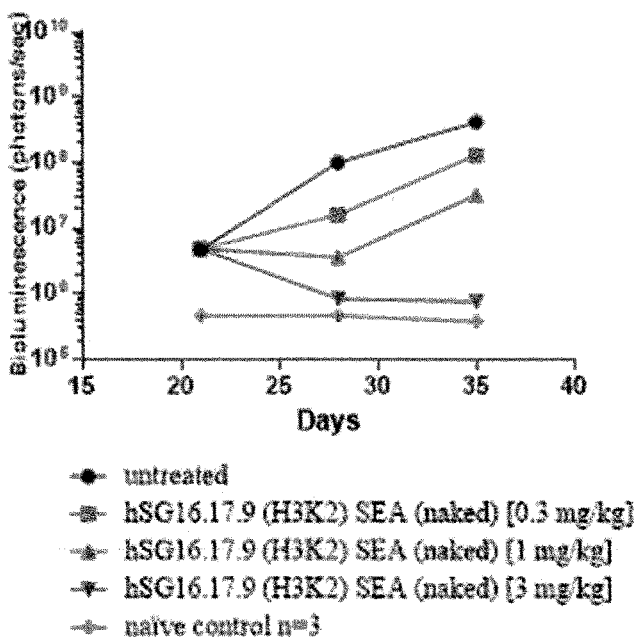

FIGS. 23A and 23B showed in vivo activity of single dosed hSG16.17-SEA in NCI-H929-luciferase disseminated tumor model in NSG mice. NSG animals were implanted with NCI-H929 luciferase cells. Antibody dosing was initiated 21 days post injection when bioluminescence was observed in the bone marrow. Dosed once IP. N=5 animals per group. A) 3 mg/kg WT vs SEA antibodies. B) Dose range of hSG16.17 SEA. Data in this figure show that hSG16.17

SEA can be active at 0.3 mg/kg single dose and hSG16.17SEA can be more active than its WT (fucosylated) counterpart.

FIGS cttggtttca tgattaaact cttttttttc ctga                                     994

<210> SEQ ID NO 2
<211> LENGTH: 184
<212> TYPE: PRT
<213> ORGANISM: Homo sapiens

<400> SEQUENCE: 2

Met Leu Gln Met Ala Gly Gln Cys Ser Gln Asn Glu Tyr Phe Asp Ser
1               5                   10                  15

Leu Leu His Ala Cys Ile Pro Cys Gln Leu Arg Cys Ser Ser Asn Thr
            20                  25                  30

Pro Pro Leu Thr Cys Gln Arg Tyr Cys Asn Ala Ser Val Thr Asn Ser
        35                  40                  45

Val Lys Gly Thr Asn Ala Ile Leu Trp Thr Cys Leu Gly Leu Ser Leu
    50                  55                  60

Ile Ile Ser Leu Ala Val Phe Val Leu Met Phe Leu Leu Arg Lys Ile
65                  70                  75                  80

Asn Ser Glu Pro Leu Lys Asp Glu Phe Lys Asn Thr Gly Ser Gly Leu
                85                  90                  95

Leu Gly Met Ala Asn Ile Asp Leu Glu Lys Ser Arg Thr Gly Asp Glu
            100                 105                 110

Ile Ile Leu Pro Arg Gly Leu Glu Tyr Thr Val Glu Glu Cys Thr Cys
        115                 120                 125

Glu Asp Cys Ile Lys Ser Lys Pro Lys Val Asp Ser Asp His Cys Phe
    130                 135                 140

Pro Leu Pro Ala Met Glu Gly Ala Thr Ile Leu Val Thr Thr Lys
145                 150                 155                 160

Thr Asn Asp Tyr Cys Lys Ser Leu Pro Ala Ala Leu Ser Ala Thr Glu
                165                 170                 175

Ile Glu Lys Ser Ile Ser Ala Arg
            180

<210> SEQ ID NO 3
<211> LENGTH: 106
<212> TYPE: PRT
<213> ORGANISM: homo sapiens

<400> SEQUENCE: 3

Thr Val Ala Ala Pro Ser Val Phe Ile Phe Pro Pro Ser Asp Glu Gln
1               5                   10                  15

Leu Lys Ser Gly Thr Ala Ser Val Val Cys Leu Leu Asn Asn Phe Tyr
            20                  25                  30

Pro Arg Glu Ala Lys Val Gln Trp Lys Val Asp Asn Ala Leu Gln Ser
        35                  40                  45

Gly Asn Ser Gln Glu Ser Val Thr Glu Gln Asp Ser Lys Asp Ser Thr
    50                  55                  60

Tyr Ser Leu Ser Ser Thr Leu Thr Leu Ser Lys Ala Asp Tyr Glu Lys
65                  70                  75                  80

His Lys Val Tyr Ala Cys Glu Val Thr His Gln Gly Leu Ser Ser Pro
                85                  90                  95

Val Thr Lys Ser Phe Asn Arg Gly Glu Cys
            100                 105

<210> SEQ ID NO 4
<211> LENGTH: 330
<212> TYPE: PRT

<213> ORGANISM: homo sapiens

<400> SEQUENCE: 4

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 5
<211> LENGTH: 329
<212> TYPE: PRT
<213> ORGANISM: homo sapiens

<400> SEQUENCE: 5

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr

```
            20                  25                  30
Phe Pro Glu Pro Val Thr Val Ser Trp Asn Ser Gly Ala Leu Thr Ser
        35                  40                  45
Gly Val His Thr Phe Pro Ala Val Leu Gln Ser Ser Gly Leu Tyr Ser
 50                  55                  60
Leu Ser Ser Val Val Thr Val Pro Ser Ser Ser Leu Gly Thr Gln Thr
 65                  70                  75                  80
Tyr Ile Cys Asn Val Asn His Lys Pro Ser Asn Thr Lys Val Asp Lys
                 85                  90                  95
Lys Val Glu Pro Lys Ser Cys Asp Lys Thr His Thr Cys Pro Pro Cys
             100                 105                 110
Pro Ala Pro Glu Leu Leu Gly Gly Pro Ser Val Phe Leu Phe Pro Pro
         115                 120                 125
Lys Pro Lys Asp Thr Leu Met Ile Ser Arg Thr Pro Glu Val Thr Cys
     130                 135                 140
Val Val Val Asp Val Ser His Glu Asp Pro Glu Val Lys Phe Asn Trp
145                 150                 155                 160
Tyr Val Asp Gly Val Glu Val His Asn Ala Lys Thr Lys Pro Arg Glu
                165                 170                 175
Glu Gln Tyr Asn Ser Thr Tyr Arg Val Val Ser Val Leu Thr Val Leu
            180                 185                 190
His Gln Asp Trp Leu Asn Gly Lys Glu Tyr Lys Cys Lys Val Ser Asn
        195                 200                 205
Lys Ala Leu Pro Ala Pro Ile Glu Lys Thr Ile Ser Lys Ala Lys Gly
    210                 215                 220
Gln Pro Arg Glu Pro Gln Val Tyr Thr Leu Pro Pro Ser Arg Asp Glu
225                 230                 235                 240
Leu Thr Lys Asn Gln Val Ser Leu Thr Cys Leu Val Lys Gly Phe Tyr
                245                 250                 255
Pro Ser Asp Ile Ala Val Glu Trp Glu Ser Asn Gly Gln Pro Glu Asn
            260                 265                 270
Asn Tyr Lys Thr Thr Pro Pro Val Leu Asp Ser Asp Gly Ser Phe Phe
        275                 280                 285
Leu Tyr Ser Lys Leu Thr Val Asp Lys Ser Arg Trp Gln Gln Gly Asn
    290                 295                 300
Val Phe Ser Cys Ser Val Met His Glu Ala Leu His Asn His Tyr Thr
305                 310                 315                 320
Gln Lys Ser Leu Ser Leu Ser Pro Gly
                325

<210> SEQ ID NO 6
<211> LENGTH: 330
<212> TYPE: PRT
<213> ORGANISM: homo sapiens

<400> SEQUENCE: 6

Ala Ser Thr Lys Gly Pro Ser Val Phe Pro Leu Ala Pro Ser Ser Lys
1               5                  10                  15
Ser Thr Ser Gly Gly Thr Ala Ala Leu Gly Cys Leu Val Lys Asp Tyr
            20                  25                  30
Phe Pro Glu Pro Val Thr Val Ser Trp Asn Ser Gly Ala Leu Thr Ser
        35                  40                  45
Gly Val His Thr Phe Pro Ala Val Leu Gln Ser Ser Gly Leu Tyr Ser
    50                  55                  60
```

```
Leu Ser Ser Val Val Thr Val Pro Ser Ser Ser Leu Gly Thr Gln Thr
 65                  70                  75                  80

Tyr Ile Cys Asn Val Asn His Lys Pro Ser Asn Thr Lys Val Asp Lys
                 85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Cys Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 7
<211> LENGTH: 329
<212> TYPE: PRT
<213> ORGANISM: homo sapiens

<400> SEQUENCE: 7

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Ser Leu Gly Thr Gln Thr
 65                  70                  75                  80

Tyr Ile Cys Asn Val Asn His Lys Pro Ser Asn Thr Lys Val Asp Lys
                 85                  90                  95

Lys Val Glu Pro Lys Ser Cys Asp Lys Thr His Thr Cys Pro Pro Cys
            100                 105                 110
```

```
Pro Ala Pro Glu Leu Leu Gly Gly Pro Cys Val Phe Leu Phe Pro Pro
            115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
            195                 200                 205

Lys Ala Leu Pro Ala Pro Ile Glu Lys Thr Ile Ser Lys Ala Lys Gly
210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
            275                 280                 285

Leu Tyr Ser Lys Leu Thr Val Asp Lys Ser Arg Trp Gln Gln Gly Asn
            290                 295                 300

Val Phe Ser Cys Ser Val Met His Glu Ala Leu His Asn His Tyr Thr
305                 310                 315                 320

Gln Lys Ser Leu Ser Leu Ser Pro Gly
                325

<210> SEQ ID NO 8
<211> LENGTH: 121
<212> TYPE: PRT
<213> ORGANISM: Rattus norvegicus

<400> SEQUENCE: 8

Gln Val Asn Leu Leu Gln Ser Arg Ala Ala Leu Val Lys Pro Gly Ala
1               5                   10                  15

Ser Val Lys Leu Ser Cys Glu Ala Ser Gly Tyr Thr Phe Thr Asp Tyr
                20                  25                  30

Tyr Ile His Trp Val Lys Gln Ser His Gly Lys Ser Leu Glu Trp Ile
            35                  40                  45

Gly Tyr Ile Asn Pro Asn Ser Gly Tyr Thr Lys Tyr Asn Glu Asn Phe
        50                  55                  60

Lys Thr Lys Ala Thr Met Thr Ala Asp Lys Ser Thr Asn Thr Ala Tyr
65                  70                  75                  80

Val Glu Leu Ser Arg Leu Thr Ser Glu Asp Ser Ala Thr Tyr Phe Cys
                85                  90                  95

Thr Arg Tyr Met Trp Glu Arg Val Thr Gly Phe Phe Asp Phe Trp Gly
            100                 105                 110

Pro Gly Thr Lys Val Thr Val Ser Ser
            115                 120

<210> SEQ ID NO 9
<211> LENGTH: 109
<212> TYPE: PRT
```

<213> ORGANISM: homo sapiens

<400> SEQUENCE: 9

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Tyr Met His Trp Val Arg Gln Ala Pro Gly Gln Gly Leu Glu Trp Met
        35                  40                  45

Gly Arg Ile Asn Pro Asn Ser Gly Thr Asn Tyr Ala Gln Lys Phe
    50                  55                  60

Gln Gly Arg Val Thr Ser Thr Arg Asp Thr Ser Ile Ser Thr Ala Tyr
65                  70                  75                  80

Met Glu Leu Ser Arg Leu Arg Ser Asp Asp Thr Val Val Tyr Tyr Cys
                85                  90                  95

Ala Arg Trp Gly Gln Gly Thr Met Val Thr Val Ser Ser
            100                 105

<210> SEQ ID NO 10
<211> LENGTH: 109
<212> TYPE: PRT
<213> ORGANISM: homo sapiens

<400> SEQUENCE: 10

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Tyr Met His Trp Val Arg Gln Ala Pro Gly Gln Gly Leu Glu Trp Met
        35                  40                  45

Gly Ile Ile Asn Pro Ser Gly Gly Ser Thr Ser Tyr Ala Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Trp Gly Gln Gly Thr Met Val Thr Val Ser Ser
            100                 105

<210> SEQ ID NO 11
<211> LENGTH: 121
<212> TYPE: PRT
<213> ORGANISM: Artificial Sequence
<220> FEATURE:
<223> OTHER INFORMATION: hSG16.17 vH1

<400> SEQUENCE: 11

Gln Val Gln Leu Val Gln Ser Arg Ala Glu Val Lys Lys Pro Gly Ala
1               5                   10                  15

Ser Val Lys Leu Ser Cys Lys Ala Ser Gly Tyr Thr Phe Thr Asp Tyr
            20                  25                  30

Tyr Ile His Trp Val Arg Gln Ala Pro Gly Gln Gly Leu Glu Trp Ile
        35                  40                  45

Gly Tyr Ile Asn Pro Asn Ser Gly Tyr Thr Lys Tyr Asn Glu Asn Phe
    50                  55                  60

Lys Thr Arg Ala Thr Met Thr Ala Asp Lys Ser Ile Asn Thr Ala Tyr
65                  70                  75                  80

-continued

```
Val Glu Leu Ser Arg Leu Arg Ser Asp Asp Thr Ala Val Tyr Phe Cys
                85                  90                  95

Thr Arg Tyr Met Trp Glu Arg Val Thr Gly Phe Phe Asp Phe Trp Gly
            100                 105                 110

Gln Gly Thr Met Val Thr Val Ser Ser
        115                 120

<210> SEQ ID NO 12
<211> LENGTH: 121
<212> TYPE: PRT
<213> ORGANISM: Artificial Sequence
<220> FEATURE:
<223> OTHER INFORMATION: hSG16.17 vH2

<400> SEQUENCE: 12

Gln Val Gln Leu Val Gln Ser Gly Ala Glu Val Lys Lys Pro Gly Ala
1               5                   10                  15

Ser Val Lys Leu Ser Cys Lys Ala Ser Gly Tyr Thr Phe Thr Asp Tyr
            20                  25                  30

Tyr Met His Trp Val Arg Gln Ala Pro Gly Gln Gly Leu Glu Trp Ile
        35                  40                  45

Gly Arg Ile Asn Pro Asn Ser Gly Tyr Thr Asn Tyr Ala Gln Lys Phe
    50                  55                  60

Gln Gly Arg Val Thr Met Thr Ala Asp Lys Ser Ile Asn Thr Ala Tyr
65                  70                  75                  80

Val Glu Leu Ser Arg Leu Arg Ser Asp Asp Thr Ala Val Tyr Phe Cys
                85                  90                  95

Thr Arg Tyr Met Trp Glu Arg Val Thr Gly Phe Phe Asp Phe Trp Gly
            100                 105                 110

Gln Gly Thr Met Val Thr Val Ser Ser
        115                 120

<210> SEQ ID NO 13
<211> LENGTH: 121
<212> TYPE: PRT
<213> ORGANISM: Artificial Sequence
<220> FEATURE:
<223> OTHER INFORMATION: hSG16.17 vH3

<400> SEQUENCE: 13

Gln Val Gln Leu Val Gln Ser Gly Ala Glu Val Lys Lys Pro Gly Ala
1               5                   10                  15

Ser Val Lys Leu Ser Cys Lys Ala Ser Gly Tyr Thr Phe Thr Asp Tyr
            20                  25                  30

Tyr Ile His Trp Val Arg Gln Ala Pro Gly Gln Gly Leu Glu Trp Ile
        35                  40                  45

Gly Tyr Ile Asn Pro Asn Ser Gly Tyr Thr Asn Tyr Ala Gln Lys Phe
    50                  55                  60

Gln Gly Arg Ala Thr Met Thr Ala Asp Lys Ser Ile Asn Thr Ala Tyr
65                  70                  75                  80

Val Glu Leu Ser Arg Leu Arg Ser Asp Asp Thr Ala Val Tyr Phe Cys
                85                  90                  95

Thr Arg Tyr Met Trp Glu Arg Val Thr Gly Phe Phe Asp Phe Trp Gly
            100                 105                 110

Gln Gly Thr Met Val Thr Val Ser Ser
        115                 120

<210> SEQ ID NO 14
```

```
<211> LENGTH: 121
<212> TYPE: PRT
<213> ORGANISM: Artificial Sequence
<220> FEATURE:
<223> OTHER INFORMATION: hSG16.17 vH4

<400> SEQUENCE: 14

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
                20                  25                  30

Tyr Met His Trp Val Arg Gln Ala Pro Gly Gln Gly Leu Glu Trp Ile
            35                  40                  45

Gly Arg Ile Asn Pro Asn Ser Gly Tyr Thr Asn Tyr Ala Gln Lys Phe
        50                  55                  60

Gln Gly Arg Ala Thr Met Thr Ala Asp Lys Ser Ile Asn Thr Ala Tyr
65                  70                  75                  80

Val Glu Leu Ser Arg Leu Arg Ser Asp Asp Thr Ala Val Tyr Phe Cys
                85                  90                  95

Thr Arg Tyr Met Trp Glu Arg Val Thr Gly Phe Phe Asp Phe Trp Gly
                100                 105                 110

Gln Gly Thr Met Val Thr Val Ser Ser
            115                 120

<210> SEQ ID NO 15
<211> LENGTH: 121
<212> TYPE: PRT
<213> ORGANISM: Artificial Sequence
<220> FEATURE:
<223> OTHER INFORMATION: hSG16.17 vH5

<400> SEQUENCE: 15

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
                20                  25                  30

Tyr Ile His Trp Val Arg Gln Ala Pro Gly Gln Gly Leu Glu Trp Ile
            35                  40                  45

Gly Tyr Ile Asn Pro Asn Ser Gly Tyr Thr Lys Tyr Asn Glu Asn Phe
        50                  55                  60

Lys Thr Arg Ala Thr Met Thr Ala Asp Lys Ser Thr Asn Thr Ala Tyr
65                  70                  75                  80

Val Glu Leu Ser Ser Leu Arg Ser Glu Asp Thr Ala Val Tyr Phe Cys
                85                  90                  95

Thr Arg Tyr Met Trp Glu Arg Val Thr Gly Phe Phe Asp Phe Trp Gly
                100                 105                 110

Gln Gly Thr Met Val Thr Val Ser Ser
            115                 120

<210> SEQ ID NO 16
<211> LENGTH: 121
<212> TYPE: PRT
<213> ORGANISM: Artificial Sequence
<220> FEATURE:
<223> OTHER INFORMATION: hSG16.17 vH6

<400> SEQUENCE: 16

Gln Val Gln Leu Val Gln Ser Arg Ala Glu Val Lys Lys Pro Gly Ala
1               5                   10                  15
```

Ser Val Lys Leu Ser Cys Lys Ala Ser Gly Tyr Thr Phe Thr Asp Tyr
            20                  25                  30

Tyr Met His Trp Val Arg Gln Ala Pro Gly Gln Gly Leu Glu Trp Ile
        35                  40                  45

Gly Ile Ile Asn Pro Asn Ser Gly Tyr Thr Ser Tyr Ala Gln Lys Phe
50                  55                  60

Gln Gly Arg Val Thr Met Thr Ala Asp Lys Ser Thr Asn Thr Ala Tyr
65                  70                  75                  80

Val Glu Leu Ser Ser Leu Arg Ser Glu Asp Thr Ala Val Tyr Phe Cys
                85                  90                  95

Thr Arg Tyr Met Trp Glu Arg Val Thr Gly Phe Phe Asp Phe Trp Gly
            100                 105                 110

Gln Gly Thr Met Val Thr Val Ser Ser
            115                 120

<210> SEQ ID NO 17
<211> LENGTH: 108
<212> TYPE: PRT
<213> ORGANISM: Rattus norvegicus

<400> SEQUENCE: 17

Asp Ile Gln Met Thr Gln Ser Pro Ala Ser Leu Ser Ala Ser Leu Gly
1               5                   10                  15

Glu Thr Val Ser Ile Glu Cys Leu Ala Ser Glu Asp Ile Ser Asp Asp
            20                  25                  30

Leu Ala Trp Tyr Gln Gln Lys Ser Gly Lys Ser Pro Gln Val Leu Val
        35                  40                  45

Tyr Thr Thr Ser Arg Leu Gln Asp Gly Val Pro Ser Arg Phe Ser Gly
    50                  55                  60

Ser Gly Ser Gly Thr Arg Phe Ser Leu Lys Ile Ile Val Met Gln Pro
65                  70                  75                  80

Glu Asp Glu Ala Asp Tyr Phe Cys Gln Gln Thr Tyr Lys Phe Pro Pro
                85                  90                  95

Thr Phe Gly Ala Gly Thr Arg Leu Asp Leu Lys Arg
            100                 105

<210> SEQ ID NO 18
<211> LENGTH: 106
<212> TYPE: PRT
<213> ORGANISM: homo sapiens

<400> SEQUENCE: 18

Asp Ile Gln Met Thr Gln Ser Pro Ser Ser Val Ser Ala Ser Val Gly
1               5                   10                  15

Asp Arg Val Thr Ile Thr Cys Arg Ala Ser Gln Gly Ile Ser Ser Trp
            20                  25                  30

Leu Ala Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ala Asn Ser Phe Pro Phe
                85                  90                  95

Gly Gly Gly Thr Lys Val Glu Ile Lys Arg
            100                 105

```
<210> SEQ ID NO 19
<211> LENGTH: 108
<212> TYPE: PRT
<213> ORGANISM: Artificial Sequence
<220> FEATURE:
<223> OTHER INFORMATION: hSG16.17 vK2

<400> SEQUENCE: 19

Asp Ile Gln Met Thr Gln Ser Pro Ser Ser Val Ser Ala Ser Val Gly
1               5                   10                  15

Asp Arg Val Thr Ile Thr Cys Leu Ala Ser Glu Asp Ile Ser Asp Asp
            20                  25                  30

Leu Ala Trp Tyr Gln Gln Lys Pro Gly Lys Ala Pro Lys Val Leu Val
        35                  40                  45

Tyr Thr Thr Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Phe Cys Gln Gln Thr Tyr Lys Phe Pro Pro
                85                  90                  95

Thr Phe Gly Gly Gly Thr Lys Val Glu Ile Lys Arg
            100                 105

<210> SEQ ID NO 20
<211> LENGTH: 108
<212> TYPE: PRT
<213> ORGANISM: Artificial Sequence
<220> FEATURE:
<223> OTHER INFORMATION: hSG16.17 vK3

<400> SEQUENCE: 20

Asp Ile Gln Met Thr Gln Ser Pro Ser Ser Val Ser Ala Ser Val Gly
1               5                   10                  15

Asp Arg Val Thr Ile Thr Cys Arg Ala Ser Glu Asp Ile Ser Asp Asp
            20                  25                  30

Leu Ala Trp Tyr Gln Gln Lys Pro Gly Lys Ala Pro Lys Val Leu Val
        35                  40                  45

Tyr Thr Thr Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Phe Cys Gln Gln Thr Tyr Lys Phe Pro Pro
                85                  90                  95

Thr Phe Gly Gly Gly Thr Lys Val Glu Ile Lys Arg
            100                 105

<210> SEQ ID NO 21
<211> LENGTH: 108
<212> TYPE: PRT
<213> ORGANISM: Artificial Sequence
<220> FEATURE:
<223> OTHER INFORMATION: hSG16.17 vK4

<400> SEQUENCE: 21

Asp Ile Gln Met Thr Gln Ser Pro Ser Ser Val Ser Ala Ser Val Gly
1               5                   10                  15

Asp Arg Val Thr Ile Thr Cys Leu Ala Ser Glu Asp Ile Ser Asp Asp
            20                  25                  30

Leu Ala Trp Tyr Gln Gln Lys Pro Gly Lys Ala Pro Lys Val Leu Val
```

```
            35                  40                  45

Tyr Thr Thr Ser Arg Leu Gln Ser Gly Val Pro Ser Arg Phe Ser Gly
        50                  55                  60

Ser Gly Ser Gly Thr Asp Phe Thr Leu Thr Ile Ser Ser Met Gln Pro
 65                  70                  75                  80

Glu Asp Phe Ala Asp Tyr Phe Cys Gln Gln Thr Tyr Lys Phe Pro Pro
                 85                  90                  95

Thr Phe Gly Gly Gly Thr Lys Val Glu Ile Lys Arg
            100                 105

<210> SEQ ID NO 22
<211> LENGTH: 108
<212> TYPE: PRT
<213> ORGANISM: Artificial Sequence
<220> FEATURE:
<223> OTHER INFORMATION: hSG16.17 vK5

<400> SEQUENCE: 22

Asp Ile Gln Met Thr Gln Ser Pro Ser Ser Val Ser Ala Ser Val Gly
  1               5                  10                  15

Asp Arg Val Thr Ile Thr Cys Arg Ala Ser Glu Asp Ile Ser Asp Asp
             20                  25                  30

Leu Ala Trp Tyr Gln Gln Lys Ser Gly Lys Ala Pro Lys Val Leu Val
         35                  40                  45

Tyr Thr Thr Ser Ser Leu Gln Ser Gly Val Pro Ser Arg Phe Ser Gly
     50                  55                  60

Ser Gly Ser Gly Thr Asp Phe Thr Leu Thr Ile Ser Ser Leu Gln Pro
 65                  70                  75                  80

Glu Asp Phe Ala Thr Tyr Phe Cys Gln Gln Thr Tyr Lys Phe Pro Pro
                 85                  90                  95

Thr Phe Gly Gly Gly Thr Lys Val Glu Ile Lys Arg
            100                 105

<210> SEQ ID NO 23
<211> LENGTH: 116
<212> TYPE: PRT
<213> ORGANISM: Rattus norvegicus

<400> SEQUENCE: 23

Glu Val Gln Leu Val Glu Ser Gly Gly Gly Leu Val Gln Pro Gly Arg
  1               5                  10                  15

Ser Leu Lys Leu Ser Cys Val Ala Ser Gly Phe Thr Phe Asn Asp His
             20                  25                  30

Trp Met Thr Trp Ile Arg Gln Ala Pro Gly Arg Gly Leu Glu Trp Ile
         35                  40                  45

Ser Ser Ile Thr Asn Thr Gly Gly Ala Thr Tyr Tyr Leu Asp Ser Val
     50                  55                  60

Lys Gly Arg Phe Thr Ile Ser Arg Asp Asn Ala Lys Ser Thr Leu Tyr
 65                  70                  75                  80

Leu Gln Met Asn Ser Leu Arg Ser Glu Asp Thr Ala Thr Tyr Tyr Cys
                 85                  90                  95

Thr Ser Pro Gly Leu Tyr Phe Asp Tyr Trp Gly Gln Gly Val Met Val
            100                 105                 110

Thr Val Ser Ser
        115

<210> SEQ ID NO 24
```

```
<211> LENGTH: 109
<212> TYPE: PRT
<213> ORGANISM: homo sapiens

<400> SEQUENCE: 24

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Asp His
            20                  25                  30

Trp Met Thr Trp Val Arg Gln Ala Pro Gly Lys Gly Leu Glu Trp Val
        35                  40                  45

Ser Ser Ile Thr Asn Thr Gly Gly Ala Thr Tyr Tyr Leu Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Trp Gly Gln Gly Thr Met Val Thr Val Ser Ser
            100                 105

<210> SEQ ID NO 25
<211> LENGTH: 109
<212> TYPE: PRT
<213> ORGANISM: homo sapiens

<400> SEQUENCE: 25

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asp His
            20                  25                  30

Trp Met Thr Trp Val Arg Gln Ala Pro Gly Lys Gly Leu Val Trp Val
        35                  40                  45

Ser Ser Ile Thr Asn Thr Gly Gly Ala Thr Tyr Tyr Leu Asp Ser Val
    50                  55                  60

Lys Gly Arg Phe Thr Ile Ser Arg Asp Asn Ala Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Trp Gly Gln Gly Thr Met Val Thr Val Ser Ser
            100                 105

<210> SEQ ID NO 26
<211> LENGTH: 109
<212> TYPE: PRT
<213> ORGANISM: homo sapiens

<400> SEQUENCE: 26

Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asp Asp His
            20                  25                  30

Trp Met Thr Trp Val Arg Gln Ala Pro Gly Lys Gly Leu Glu Trp Val
        35                  40                  45

Ser Ser Ile Thr Asn Thr Gly Gly Ala Thr Tyr Tyr Leu Asp Ser Val
    50                  55                  60

Lys Gly Arg Phe Thr Ile Ser Arg Asp Asn Ala Lys Asn Ser Leu Tyr
65                  70                  75                  80
```

Leu Gln Met Asn Ser Leu Arg Ala Glu Asp Thr Ala Leu Tyr Tyr Cys
            85                  90                  95

Ala Lys Trp Gly Gln Gly Thr Met Val Thr Val Ser Ser
            100                 105

<210> SEQ ID NO 27
<211> LENGTH: 116
<212> TYPE: PRT
<213> ORGANISM: Artificial Sequence
<220> FEATURE:
<223> OTHER INFORMATION: hSG16.45 vH1

<400> SEQUENCE: 27

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Asn Asp His
            20                  25                  30

Trp Met Thr Trp Ile Arg Gln Ala Pro Gly Lys Gly Leu Glu Trp Ile
            35                  40                  45

Ser Ser Ile Thr Asn Thr Gly Gly Ala Thr Tyr Tyr Leu Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
            85                  90                  95

Thr Ser Pro Gly Leu Tyr Phe Asp Tyr Trp Gly Gln Gly Val Met Val
            100                 105                 110

Thr Val Ser Ser
        115

<210> SEQ ID NO 28
<211> LENGTH: 116
<212> TYPE: PRT
<213> ORGANISM: Artificial Sequence
<220> FEATURE:
<223> OTHER INFORMATION: hSG16.45 vH2

<400> SEQUENCE: 28

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Asn Asp His
            20                  25                  30

Trp Met Thr Trp Ile Arg Gln Ala Pro Gly Lys Gly Leu Glu Trp Ile
            35                  40                  45

Ser Ala Ile Thr Asn Thr Gly Gly Ala Thr Tyr Tyr Ala Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
            85                  90                  95

Thr Ser Pro Gly Leu Tyr Phe Asp Tyr Trp Gly Gln Gly Val Met Val
            100                 105                 110

Thr Val Ser Ser
        115

<210> SEQ ID NO 29
<211> LENGTH: 116
<212> TYPE: PRT
<213> ORGANISM: Artificial Sequence

```
<220> FEATURE:
<223> OTHER INFORMATION: hSG16.45 vH3

<400> SEQUENCE: 29

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Asn Asp His
            20                  25                  30

Trp Met Thr Trp Ile Arg Gln Ala Pro Gly Lys Gly Leu Glu Trp Ile
        35                  40                  45

Ser Ala Ile Thr Asn Thr Gly Gly Ala Thr Tyr Tyr Ala Asp Ser Val
    50                  55                  60

Lys Gly Arg Phe Thr Ile Ser Arg Asp Asn Ser Lys Ser Thr Leu Tyr
65                  70                  75                  80

Leu Gln Met Asn Ser Leu Arg Ala Glu Asp Thr Ala Val Tyr Tyr Cys
                85                  90                  95

Thr Ser Pro Gly Leu Tyr Phe Asp Tyr Trp Gly Gln Gly Val Met Val
            100                 105                 110

Thr Val Ser Ser
        115

<210> SEQ ID NO 30
<211> LENGTH: 116
<212> TYPE: PRT
<213> ORGANISM: Artificial Sequence
<220> FEATURE:
<223> OTHER INFORMATION: hSG16.45 vH4

<400> SEQUENCE: 30

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Asn Asp His
            20                  25                  30

Trp Met Thr Trp Val Arg Gln Ala Pro Gly Lys Gly Leu Glu Trp Ile
        35                  40                  45

Ser Ser Ile Thr Asn Thr Gly Gly Ala Thr Tyr Tyr Ala Asp Ser Val
    50                  55                  60

Lys Gly Arg Phe Thr Ile Ser Arg Asp Asn Ser Lys Ser Thr Leu Tyr
65                  70                  75                  80

Leu Gln Met Asn Ser Leu Arg Ala Glu Asp Thr Ala Val Tyr Tyr Cys
                85                  90                  95

Thr Ser Pro Gly Leu Tyr Phe Asp Tyr Trp Gly Gln Gly Thr Met Val
            100                 105                 110

Thr Val Ser Ser
        115

<210> SEQ ID NO 31
<211> LENGTH: 116
<212> TYPE: PRT
<213> ORGANISM: Artificial Sequence
<220> FEATURE:
<223> OTHER INFORMATION: hSG16.45 vH5

<400> SEQUENCE: 31

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Asn Asp His
            20                  25                  30
```

```
Trp Met Thr Trp Val Arg Gln Ala Pro Gly Lys Gly Leu Val Trp Val
            35                  40                  45

Ser Ser Ile Thr Asn Thr Gly Gly Ala Thr Tyr Tyr Ala Asp Ser Val
 50                  55                  60

Lys Gly Arg Phe Thr Ile Ser Arg Asp Asn Ala Lys Asn Thr Leu Tyr
 65                  70                  75                  80

Leu Gln Met Asn Ser Leu Arg Ala Glu Asp Thr Ala Val Tyr Tyr Cys
                85                  90                  95

Thr Ser Pro Gly Leu Tyr Phe Asp Tyr Trp Gly Gln Gly Thr Met Val
            100                 105                 110

Thr Val Ser Ser
            115

<210> SEQ ID NO 32
<211> LENGTH: 116
<212> TYPE: PRT
<213> ORGANISM: Artificial Sequence
<220> FEATURE:
<223> OTHER INFORMATION: hSG16.45 vH6

<400> SEQUENCE: 32

Glu Val Gln Leu Val Glu Ser Gly Gly Gly Leu Val Gln Pro Gly Arg
 1               5                  10                  15

Ser Leu Arg Leu Ser Cys Ala Ala Ser Gly Phe Thr Phe Asn Asp His
            20                  25                  30

Trp Met Thr Trp Val Arg Gln Ala Pro Gly Lys Gly Leu Glu Trp Val
            35                  40                  45

Ser Gly Ile Thr Asn Thr Gly Gly Ala Thr Tyr Tyr Ala Asp Ser Val
 50                  55                  60

Lys Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Leu Tyr Tyr Cys
                85                  90                  95

Thr Ser Pro Gly Leu Tyr Phe Asp Tyr Trp Gly Gln Gly Thr Met Val
            100                 105                 110

Thr Val Ser Ser
            115

<210> SEQ ID NO 33
<211> LENGTH: 107
<212> TYPE: PRT
<213> ORGANISM: Rattus norvegicus

<400> SEQUENCE: 33

Glu Ile Val Leu Thr Gln Ser Pro Thr Thr Ala Ala Ser Pro Gly
 1               5                  10                  15

Glu Lys Val Thr Ile Thr Cys Leu Ala Thr Ser Ser Val Ser Val Met
            20                  25                  30

Tyr Trp Tyr Gln His Lys Ser Gly Ala Ser Pro Lys Leu Leu Ile Tyr
            35                  40                  45

Ser Thr Ser Ser Leu Ala Ser Gly Val Pro Asp Arg Phe Ser Gly Ser
 50                  55                  60

Gly Ser Gly Thr Ser Tyr Ser Leu Thr Ile Asn Thr Met Glu Ala Glu
 65                  70                  75                  80

Asp Ala Ala Thr Tyr Tyr Cys His Gln Trp Ser Ser Asp Pro Pro Thr
                85                  90                  95

Phe Gly Ser Gly Thr Lys Leu Glu Ile Lys Arg
```

-continued

```
                100                 105

<210> SEQ ID NO 34
<211> LENGTH: 107
<212> TYPE: PRT
<213> ORGANISM: homo sapiens

<400> SEQUENCE: 34

Glu Ile Val Leu Thr Gln Ser Pro Gly Thr Leu Ser Leu Ser Pro Gly
1               5                   10                  15

Glu Arg Ala Thr Leu Ser Cys Leu Ala Thr Ser Ser Val Ser Val Met
            20                  25                  30

Tyr Trp Tyr Gln Gln Lys Pro Gly Gln Ala Pro Arg Leu Leu Ile Tyr
        35                  40                  45

Ser Thr Ser Ser Leu Ala Ser Gly Ile Pro Asp Arg Phe Ser Gly Ser
    50                  55                  60

Gly Ser Gly Thr Asp Phe Thr Leu Thr Ile Ser Arg Leu Glu Pro Glu
65                  70                  75                  80

Asp Phe Ala Val Tyr Tyr Cys His Gln Trp Ser Ser Asp Pro Pro Thr
                85                  90                  95

Phe Gly Gln Gly Thr Lys Leu Glu Ile Lys Arg
                100                 105

<210> SEQ ID NO 35
<211> LENGTH: 107
<212> TYPE: PRT
<213> ORGANISM: Artificial Sequence
<220> FEATURE:
<223> OTHER INFORMATION: hSG16.45 vK1

<400> SEQUENCE: 35

Glu Ile Val Leu Thr Gln Ser Pro Gly Thr Leu Ser Ala Ser Pro Gly
1               5                   10                  15

Glu Arg Val Thr Ile Ser Cys Arg Ala Ser Ser Ser Val Ser Val Met
            20                  25                  30

Tyr Trp Tyr Gln His Lys Pro Gly Gln Ala Pro Arg Leu Leu Ile Tyr
        35                  40                  45

Ser Thr Ser Ser Leu Ala Ser Gly Val Pro Asp Arg Phe Ser Gly Ser
    50                  55                  60

Gly Ser Gly Thr Asp Tyr Thr Leu Thr Ile Ser Arg Met Glu Pro Glu
65                  70                  75                  80

Asp Phe Ala Val Tyr Tyr Cys His Gln Trp Ser Ser Asp Pro Pro Thr
                85                  90                  95

Phe Gly Gln Gly Thr Lys Leu Glu Ile Lys Arg
                100                 105

<210> SEQ ID NO 36
<211> LENGTH: 107
<212> TYPE: PRT
<213> ORGANISM: Artificial Sequence
<220> FEATURE:
<223> OTHER INFORMATION: hSG16.45 vK2

<400> SEQUENCE: 36

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Ser Ser Val Ser Val Met
            20                  25                  30

Tyr Trp Tyr Gln Gln Lys Pro Gly Gln Ala Pro Arg Leu Leu Ile Tyr
```

35                  40                  45
Ser Thr Ser Ser Leu Ala Ser Gly Ile Pro Asp Arg Phe Ser Gly Ser
            50                  55                  60

Gly Ser Gly Thr Asp Phe Thr Leu Thr Ile Ser Arg Leu Glu Pro Glu
65                  70                  75                  80

Asp Phe Ala Val Tyr Tyr Cys His Gln Trp Ser Asp Pro Pro Thr
                85                  90                  95

Phe Gly Gln Gly Thr Lys Leu Glu Ile Lys Arg
            100                 105

<210> SEQ ID NO 37
<211> LENGTH: 107
<212> TYPE: PRT
<213> ORGANISM: Artificial Sequence
<220> FEATURE:
<223> OTHER INFORMATION: hSG16.45 vK3

<400> SEQUENCE: 37

Glu Ile Val Leu Thr Gln Ser Pro Gly Thr Leu Ser Leu Ser Pro Gly
1               5                   10                  15

Glu Arg Ala Thr Ile Ser Cys Arg Ala Ser Ser Val Ser Val Met
            20                  25                  30

Tyr Trp Tyr Gln His Lys Pro Gly Gln Ala Pro Arg Leu Leu Ile Tyr
                35                  40                  45

Ser Thr Ser Ser Leu Ala Ser Gly Val Pro Asp Arg Phe Ser Gly Ser
            50                  55                  60

Gly Ser Gly Thr Asp Tyr Thr Leu Thr Ile Ser Arg Leu Glu Pro Glu
65                  70                  75                  80

Asp Phe Ala Val Tyr Tyr Cys His Gln Trp Ser Ser Asp Pro Pro Thr
                85                  90                  95

Phe Gly Gln Gly Thr Lys Leu Glu Ile Lys Arg
            100                 105

<210> SEQ ID NO 38
<211> LENGTH: 107
<212> TYPE: PRT
<213> ORGANISM: Artificial Sequence
<220> FEATURE:
<223> OTHER INFORMATION: hSG16.45 vK5

<400> SEQUENCE: 38

Glu Ile Val Leu Thr Gln Ser Pro Gly Thr Leu Ser Leu Ser Pro Gly
1               5                   10                  15

Glu Arg Ala Thr Leu Ser Cys Leu Ala Thr Ser Val Ser Val Met
            20                  25                  30

Tyr Trp Tyr Gln His Lys Pro Gly Gln Ala Pro Arg Leu Leu Ile Tyr
                35                  40                  45

Ser Thr Ser Ser Leu Ala Ser Gly Ile Pro Asp Arg Phe Ser Gly Ser
            50                  55                  60

Gly Ser Gly Thr Asp Tyr Thr Leu Thr Ile Ser Arg Leu Glu Pro Glu
65                  70                  75                  80

Asp Phe Ala Val Tyr Tyr Cys His Gln Trp Ser Ser Asp Pro Pro Thr
                85                  90                  95

Phe Gly Gln Gly Thr Lys Leu Glu Ile Lys Arg
            100                 105

<210> SEQ ID NO 39
<211> LENGTH: 5

```
<212> TYPE: PRT
<213> ORGANISM: Rattus norvegicus

<400> SEQUENCE: 39

Asp Tyr Tyr Ile His
1               5

<210> SEQ ID NO 40
<211> LENGTH: 17
<212> TYPE: PRT
<213> ORGANISM: Rattus norvegicus

<400> SEQUENCE: 40

Tyr Ile Asn Pro Asn Ser Gly Tyr Thr Lys Tyr Asn Glu Asn Phe Lys
1               5                   10                  15

Thr

<210> SEQ ID NO 41
<211> LENGTH: 12
<212> TYPE: PRT
<213> ORGANISM: Rattus norvegicus

<400> SEQUENCE: 41

Tyr Met Trp Glu Arg Val Thr Gly Phe Phe Asp Phe
1               5                   10

<210> SEQ ID NO 42
<211> LENGTH: 8
<212> TYPE: PRT
<213> ORGANISM: Rattus norvegicus

<400> SEQUENCE: 42

Ile Asn Pro Asn Ser Gly Tyr Thr
1               5

<210> SEQ ID NO 43
<211> LENGTH: 14
<212> TYPE: PRT
<213> ORGANISM: Rattus norvegicus

<400> SEQUENCE: 43

Thr Arg Tyr Met Trp Glu Arg Val Thr Gly Phe Phe Asp Phe
1               5                   10

<210> SEQ ID NO 44
<211> LENGTH: 5
<212> TYPE: PRT
<213> ORGANISM: homo sapiens

<400> SEQUENCE: 44

Gly Tyr Tyr Met His
1               5

<210> SEQ ID NO 45
<211> LENGTH: 17
<212> TYPE: PRT
<213> ORGANISM: homo sapiens

<400> SEQUENCE: 45

Arg Ile Asn Pro Asn Ser Gly Gly Thr Asn Tyr Ala Gln Lys Phe Gln
1               5                   10                  15

Gly
```

```
<210> SEQ ID NO 46
<211> LENGTH: 8
<212> TYPE: PRT
<213> ORGANISM: homo sapiens

<400> SEQUENCE: 46

Ile Asn Pro Asn Ser Gly Gly Thr
1               5

<210> SEQ ID NO 47
<211> LENGTH: 5
<212> TYPE: PRT
<213> ORGANISM: homo sapiens

<400> SEQUENCE: 47

Ser Tyr Tyr Met His
1               5

<210> SEQ ID NO 48
<211> LENGTH: 17
<212> TYPE: PRT
<213> ORGANISM: homo sapiens

<400> SEQUENCE: 48

Ile Ile Asn Pro Ser Gly Gly Ser Thr Ser Tyr Ala Gln Lys Phe Gln
1               5                   10                  15

Gly

<210> SEQ ID NO 49
<211> LENGTH: 8
<212> TYPE: PRT
<213> ORGANISM: homo sapiens

<400> SEQUENCE: 49

Ile Asn Pro Ser Gly Gly Ser Thr
1               5

<210> SEQ ID NO 50
<211> LENGTH: 5
<212> TYPE: PRT
<213> ORGANISM: Artificial Sequence
<220> FEATURE:
<223> OTHER INFORMATION: hSG16.17 vH1 Kabat CDR1

<400> SEQUENCE: 50

Asp Tyr Tyr Ile His
1               5

<210> SEQ ID NO 51
<211> LENGTH: 17
<212> TYPE: PRT
<213> ORGANISM: Artificial Sequence
<220> FEATURE:
<223> OTHER INFORMATION: hSG16.17 vH1 Kabat CDR2

<400> SEQUENCE: 51

Tyr Ile Asn Pro Asn Ser Gly Tyr Thr Lys Tyr Asn Glu Asn Phe Lys
1               5                   10                  15

Thr

<210> SEQ ID NO 52
<211> LENGTH: 12
<212> TYPE: PRT
<213> ORGANISM: Artificial Sequence
<220> FEATURE:
```

-continued

<223> OTHER INFORMATION: hSG16.17 vH1 Kabat CDR3

<400> SEQUENCE: 52

Tyr Met Trp Glu Arg Val Thr Gly Phe Phe Asp Phe
1               5                   10

<210> SEQ ID NO 53
<211> LENGTH: 8
<212> TYPE: PRT
<213> ORGANISM: Artificial Sequence
<220> FEATURE:
<223> OTHER INFORMATION: hSG16.17 vH1 IMGT CDR1

<400> SEQUENCE: 53

Ile Asn Pro Asn Ser Gly Tyr Thr
1               5

<210> SEQ ID NO 54
<211> LENGTH: 14
<212> TYPE: PRT
<213> ORGANISM: Artificial Sequence
<220> FEATURE:
<223> OTHER INFORMATION: hSG16.17 vH1 IMGT CDR2

<400> SEQUENCE: 54

Thr Arg Tyr Met Trp Glu Arg Val Thr Gly Phe Phe Asp Phe
1               5                   10

<210> SEQ ID NO 55
<211> LENGTH: 5
<212> TYPE: PRT
<213> ORGANISM: Artificial Sequence
<220> FEATURE:
<223> OTHER INFORMATION: hSG16.17 vH2 Kabat CDR1

<400> SEQUENCE: 55

Asp Tyr Tyr Met His
1               5

<210> SEQ ID NO 56
<211> LENGTH: 17
<212> TYPE: PRT
<213> ORGANISM: Artificial Sequence
<220> FEATURE:
<223> OTHER INFORMATION: hSG16.17 vH2 Kabat CDR2

<400> SEQUENCE: 56

Arg Ile Asn Pro Asn Ser Gly Tyr Thr Asn Tyr Ala Gln Lys Phe Gln
1               5                   10                  15

Gly

<210> SEQ ID NO 57
<211> LENGTH: 12
<212> TYPE: PRT
<213> ORGANISM: Artificial Sequence
<220> FEATURE:
<223> OTHER INFORMATION: hSG16.17 vH2 Kabat CDR3

<400> SEQUENCE: 57

Tyr Met Trp Glu Arg Val Thr Gly Phe Phe Asp Phe
1               5                   10

<210> SEQ ID NO 58
<211> LENGTH: 8
<212> TYPE: PRT
<213> ORGANISM: Artificial Sequence

```
<220> FEATURE:
<223> OTHER INFORMATION: hSG16.17 vH2 IMGT CDR1

<400> SEQUENCE: 58

Ile Asn Pro Asn Ser Gly Tyr Thr
1               5

<210> SEQ ID NO 59
<211> LENGTH: 14
<212> TYPE: PRT
<213> ORGANISM: Artificial Sequence
<220> FEATURE:
<223> OTHER INFORMATION: hSG16.17 vH2 IMGT CDR2

<400> SEQUENCE: 59

Thr Arg Tyr Met Trp Glu Arg Val Thr Gly Phe Phe Asp Phe
1               5                   10

<210> SEQ ID NO 60
<211> LENGTH: 5
<212> TYPE: PRT
<213> ORGANISM: Artificial Sequence
<220> FEATURE:
<223> OTHER INFORMATION: hSG16.17 vH3 Kabat CDR1

<400> SEQUENCE: 60

Asp Tyr Tyr Ile His
1               5

<210> SEQ ID NO 61
<211> LENGTH: 17
<212> TYPE: PRT
<213> ORGANISM: Artificial Sequence
<220> FEATURE:
<223> OTHER INFORMATION: hSG16.17 vH3 Kabat CDR2

<400> SEQUENCE: 61

Tyr Ile Asn Pro Asn Ser Gly Tyr Thr Asn Tyr Ala Gln Lys Phe Gln
1               5                   10                  15

Gly

<210> SEQ ID NO 62
<211> LENGTH: 12
<212> TYPE: PRT
<213> ORGANISM: Artificial Sequence
<220> FEATURE:
<223> OTHER INFORMATION: hSG16.17 vH3 Kabat CDR3

<400> SEQUENCE: 62

Tyr Met Trp Glu Arg Val Thr Gly Phe Phe Asp Phe
1               5                   10

<210> SEQ ID NO 63
<211> LENGTH: 8
<212> TYPE: PRT
<213> ORGANISM: Artificial Sequence
<220> FEATURE:
<223> OTHER INFORMATION: hSG16.17 vH3 IMGT CDR1

<400> SEQUENCE: 63

Ile Asn Pro Asn Ser Gly Tyr Thr
1               5

<210> SEQ ID NO 64
<211> LENGTH: 14
<212> TYPE: PRT
```

<213> ORGANISM: Artificial Sequence
<220> FEATURE:
<223> OTHER INFORMATION: hSG16.17 vH3 IMGT CDR2

<400> SEQUENCE: 64

Thr Arg Tyr Met Trp Glu Arg Val Thr Gly Phe Phe Asp Phe
1               5                   10

<210> SEQ ID NO 65
<211> LENGTH: 5
<212> TYPE: PRT
<213> ORGANISM: Artificial Sequence
<220> FEATURE:
<223> OTHER INFORMATION: hSG16.17 vH4 Kabat CDR1

<400> SEQUENCE: 65

Asp Tyr Tyr Met His
1               5

<210> SEQ ID NO 66
<211> LENGTH: 17
<212> TYPE: PRT
<213> ORGANISM: Artificial Sequence
<220> FEATURE:
<223> OTHER INFORMATION: hSG16.17 vH4 Kabat CDR2

<400> SEQUENCE: 66

Arg Ile Asn Pro Asn Ser Gly Tyr Thr Asn Tyr Ala Gln Lys Phe Gln
1               5                   10                  15

Gly

<210> SEQ ID NO 67
<211> LENGTH: 12
<212> TYPE: PRT
<213> ORGANISM: Artificial Sequence
<220> FEATURE:
<223> OTHER INFORMATION: hSG16.17 vH4 Kabat CDR3

<400> SEQUENCE: 67

Tyr Met Trp Glu Arg Val Thr Gly Phe Phe Asp Phe
1               5                   10

<210> SEQ ID NO 68
<211> LENGTH: 8
<212> TYPE: PRT
<213> ORGANISM: Artificial Sequence
<220> FEATURE:
<223> OTHER INFORMATION: hSG16.17 vH4 IMGT CDR1

<400> SEQUENCE: 68

Ile Asn Pro Asn Ser Gly Tyr Thr
1               5

<210> SEQ ID NO 69
<211> LENGTH: 14
<212> TYPE: PRT
<213> ORGANISM: Artificial Sequence
<220> FEATURE:
<223> OTHER INFORMATION: hSG16.17 vH4 IMGT CDR2

<400> SEQUENCE: 69

Thr Arg Tyr Met Trp Glu Arg Val Thr Gly Phe Phe Asp Phe
1               5                   10

<210> SEQ ID NO 70
<211> LENGTH: 5

```
<212> TYPE: PRT
<213> ORGANISM: Artificial Sequence
<220> FEATURE:
<223> OTHER INFORMATION: hSG16.17 vH5 Kabat CDR1

<400> SEQUENCE: 70

Asp Tyr Tyr Ile His
1               5

<210> SEQ ID NO 71
<211> LENGTH: 17
<212> TYPE: PRT
<213> ORGANISM: Artificial Sequence
<220> FEATURE:
<223> OTHER INFORMATION: hSG16.17 vH5 Kabat CDR2

<400> SEQUENCE: 71

Tyr Ile Asn Pro Asn Ser Gly Tyr Thr Lys Tyr Asn Glu Asn Phe Lys
1               5                   10                  15

Thr

<210> SEQ ID NO 72
<211> LENGTH: 12
<212> TYPE: PRT
<213> ORGANISM: Artificial Sequence
<220> FEATURE:
<223> OTHER INFORMATION: hSG16.17 vH5 Kabat CDR3

<400> SEQUENCE: 72

Tyr Met Trp Glu Arg Val Thr Gly Phe Phe Asp Phe
1               5                   10

<210> SEQ ID NO 73
<211> LENGTH: 8
<212> TYPE: PRT
<213> ORGANISM: Artificial Sequence
<220> FEATURE:
<223> OTHER INFORMATION: hSG16.17 vH5 IMGT CDR1

<400> SEQUENCE: 73

Ile Asn Pro Asn Ser Gly Tyr Thr
1               5

<210> SEQ ID NO 74
<211> LENGTH: 14
<212> TYPE: PRT
<213> ORGANISM: Artificial Sequence
<220> FEATURE:
<223> OTHER INFORMATION: hSG16.17 vH5 IMGT CDR2

<400> SEQUENCE: 74

Thr Arg Tyr Met Trp Glu Arg Val Thr Gly Phe Phe Asp Phe
1               5                   10

<210> SEQ ID NO 75
<211> LENGTH: 5
<212> TYPE: PRT
<213> ORGANISM: Artificial Sequence
<220> FEATURE:
<223> OTHER INFORMATION: hSG16.17 vH6 Kabat CDR1

<400> SEQUENCE: 75

Asp Tyr Tyr Met His
1               5

<210> SEQ ID NO 76
```

```
<211> LENGTH: 17
<212> TYPE: PRT
<213> ORGANISM: Artificial Sequence
<220> FEATURE:
<223> OTHER INFORMATION: hSG16.17 vH6 Kabat CDR2

<400> SEQUENCE: 76

Ile Ile Asn Pro Asn Ser Gly Tyr Thr Ser Tyr Ala Gln Lys Phe Gln
1               5                   10                  15
Gly

<210> SEQ ID NO 77
<211> LENGTH: 12
<212> TYPE: PRT
<213> ORGANISM: Artificial Sequence
<220> FEATURE:
<223> OTHER INFORMATION: hSG16.17 vH6 Kabat CDR3

<400> SEQUENCE: 77

Tyr Met Trp Glu Arg Val Thr Gly Phe Phe Asp Phe
1               5                   10

<210> SEQ ID NO 78
<211> LENGTH: 8
<212> TYPE: PRT
<213> ORGANISM: Artificial Sequence
<220> FEATURE:
<223> OTHER INFORMATION: hSG16.17 vH6 IMGT CDR1

<400> SEQUENCE: 78

Ile Asn Pro Asn Ser Gly Tyr Thr
1               5

<210> SEQ ID NO 79
<211> LENGTH: 14
<212> TYPE: PRT
<213> ORGANISM: Artificial Sequence
<220> FEATURE:
<223> OTHER INFORMATION: hSG16.17 vH6 IMGT CDR2

<400> SEQUENCE: 79

Thr Arg Tyr Met Trp Glu Arg Val Thr Gly Phe Phe Asp Phe
1               5                   10

<210> SEQ ID NO 80
<211> LENGTH: 11
<212> TYPE: PRT
<213> ORGANISM: Rattus norvegicus

<400> SEQUENCE: 80

Leu Ala Ser Glu Asp Ile Ser Asp Asp Leu Ala
1               5                   10

<210> SEQ ID NO 81
<211> LENGTH: 7
<212> TYPE: PRT
<213> ORGANISM: Rattus norvegicus

<400> SEQUENCE: 81

Thr Thr Ser Arg Leu Gln Asp
1               5

<210> SEQ ID NO 82
<211> LENGTH: 9
<212> TYPE: PRT
<213> ORGANISM: Rattus norvegicus
```

<400> SEQUENCE: 82

Gln Gln Thr Tyr Lys Phe Pro Pro Thr
1               5

<210> SEQ ID NO 83
<211> LENGTH: 6
<212> TYPE: PRT
<213> ORGANISM: Rattus norvegicus

<400> SEQUENCE: 83

Glu Asp Ile Ser Asp Asp
1               5

<210> SEQ ID NO 84
<211> LENGTH: 9
<212> TYPE: PRT
<213> ORGANISM: Rattus norvegicus

<400> SEQUENCE: 84

Gln Gln Thr Tyr Lys Phe Pro Pro Thr
1               5

<210> SEQ ID NO 85
<211> LENGTH: 11
<212> TYPE: PRT
<213> ORGANISM: homo sapiens

<400> SEQUENCE: 85

Arg Ala Ser Gln Gly Ile Ser Ser Trp Leu Ala
1               5                   10

<210> SEQ ID NO 86
<211> LENGTH: 7
<212> TYPE: PRT
<213> ORGANISM: homo sapiens

<400> SEQUENCE: 86

Ala Ala Ser Ser Leu Gln Ser
1               5

<210> SEQ ID NO 87
<211> LENGTH: 7
<212> TYPE: PRT
<213> ORGANISM: homo sapiens

<400> SEQUENCE: 87

Gln Gln Ala Asn Ser Phe Pro
1               5

<210> SEQ ID NO 88
<211> LENGTH: 6
<212> TYPE: PRT
<213> ORGANISM: homo sapiens

<400> SEQUENCE: 88

Gln Gly Ile Ser Ser Trp
1               5

<210> SEQ ID NO 89
<211> LENGTH: 7
<212> TYPE: PRT
<213> ORGANISM: homo sapiens

<400> SEQUENCE: 89

```
Gln Gln Ala Asn Ser Phe Pro
1               5

<210> SEQ ID NO 90
<211> LENGTH: 11
<212> TYPE: PRT
<213> ORGANISM: Artificial Sequence
<220> FEATURE:
<223> OTHER INFORMATION: hSG16.17 vK2 Kabat CDR1

<400> SEQUENCE: 90

Leu Ala Ser Glu Asp Ile Ser Asp Asp Leu Ala
1               5                   10

<210> SEQ ID NO 91
<211> LENGTH: 7
<212> TYPE: PRT
<213> ORGANISM: Artificial Sequence
<220> FEATURE:
<223> OTHER INFORMATION: hSG16.17 vK2 Kabat CDR2

<400> SEQUENCE: 91

Thr Thr Ser Ser Leu Gln Ser
1               5

<210> SEQ ID NO 92
<211> LENGTH: 9
<212> TYPE: PRT
<213> ORGANISM: Artificial Sequence
<220> FEATURE:
<223> OTHER INFORMATION: hSG16.17 vK2 Kabat CDR3

<400> SEQUENCE: 92

Gln Gln Thr Tyr Lys Phe Pro Pro Thr
1               5

<210> SEQ ID NO 93
<211> LENGTH: 6
<212> TYPE: PRT
<213> ORGANISM: Artificial Sequence
<220> FEATURE:
<223> OTHER INFORMATION: hSG16.17 vK2 IMGT CDR1

<400> SEQUENCE: 93

Glu Asp Ile Ser Asp Asp
1               5

<210> SEQ ID NO 94
<211> LENGTH: 9
<212> TYPE: PRT
<213> ORGANISM: Artificial Sequence
<220> FEATURE:
<223> OTHER INFORMATION: hSG16.17 vK2 IMGT CDR3

<400> SEQUENCE: 94

Gln Gln Thr Tyr Lys Phe Pro Pro Thr
1               5

<210> SEQ ID NO 95
<211> LENGTH: 11
<212> TYPE: PRT
<213> ORGANISM: Artificial Sequence
<220> FEATURE:
<223> OTHER INFORMATION: hSG16.17 vK3 Kabat CDR1

<400> SEQUENCE: 95
```

Arg Ala Ser Glu Asp Ile Ser Asp Asp Leu Ala
1               5                   10

<210> SEQ ID NO 96
<211> LENGTH: 7
<212> TYPE: PRT
<213> ORGANISM: Artificial Sequence
<220> FEATURE:
<223> OTHER INFORMATION: hSG16.17 vK3 Kabat CDR2

<400> SEQUENCE: 96

Thr Thr Ser Ser Leu Gln Ser
1               5

<210> SEQ ID NO 97
<211> LENGTH: 9
<212> TYPE: PRT
<213> ORGANISM: Artificial Sequence
<220> FEATURE:
<223> OTHER INFORMATION: hSG16.17 vK3 Kabat CDR3

<400> SEQUENCE: 97

Gln Gln Thr Tyr Lys Phe Pro Pro Thr
1               5

<210> SEQ ID NO 98
<211> LENGTH: 6
<212> TYPE: PRT
<213> ORGANISM: Artificial Sequence
<220> FEATURE:
<223> OTHER INFORMATION: hSG16.17 vK3 IMGT CDR1

<400> SEQUENCE: 98

Glu Asp Ile Ser Asp Asp
1               5

<210> SEQ ID NO 99
<211> LENGTH: 9
<212> TYPE: PRT
<213> ORGANISM: Artificial Sequence
<220> FEATURE:
<223> OTHER INFORMATION: hSG16.17 vK3 IMGT CDR3

<400> SEQUENCE: 99

Gln Gln Thr Tyr Lys Phe Pro Pro Thr
1               5

<210> SEQ ID NO 100
<211> LENGTH: 11
<212> TYPE: PRT
<213> ORGANISM: Artificial Sequence
<220> FEATURE:
<223> OTHER INFORMATION: hSG16.17 vK4 Kabat CDR1

<400> SEQUENCE: 100

Leu Ala Ser Glu Asp Ile Ser Asp Asp Leu Ala
1               5                   10

<210> SEQ ID NO 101
<211> LENGTH: 7
<212> TYPE: PRT
<213> ORGANISM: Artificial Sequence
<220> FEATURE:
<223> OTHER INFORMATION: hSG16.17 vK4 Kabat CDR2

<400> SEQUENCE: 101

Thr Thr Ser Arg Leu Gln Ser

```
<210> SEQ ID NO 102
<211> LENGTH: 9
<212> TYPE: PRT
<213> ORGANISM: Artificial Sequence
<220> FEATURE:
<223> OTHER INFORMATION: hSG16.17 vK4 Kabat CDR3

<400> SEQUENCE: 102

Gln Gln Thr Tyr Lys Phe Pro Pro Thr
1               5

<210> SEQ ID NO 103
<211> LENGTH: 6
<212> TYPE: PRT
<213> ORGANISM: Artificial Sequence
<220> FEATURE:
<223> OTHER INFORMATION: hSG16.17 vK4 IMGT CDR1

<400> SEQUENCE: 103

Glu Asp Ile Ser Asp Asp
1               5

<210> SEQ ID NO 104
<211> LENGTH: 9
<212> TYPE: PRT
<213> ORGANISM: Artificial Sequence
<220> FEATURE:
<223> OTHER INFORMATION: hSG16.17 vK4 IMGT CDR3

<400> SEQUENCE: 104

Gln Gln Thr Tyr Lys Phe Pro Pro Thr
1               5

<210> SEQ ID NO 105
<211> LENGTH: 11
<212> TYPE: PRT
<213> ORGANISM: Artificial Sequence
<220> FEATURE:
<223> OTHER INFORMATION: hSG16.17 vK5 Kabat CDR1

<400> SEQUENCE: 105

Arg Ala Ser Glu Asp Ile Ser Asp Asp Leu Ala
1               5                   10

<210> SEQ ID NO 106
<211> LENGTH: 7
<212> TYPE: PRT
<213> ORGANISM: Artificial Sequence
<220> FEATURE:
<223> OTHER INFORMATION: hSG16.17 vK5 Kabat CDR2

<400> SEQUENCE: 106

Thr Thr Ser Ser Leu Gln Ser
1               5

<210> SEQ ID NO 107
<211> LENGTH: 9
<212> TYPE: PRT
<213> ORGANISM: Artificial Sequence
<220> FEATURE:
<223> OTHER INFORMATION: hSG16.17 vK5 Kabat CDR3

<400> SEQUENCE: 107

Gln Gln Thr Tyr Lys Phe Pro Pro Thr
1               5
```

<210> SEQ ID NO 108
<211> LENGTH: 6
<212> TYPE: PRT
<213> ORGANISM: Artificial Sequence
<220> FEATURE:
<223> OTHER INFORMATION: hSG16.17 vK5 IMGT CDR1

<400> SEQUENCE: 108

Glu Asp Ile Ser Asp Asp
1               5

<210> SEQ ID NO 109
<211> LENGTH: 9
<212> TYPE: PRT
<213> ORGANISM: Artificial Sequence
<220> FEATURE:
<223> OTHER INFORMATION: hSG16.17 vK5 IMGT CDR3

<400> SEQUENCE: 109

Gln Gln Thr Tyr Lys Phe Pro Pro Thr
1               5

<210> SEQ ID NO 110
<211> LENGTH: 5
<212> TYPE: PRT
<213> ORGANISM: Rattus norvegicus

<400> SEQUENCE: 110

Asp His Trp Met Thr
1               5

<210> SEQ ID NO 111
<211> LENGTH: 17
<212> TYPE: PRT
<213> ORGANISM: Rattus norvegicus

<400> SEQUENCE: 111

Ser Ile Thr Asn Thr Gly Gly Ala Thr Tyr Tyr Leu Asp Ser Val Lys
1               5                   10                  15

Gly

<210> SEQ ID NO 112
<211> LENGTH: 7
<212> TYPE: PRT
<213> ORGANISM: Rattus norvegicus

<400> SEQUENCE: 112

Pro Gly Leu Tyr Phe Asp Tyr
1               5

<210> SEQ ID NO 113
<211> LENGTH: 7
<212> TYPE: PRT
<213> ORGANISM: Rattus norvegicus

<400> SEQUENCE: 113

Gly Phe Thr Phe Asn Asp His
1               5

<210> SEQ ID NO 114
<211> LENGTH: 8
<212> TYPE: PRT
<213> ORGANISM: Rattus norvegicus

```
<400> SEQUENCE: 114

Ile Thr Asn Thr Gly Gly Ala Thr
1               5

<210> SEQ ID NO 115
<211> LENGTH: 9
<212> TYPE: PRT
<213> ORGANISM: Rattus norvegicus

<400> SEQUENCE: 115

Thr Ser Pro Gly Leu Tyr Phe Asp Tyr
1               5

<210> SEQ ID NO 116
<211> LENGTH: 5
<212> TYPE: PRT
<213> ORGANISM: homo sapiens

<400> SEQUENCE: 116

Asp His Trp Met Thr
1               5

<210> SEQ ID NO 117
<211> LENGTH: 17
<212> TYPE: PRT
<213> ORGANISM: homo sapiens

<400> SEQUENCE: 117

Ser Ile Thr Asn Thr Gly Gly Ala Thr Tyr Tyr Leu Asp Ser Val Lys
1               5                   10                  15

Gly

<210> SEQ ID NO 118
<211> LENGTH: 8
<212> TYPE: PRT
<213> ORGANISM: homo sapiens

<400> SEQUENCE: 118

Gly Phe Thr Phe Ser Asp His Trp
1               5

<210> SEQ ID NO 119
<211> LENGTH: 8
<212> TYPE: PRT
<213> ORGANISM: homo sapiens

<400> SEQUENCE: 119

Ile Thr Asn Thr Gly Gly Ala Thr
1               5

<210> SEQ ID NO 120
<211> LENGTH: 5
<212> TYPE: PRT
<213> ORGANISM: homo sapiens

<400> SEQUENCE: 120

Asp His Trp Met Thr
1               5

<210> SEQ ID NO 121
<211> LENGTH: 17
<212> TYPE: PRT
<213> ORGANISM: homo sapiens
```

```
<400> SEQUENCE: 121

Ser Ile Thr Asn Thr Gly Gly Ala Thr Tyr Tyr Leu Asp Ser Val Lys
1               5                   10                  15

Gly

<210> SEQ ID NO 122
<211> LENGTH: 8
<212> TYPE: PRT
<213> ORGANISM: homo sapiens

<400> SEQUENCE: 122

Gly Phe Thr Phe Ser Asp His Trp
1               5

<210> SEQ ID NO 123
<211> LENGTH: 8
<212> TYPE: PRT
<213> ORGANISM: homo sapiens

<400> SEQUENCE: 123

Ile Thr Asn Thr Gly Gly Ala Thr
1               5

<210> SEQ ID NO 124
<211> LENGTH: 5
<212> TYPE: PRT
<213> ORGANISM: homo sapiens

<400> SEQUENCE: 124

Asp His Trp Met Thr
1               5

<210> SEQ ID NO 125
<211> LENGTH: 17
<212> TYPE: PRT
<213> ORGANISM: homo sapiens

<400> SEQUENCE: 125

Ser Ile Thr Asn Thr Gly Gly Ala Thr Tyr Tyr Leu Asp Ser Val Lys
1               5                   10                  15

Gly

<210> SEQ ID NO 126
<211> LENGTH: 8
<212> TYPE: PRT
<213> ORGANISM: homo sapiens

<400> SEQUENCE: 126

Gly Phe Thr Phe Asp Asp His Trp
1               5

<210> SEQ ID NO 127
<211> LENGTH: 8
<212> TYPE: PRT
<213> ORGANISM: homo sapiens

<400> SEQUENCE: 127

Ile Thr Asn Thr Gly Gly Ala Thr
1               5

<210> SEQ ID NO 128
<211> LENGTH: 5
<212> TYPE: PRT
```

<213> ORGANISM: Artificial Sequence
<220> FEATURE:
<223> OTHER INFORMATION: hSG16.45 vH1 Kabat CDR1

<400> SEQUENCE: 128

Asp His Trp Met Thr
1               5

<210> SEQ ID NO 129
<211> LENGTH: 17
<212> TYPE: PRT
<213> ORGANISM: Artificial Sequence
<220> FEATURE:
<223> OTHER INFORMATION: hSG16.45 vH1 Kabat CDR2

<400> SEQUENCE: 129

Ser Ile Thr Asn Thr Gly Gly Ala Thr Tyr Tyr Leu Asp Ser Val Lys
1               5                   10                  15

Gly

<210> SEQ ID NO 130
<211> LENGTH: 7
<212> TYPE: PRT
<213> ORGANISM: Artificial Sequence
<220> FEATURE:
<223> OTHER INFORMATION: hSG16.45 vH1 Kabat CDR3

<400> SEQUENCE: 130

Pro Gly Leu Tyr Phe Asp Tyr
1               5

<210> SEQ ID NO 131
<211> LENGTH: 8
<212> TYPE: PRT
<213> ORGANISM: Artificial Sequence
<220> FEATURE:
<223> OTHER INFORMATION: hSG16.45 vH1 IMGT CDR1

<400> SEQUENCE: 131

Gly Phe Thr Phe Asn Asp His Trp
1               5

<210> SEQ ID NO 132
<211> LENGTH: 8
<212> TYPE: PRT
<213> ORGANISM: Artificial Sequence
<220> FEATURE:
<223> OTHER INFORMATION: hSG16.45 vH1 IMGT CDR1

<400> SEQUENCE: 132

Ile Thr Asn Thr Gly Gly Ala Thr
1               5

<210> SEQ ID NO 133
<211> LENGTH: 9
<212> TYPE: PRT
<213> ORGANISM: Artificial Sequence
<220> FEATURE:
<223> OTHER INFORMATION: hSG16.45 vH1 IMGT CDR1

<400> SEQUENCE: 133

Thr Ser Pro Gly Leu Tyr Phe Asp Tyr
1               5

<210> SEQ ID NO 134
<211> LENGTH: 5

```
<212> TYPE: PRT
<213> ORGANISM: Artificial Sequence
<220> FEATURE:
<223> OTHER INFORMATION: hSG16.45 vH2 Kabat CDR1

<400> SEQUENCE: 134

Asp His Trp Met Thr
1               5

<210> SEQ ID NO 135
<211> LENGTH: 17
<212> TYPE: PRT
<213> ORGANISM: Artificial Sequence
<220> FEATURE:
<223> OTHER INFORMATION: hSG16.45 vH2 Kabat CDR2

<400> SEQUENCE: 135

Ala Ile Thr Asn Thr Gly Gly Ala Thr Tyr Tyr Ala Asp Ser Val Lys
1               5                   10                  15

Gly

<210> SEQ ID NO 136
<211> LENGTH: 7
<212> TYPE: PRT
<213> ORGANISM: Artificial Sequence
<220> FEATURE:
<223> OTHER INFORMATION: hSG16.45 vH2 Kabat CDR3

<400> SEQUENCE: 136

Pro Gly Leu Tyr Phe Asp Tyr
1               5

<210> SEQ ID NO 137
<211> LENGTH: 8
<212> TYPE: PRT
<213> ORGANISM: Artificial Sequence
<220> FEATURE:
<223> OTHER INFORMATION: hSG16.45 vH2 IMGT CDR1

<400> SEQUENCE: 137

Gly Phe Thr Phe Asn Asp His Trp
1               5

<210> SEQ ID NO 138
<211> LENGTH: 8
<212> TYPE: PRT
<213> ORGANISM: Artificial Sequence
<220> FEATURE:
<223> OTHER INFORMATION: hSG16.45 vH2 IMGT CDR2

<400> SEQUENCE: 138

Ile Thr Asn Thr Gly Gly Ala Thr
1               5

<210> SEQ ID NO 139
<211> LENGTH: 9
<212> TYPE: PRT
<213> ORGANISM: Artificial Sequence
<220> FEATURE:
<223> OTHER INFORMATION: hSG16.45 vH2 IMGT CDR3

<400> SEQUENCE: 139

Thr Ser Pro Gly Leu Tyr Phe Asp Tyr
1               5

<210> SEQ ID NO 140
```

```
<211> LENGTH: 5
<212> TYPE: PRT
<213> ORGANISM: Artificial Sequence
<220> FEATURE:
<223> OTHER INFORMATION: hSG16.45 vH3 Kabat CDR1

<400> SEQUENCE: 140

Asp His Trp Met Thr
1               5

<210> SEQ ID NO 141
<211> LENGTH: 17
<212> TYPE: PRT
<213> ORGANISM: Artificial Sequence
<220> FEATURE:
<223> OTHER INFORMATION: hSG16.45 vH3 Kabat CDR2

<400> SEQUENCE: 141

Ala Ile Thr Asn Thr Gly Gly Ala Thr Tyr Tyr Ala Asp Ser Val Lys
1               5                   10                  15

Gly

<210> SEQ ID NO 142
<211> LENGTH: 7
<212> TYPE: PRT
<213> ORGANISM: Artificial Sequence
<220> FEATURE:
<223> OTHER INFORMATION: hSG16.45 vH3 Kabat CDR3

<400> SEQUENCE: 142

Pro Gly Leu Tyr Phe Asp Tyr
1               5

<210> SEQ ID NO 143
<211> LENGTH: 8
<212> TYPE: PRT
<213> ORGANISM: Artificial Sequence
<220> FEATURE:
<223> OTHER INFORMATION: hSG16.45 vH3 IMGT CDR1

<400> SEQUENCE: 143

Gly Phe Thr Phe Asn Asp His Trp
1               5

<210> SEQ ID NO 144
<211> LENGTH: 8
<212> TYPE: PRT
<213> ORGANISM: Artificial Sequence
<220> FEATURE:
<223> OTHER INFORMATION: hSG16.45 vH3 IMGT CDR2

<400> SEQUENCE: 144

Ile Thr Asn Thr Gly Gly Ala Thr
1               5

<210> SEQ ID NO 145
<211> LENGTH: 9
<212> TYPE: PRT
<213> ORGANISM: Artificial Sequence
<220> FEATURE:
<223> OTHER INFORMATION: hSG16.45 vH3 IMGT CDR3

<400> SEQUENCE: 145

Thr Ser Pro Gly Leu Tyr Phe Asp Tyr
1               5
```

```
<210> SEQ ID NO 146
<211> LENGTH: 5
<212> TYPE: PRT
<213> ORGANISM: Artificial Sequence
<220> FEATURE:
<223> OTHER INFORMATION: hSG16.45 vH4 Kabat CDR1

<400> SEQUENCE: 146

Asp His Trp Met Thr
1               5

<210> SEQ ID NO 147
<211> LENGTH: 17
<212> TYPE: PRT
<213> ORGANISM: Artificial Sequence
<220> FEATURE:
<223> OTHER INFORMATION: hSG16.45 vH4 Kabat CDR2

<400> SEQUENCE: 147

Ser Ile Thr Asn Thr Gly Gly Ala Thr Tyr Tyr Ala Asp Ser Val Lys
1               5                   10                  15

Gly

<210> SEQ ID NO 148
<211> LENGTH: 7
<212> TYPE: PRT
<213> ORGANISM: Artificial Sequence
<220> FEATURE:
<223> OTHER INFORMATION: hSG16.45 vH4 Kabat CDR3

<400> SEQUENCE: 148

Pro Gly Leu Tyr Phe Asp Tyr
1               5

<210> SEQ ID NO 149
<211> LENGTH: 8
<212> TYPE: PRT
<213> ORGANISM: Artificial Sequence
<220> FEATURE:
<223> OTHER INFORMATION: hSG16.45 vH4 IMGT CDR1

<400> SEQUENCE: 149

Gly Phe Thr Phe Asn Asp His Trp
1               5

<210> SEQ ID NO 150
<211> LENGTH: 8
<212> TYPE: PRT
<213> ORGANISM: Artificial Sequence
<220> FEATURE:
<223> OTHER INFORMATION: hSG16.45 vH4 IMGT CDR2

<400> SEQUENCE: 150

Ile Thr Asn Thr Gly Gly Ala Thr
1               5

<210> SEQ ID NO 151
<211> LENGTH: 9
<212> TYPE: PRT
<213> ORGANISM: Artificial Sequence
<220> FEATURE:
<223> OTHER INFORMATION: hSG16.45 vH4 IMGT CDR3

<400> SEQUENCE: 151

Thr Ser Pro Gly Leu Tyr Phe Asp Tyr
1               5
```

```
<210> SEQ ID NO 152
<211> LENGTH: 5
<212> TYPE: PRT
<213> ORGANISM: Artificial Sequence
<220> FEATURE:
<223> OTHER INFORMATION: hSG16.45 vH5 Kabat CDR1

<400> SEQUENCE: 152

Asp His Trp Met Thr
1               5

<210> SEQ ID NO 153
<211> LENGTH: 17
<212> TYPE: PRT
<213> ORGANISM: Artificial Sequence
<220> FEATURE:
<223> OTHER INFORMATION: hSG16.45 vH5 Kabat CDR2

<400> SEQUENCE: 153

Ser Ile Thr Asn Thr Gly Gly Ala Thr Tyr Tyr Ala Asp Ser Val Lys
1               5                   10                  15

Gly

<210> SEQ ID NO 154
<211> LENGTH: 7
<212> TYPE: PRT
<213> ORGANISM: Artificial Sequence
<220> FEATURE:
<223> OTHER INFORMATION: hSG16.45 vH5 Kabat CDR3

<400> SEQUENCE: 154

Pro Gly Leu Tyr Phe Asp Tyr
1               5

<210> SEQ ID NO 155
<211> LENGTH: 8
<212> TYPE: PRT
<213> ORGANISM: Artificial Sequence
<220> FEATURE:
<223> OTHER INFORMATION: hSG16.45 vH5 IMGT CDR1

<400> SEQUENCE: 155

Gly Phe Thr Phe Asn Asp His Trp
1               5

<210> SEQ ID NO 156
<211> LENGTH: 8
<212> TYPE: PRT
<213> ORGANISM: Artificial Sequence
<220> FEATURE:
<223> OTHER INFORMATION: hSG16.45 vH5 IMGT CDR2

<400> SEQUENCE: 156

Ile Thr Asn Thr Gly Gly Ala Thr
1               5

<210> SEQ ID NO 157
<211> LENGTH: 9
<212> TYPE: PRT
<213> ORGANISM: Artificial Sequence
<220> FEATURE:
<223> OTHER INFORMATION: hSG16.45 vH5 IMGT CDR3

<400> SEQUENCE: 157

Thr Ser Pro Gly Leu Tyr Phe Asp Tyr
1               5
```

<210> SEQ ID NO 158
<211> LENGTH: 5
<212> TYPE: PRT
<213> ORGANISM: Artificial Sequence
<220> FEATURE:
<223> OTHER INFORMATION: hSG16.45 vH6 Kabat CDR1

<400> SEQUENCE: 158

Asp His Trp Met Thr
1               5

<210> SEQ ID NO 159
<211> LENGTH: 17
<212> TYPE: PRT
<213> ORGANISM: Artificial Sequence
<220> FEATURE:
<223> OTHER INFORMATION: hSG16.45 vH6 Kabat CDR2

<400> SEQUENCE: 159

Gly Ile Thr Asn Thr Gly Gly Ala Thr Tyr Tyr Ala Asp Ser Val Lys
1               5                   10                  15

Gly

<210> SEQ ID NO 160
<211> LENGTH: 7
<212> TYPE: PRT
<213> ORGANISM: Artificial Sequence
<220> FEATURE:
<223> OTHER INFORMATION: hSG16.45 vH6 Kabat CDR3

<400> SEQUENCE: 160

Pro Gly Leu Tyr Phe Asp Tyr
1               5

<210> SEQ ID NO 161
<211> LENGTH: 8
<212> TYPE: PRT
<213> ORGANISM: Artificial Sequence
<220> FEATURE:
<223> OTHER INFORMATION: hSG16.45 vH6 IMGT CDR1

<400> SEQUENCE: 161

Gly Phe Thr Phe Asn Asp His Trp
1               5

<210> SEQ ID NO 162
<211> LENGTH: 8
<212> TYPE: PRT
<213> ORGANISM: Artificial Sequence
<220> FEATURE:
<223> OTHER INFORMATION: hSG16.45 vH6 IMGT CDR2

<400> SEQUENCE: 162

Ile Thr Asn Thr Gly Gly Ala Thr
1               5

<210> SEQ ID NO 163
<211> LENGTH: 9
<212> TYPE: PRT
<213> ORGANISM: Artificial Sequence
<220> FEATURE:
<223> OTHER INFORMATION: hSG16.45 vH6 IMGT CDR3

<400> SEQUENCE: 163

Thr Ser Pro Gly Leu Tyr Phe Asp Tyr

```
<210> SEQ ID NO 164
<211> LENGTH: 10
<212> TYPE: PRT
<213> ORGANISM: Rattus norvegicus

<400> SEQUENCE: 164

Leu Ala Thr Ser Ser Val Ser Val Met Tyr
1               5                   10

<210> SEQ ID NO 165
<211> LENGTH: 7
<212> TYPE: PRT
<213> ORGANISM: Rattus norvegicus

<400> SEQUENCE: 165

Ser Thr Ser Ser Leu Ala Ser
1               5

<210> SEQ ID NO 166
<211> LENGTH: 9
<212> TYPE: PRT
<213> ORGANISM: Rattus norvegicus

<400> SEQUENCE: 166

His Gln Trp Ser Ser Asp Pro Pro Thr
1               5

<210> SEQ ID NO 167
<211> LENGTH: 7
<212> TYPE: PRT
<213> ORGANISM: Rattus norvegicus

<400> SEQUENCE: 167

Ser Ser Val Ser Val Met Tyr
1               5

<210> SEQ ID NO 168
<211> LENGTH: 9
<212> TYPE: PRT
<213> ORGANISM: Rattus norvegicus

<400> SEQUENCE: 168

His Gln Trp Ser Ser Asp Pro Pro Thr
1               5

<210> SEQ ID NO 169
<211> LENGTH: 10
<212> TYPE: PRT
<213> ORGANISM: homo sapiens

<400> SEQUENCE: 169

Leu Ala Thr Ser Ser Val Ser Val Met Tyr
1               5                   10

<210> SEQ ID NO 170
<211> LENGTH: 7
<212> TYPE: PRT
<213> ORGANISM: homo sapiens

<400> SEQUENCE: 170

Ser Thr Ser Ser Leu Ala Ser
1               5
```

```
<210> SEQ ID NO 171
<211> LENGTH: 9
<212> TYPE: PRT
<213> ORGANISM: homo sapiens

<400> SEQUENCE: 171

His Gln Trp Ser Ser Asp Pro Pro Thr
1               5

<210> SEQ ID NO 172
<211> LENGTH: 7
<212> TYPE: PRT
<213> ORGANISM: homo sapiens

<400> SEQUENCE: 172

Ser Ser Val Ser Val Met Tyr
1               5

<210> SEQ ID NO 173
<211> LENGTH: 9
<212> TYPE: PRT
<213> ORGANISM: homo sapiens

<400> SEQUENCE: 173

His Gln Trp Ser Ser Asp Pro Pro Thr
1               5

<210> SEQ ID NO 174
<211> LENGTH: 10
<212> TYPE: PRT
<213> ORGANISM: Artificial Sequence
<220> FEATURE:
<223> OTHER INFORMATION: hSG16.45 vK1 Kabat CDR1

<400> SEQUENCE: 174

Arg Ala Ser Ser Ser Val Ser Val Met Tyr
1               5                   10

<210> SEQ ID NO 175
<211> LENGTH: 7
<212> TYPE: PRT
<213> ORGANISM: Artificial Sequence
<220> FEATURE:
<223> OTHER INFORMATION: hSG16.45 vK1 Kabat CDR2

<400> SEQUENCE: 175

Ser Thr Ser Ser Leu Ala Ser
1               5

<210> SEQ ID NO 176
<211> LENGTH: 8
<212> TYPE: PRT
<213> ORGANISM: Artificial Sequence
<220> FEATURE:
<223> OTHER INFORMATION: hSG16.45 vK1 Kabat CDR3

<400> SEQUENCE: 176

His Gln Trp Ser Ser Asp Pro Pro
1               5

<210> SEQ ID NO 177
<211> LENGTH: 7
<212> TYPE: PRT
<213> ORGANISM: Artificial Sequence
<220> FEATURE:
<223> OTHER INFORMATION: hSG16.45 vK1 IMGT CDR1
```

```
<400> SEQUENCE: 177

Ser Ser Val Ser Val Met Tyr
1               5

<210> SEQ ID NO 178
<211> LENGTH: 8
<212> TYPE: PRT
<213> ORGANISM: Artificial Sequence
<220> FEATURE:
<223> OTHER INFORMATION: hSG16.45 vK1 IMGT CDR3

<400> SEQUENCE: 178

His Gln Trp Ser Ser Asp Pro Pro
1               5

<210> SEQ ID NO 179
<211> LENGTH: 10
<212> TYPE: PRT
<213> ORGANISM: Artificial Sequence
<220> FEATURE:
<223> OTHER INFORMATION: hSG16.45 vK2 Kabat CDR1

<400> SEQUENCE: 179

Arg Ala Ser Ser Ser Val Ser Val Met Tyr
1               5                   10

<210> SEQ ID NO 180
<211> LENGTH: 7
<212> TYPE: PRT
<213> ORGANISM: Artificial Sequence
<220> FEATURE:
<223> OTHER INFORMATION: hSG16.45 vK2 Kabat CDR2

<400> SEQUENCE: 180

Ser Thr Ser Ser Leu Ala Ser
1               5

<210> SEQ ID NO 181
<211> LENGTH: 9
<212> TYPE: PRT
<213> ORGANISM: Artificial Sequence
<220> FEATURE:
<223> OTHER INFORMATION: hSG16.45 vK2 Kabat CDR3

<400> SEQUENCE: 181

His Gln Trp Ser Ser Asp Pro Pro Thr
1               5

<210> SEQ ID NO 182
<211> LENGTH: 7
<212> TYPE: PRT
<213> ORGANISM: Artificial Sequence
<220> FEATURE:
<223> OTHER INFORMATION: hSG16.45 vK2 IMGT CDR1

<400> SEQUENCE: 182

Ser Ser Val Ser Val Met Tyr
1               5

<210> SEQ ID NO 183
<211> LENGTH: 9
<212> TYPE: PRT
<213> ORGANISM: Artificial Sequence
<220> FEATURE:
<223> OTHER INFORMATION: hSG16.45 vK2 IMGT CDR3
```

```
<400> SEQUENCE: 183

His Gln Trp Ser Ser Asp Pro Pro Thr
1               5

<210> SEQ ID NO 184
<211> LENGTH: 10
<212> TYPE: PRT
<213> ORGANISM: Artificial Sequence
<220> FEATURE:
<223> OTHER INFORMATION: hSG16.45 vK3 Kabat CDR1

<400> SEQUENCE: 184

Arg Ala Ser Ser Ser Val Ser Val Met Tyr
1               5                   10

<210> SEQ ID NO 185
<211> LENGTH: 7
<212> TYPE: PRT
<213> ORGANISM: Artificial Sequence
<220> FEATURE:
<223> OTHER INFORMATION: hSG16.45 vK3 Kabat CDR2

<400> SEQUENCE: 185

Ser Thr Ser Ser Leu Ala Ser
1               5

<210> SEQ ID NO 186
<211> LENGTH: 9
<212> TYPE: PRT
<213> ORGANISM: Artificial Sequence
<220> FEATURE:
<223> OTHER INFORMATION: hSG16.45 vK3 Kabat CDR3

<400> SEQUENCE: 186

His Gln Trp Ser Ser Asp Pro Pro Thr
1               5

<210> SEQ ID NO 187
<211> LENGTH: 7
<212> TYPE: PRT
<213> ORGANISM: Artificial Sequence
<220> FEATURE:
<223> OTHER INFORMATION: hSG16.45 vK3 IMGT CDR1

<400> SEQUENCE: 187

Ser Ser Val Ser Val Met Tyr
1               5

<210> SEQ ID NO 188
<211> LENGTH: 9
<212> TYPE: PRT
<213> ORGANISM: Artificial Sequence
<220> FEATURE:
<223> OTHER INFORMATION: hSG16.45 vK3 IMGT CDR3

<400> SEQUENCE: 188

His Gln Trp Ser Ser Asp Pro Pro Thr
1               5

<210> SEQ ID NO 189
<211> LENGTH: 10
<212> TYPE: PRT
<213> ORGANISM: Artificial Sequence
<220> FEATURE:
<223> OTHER INFORMATION: hSG16.45 vK5 Kabat CDR1

<400> SEQUENCE: 189
```

```
Leu Ala Thr Ser Ser Val Ser Val Met Tyr
1               5                   10

<210> SEQ ID NO 190
<211> LENGTH: 7
<212> TYPE: PRT
<213> ORGANISM: Artificial Sequence
<220> FEATURE:
<223> OTHER INFORMATION: hSG16.45 vK5 Kabat CDR2

<400> SEQUENCE: 190

Ser Thr Ser Ser Leu Ala Ser
1               5

<210> SEQ ID NO 191
<211> LENGTH: 9
<212> TYPE: PRT
<213> ORGANISM: Artificial Sequence
<220> FEATURE:
<223> OTHER INFORMATION: hSG16.45 vK5 Kabat CDR3

<400> SEQUENCE: 191

His Gln Trp Ser Ser Asp Pro Pro Thr
1               5

<210> SEQ ID NO 192
<211> LENGTH: 7
<212> TYPE: PRT
<213> ORGANISM: Artificial Sequence
<220> FEATURE:
<223> OTHER INFORMATION: hSG16.45 vK5 IMGT CDR1

<400> SEQUENCE: 192

Ser Ser Val Ser Val Met Tyr
1               5

<210> SEQ ID NO 193
<211> LENGTH: 9
<212> TYPE: PRT
<213> ORGANISM: Artificial Sequence
<220> FEATURE:
<223> OTHER INFORMATION: hSG16.45 vK5 IMGT CDR3

<400> SEQUENCE: 193

His Gln Trp Ser Ser Asp Pro Pro Thr
1               5
```

What is claimed is:

1. An isolated antibody or a binding fragment thereof that binds to human B-cell maturation antigen (BCMA), wherein the antibody or binding fragment comprises a mature heavy chain variable region and a mature light chain variable region, wherein the mature heavy chain variable region comprises complementarity determining regions (CDRs) comprising the amino acid sequences of SEQ ID NOs: 60, 61 and 62, and the mature light chain variable region comprises CDRs comprising the amino acid sequences of SEQ ID NOs:90, 91 and 92.

2. The isolated antibody or binding fragment of claim 1, wherein the antibody is a monoclonal antibody.

3. The isolated antibody or binding fragment of claim 1, wherein the mature heavy chain variable region is fused to a heavy chain constant region and the mature light chain variable region is fused to a light chain constant region.

4. The isolated antibody or binding fragment of claim 3, wherein the heavy chain constant region is a mutant form of a natural human constant region and has reduced binding to an Fcγ receptor relative to the natural human constant region.

5. The isolated antibody or binding fragment of claim 3, wherein the heavy chain constant region is of immunoglobulin G1 (IgG1) isotype.

6. The isolated antibody or binding fragment of claim 3, wherein the heavy chain constant region comprises the amino acid sequence of SEQ ID NO:5 and the light chain constant region comprises the amino acid sequence of SEQ ID NO:3.

7. The isolated antibody or binding fragment of claim 3, wherein the heavy chain constant region comprises the amino acid sequence of SEQ ID NO:7 (S293C) and the light chain constant region comprises the amino acid sequence of SEQ ID NO:3.

8. The isolated antibody or binding fragment of claim 3, which is non-fucosylated.

9. The isolated antibody or binding fragment of claim 1, which is an antibody binding fragment.

10. The isolated antibody or binding fragment of claim 9, wherein the antibody binding fragment is selected from the group consisting of a Fab, a Fab', and a F(ab')$_2$.

11. The isolated antibody or binding fragment of claim 1, which is a humanized antibody.

12. The isolated antibody or binding fragment of claim 1, which is a naked antibody or binding fragment.

13. The isolated antibody or binding fragment of claim 1, which is conjugated to a cytotoxic or cytostatic agent.

14. The isolated antibody or binding fragment of claim 13, which is conjugated to a cytotoxic agent.

15. The isolated antibody or binding fragment of claim 14, wherein the cytotoxic agent is conjugated to the antibody or the binding fragment via an enzyme-cleavable linker.

16. The isolated antibody or binding fragment of claim 14, wherein the cytotoxic agent is a DNA minor groove binder.

17. The isolated antibody or binding fragment of claim 16, wherein the cytotoxic agent has the formula:

18. The isolated antibody or binding fragment of claim 14, wherein the cytotoxic agent is monomethyl auristatin (MMAE) or monomethyl auristatin F (MMAF).

19. A bispecific antibody or binding fragment thereof that binds to human B-cell maturation antigen (BCMA), wherein the bispecific antibody or binding fragment comprises a mature heavy chain variable region and a mature light chain variable region, wherein the mature heavy chain variable region comprises complementarity determining regions (CDRs) comprising the amino acid sequences of SEQ ID NOs: 60, 61 and 62, and the mature light chain variable region comprises CDRs comprising the amino acid sequences of SEQ ID NOs:90, 91 and 92.

20. An isolated antibody or a binding fragment thereof that binds to human B-cell maturation antigen (BCMA), wherein the antibody or binding fragment comprises a mature heavy chain variable region comprising the amino acid sequence of SEQ ID NO:13, and a mature light chain variable region comprising the amino acid sequence of SEQ ID NO:19.

21. The isolated antibody or binding fragment of claim 20, wherein the antibody is a monoclonal antibody.

22. The isolated antibody or binding fragment of claim 20, wherein the mature heavy chain variable region is fused to a heavy chain constant region and the mature light chain variable region is fused to a light chain constant region.

23. The isolated antibody or binding fragment of claim 22, wherein the heavy chain constant region is a mutant form of a natural human constant region and has reduced binding to an Fcγ receptor relative to the natural human constant region.

24. The isolated antibody or binding fragment of claim 22, wherein the heavy chain constant region is of immunoglobulin G1 (IgG1) isotype.

25. The isolated antibody or binding fragment of claim 22, wherein the heavy chain constant region comprises the amino acid sequence of SEQ ID NO:5 and the light chain constant region comprises the amino acid sequence of SEQ ID NO:3.

26. The isolated antibody or binding fragment of claim 22, wherein the heavy chain constant region comprises the amino acid sequence of SEQ ID NO:7 (S293C) and the light chain constant region comprises the amino acid sequence of SEQ ID NO:3.

27. The isolated antibody or binding fragment of claim 22, which is non-fucosylated.

28. The isolated antibody or binding fragment of claim 20, which is an antibody binding fragment.

29. The isolated antibody or binding fragment of claim 20, which is a naked antibody or binding fragment.

30. The isolated antibody or binding fragment of claim 20, wherein the antibody or binding fragment is conjugated to a cytotoxic or cytostatic agent.

31. The isolated antibody or binding fragment of claim 20, which is conjugated to a cytotoxic agent.

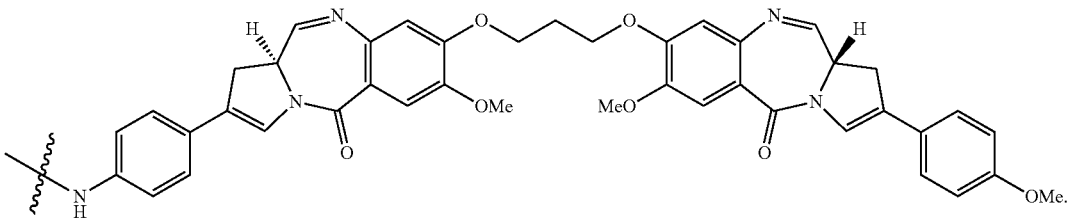 [SMILES: *Nc1ccc(C2=CN3C(=O)c4cc(OC)c(OCCCOc5cc6c(cc5OC)C(=O)N5C=C(c7ccc(OC)cc7)C[C@H]5C=N6)cc4N=C[C@@H]3C2)cc1]

32. The isolated antibody or binding fragment of claim 31, wherein the cytotoxic agent is conjugated to the antibody or the binding fragment via an enzyme-cleavable linker.

33. The isolated antibody or binding fragment of claim 31, wherein the cytotoxic agent is a DNA minor groove binder.

34. The isolated antibody or binding fragment of claim 33, wherein the cytotoxic agent has the formula:

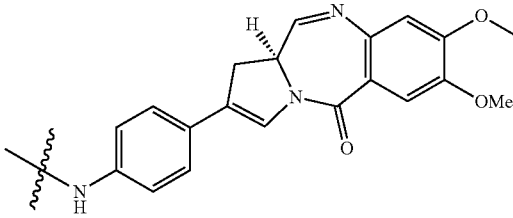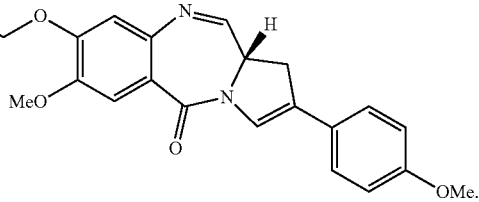

35. The antibody or binding fragment of claim 31, wherein the cytotoxic agent is monomethyl auristatin (MMAE) or monomethyl auristatin F (MMAF).

36. A bispecific antibody or binding fragment thereof, wherein the bispecific antibody or binding fragment comprises a mature heavy chain variable region comprising the amino acid sequence of SEQ ID NO:13, and a mature light chain variable region comprising the amino acid sequence of SEQ ID NO:19 that bind to human B-cell maturation antigen (BCMA).

37. An isolated, monoclonal, immunoglobulin G1 (IgG1) antibody that binds to human B-cell maturation antigen (BCMA), wherein the antibody comprises a mature heavy chain variable region and a mature light chain variable region, wherein the mature heavy chain variable region comprises complementarity determining regions (CDRs) comprising the amino acid sequences of SEQ ID NOs: 60, 61 and 62, and the mature light chain variable region comprises CDRs comprising the amino acid sequences of SEQ ID NOs:90, 91 and 92.

38. A pharmaceutical composition comprising the antibody of claim 37 and a pharmaceutically acceptable carrier.

39. An isolated, monoclonal, immunoglobulin G1 (IgG1) antibody that binds to human B-cell maturation antigen (BCMA), wherein the antibody comprises a mature heavy chain variable region comprising the amino acid sequence of SEQ ID NO:13, and a mature light chain variable region comprising the amino acid sequence of SEQ ID NO:19.

40. A pharmaceutical composition comprising the antibody of claim 39 and a pharmaceutically acceptable carrier.

41. An isolated, monoclonal, non-fucosylated antibody that binds to human B-cell maturation antigen (BCMA), wherein the antibody comprises a mature heavy chain variable region and a mature light chain variable region, wherein the mature heavy chain variable region comprises complementarity determining regions (CDRs) comprising the amino acid sequences of SEQ ID NOs: 60, 61 and 62, and the mature light chain variable region comprises CDRs comprising the amino acid sequences of SEQ ID NOs:90, 91 and 92.

42. The antibody of claim 41, which is an immunoglobulin G1 (IgG1) antibody.

43. The antibody of claim 41, wherein the mature heavy chain variable region is fused to a heavy chain constant region and the mature light chain variable region is fused to a light chain constant region, and wherein the heavy chain constant region comprises the amino acid sequence of SEQ ID NO:5 and the light chain constant region comprises the amino acid sequence of SEQ ID NO:3.

44. A pharmaceutical composition comprising the antibody of claim 41 and a pharmaceutically acceptable carrier.

45. An isolated, monoclonal, non-fucosylated antibody that binds to human B-cell maturation antigen (BCMA), wherein the antibody comprises a mature heavy chain variable region comprising the amino acid sequence of SEQ ID NO:13, and a mature light chain variable region comprising the amino acid sequence of SEQ ID NO:19.

46. The antibody of claim 45, wherein the mature heavy chain variable region is fused to a heavy chain constant region and the mature light chain variable region is fused to a light chain constant region, and wherein the heavy chain constant region comprises the amino acid sequence of SEQ ID NO:5 and the light chain constant region comprises the amino acid sequence of SEQ ID NO:3.

47. A pharmaceutical composition comprising the antibody of claim 46 and a pharmaceutically acceptable carrier.

48. A pharmaceutical composition comprising the antibody of claim 45 and a pharmaceutically acceptable carrier.

49. A composition comprising a plurality of antibodies or binding fragments thereof that bind to human B-cell maturation antigen (BCMA), wherein
   (a) the antibodies or binding fragments comprise a mature heavy chain variable region and a mature light chain variable region, wherein the mature heavy chain variable region comprises complementarity determining regions (CDRs) comprising the amino acid sequences of SEQ ID NOs: 60, 61 and 62, and the mature light chain variable region comprises CDRs comprising the amino acid sequences of SEQ ID NOs:90, 91 and 92; and
   (b) less than 10% of the antibodies in the composition are fucosylated.

50. The composition of claim 49, wherein less than 5% of the antibodies or binding fragments in the composition are fucosylated.

51. The composition of claim 49, wherein less than 3% of the antibodies or binding fragments in the composition are fucosylated.

52. The composition of claim 49, wherein less than 2% of the antibodies or binding fragments in the composition are fucosylated.

53. A composition comprising a plurality of antibodies or binding fragments thereof that bind to human B-cell maturation antigen (BCMA), wherein
   (a) the antibodies or binding fragments comprise a mature heavy chain variable region comprising the amino acid sequence of SEQ ID NO:13, and a mature light chain variable region comprising the amino acid sequence of SEQ ID NO:19; and
   (b) less than 10% of the antibodies in the composition are fucosylated.

54. The composition of claim 53, wherein less than 5% of the antibodies or binding fragments in the composition are fucosylated.

55. The composition of claim 53, wherein less than 3% of the antibodies or binding fragments in the composition are fucosylated.

56. The composition of claim 53, wherein less than 2% of the antibodies or binding fragments in the composition are fucosylated.

57. A composition comprising a plurality of immunoglobulin G1 (IgG1) antibodies that bind to human B-cell maturation antigen (BCMA), wherein
(a) the antibodies comprise a mature heavy chain variable region and a mature light chain variable region, wherein the mature heavy chain variable region comprises complementarity determining regions (CDRs) comprising the amino acid sequences of SEQ ID NOs: 60, 61 and 62, and the mature light chain variable region comprises CDRs comprising the amino acid sequences of SEQ ID NOs:90, 91 and 92; and
(b) less than 5% of the antibodies in the composition are fucosylated.

58. A composition comprising a plurality of immunoglobulin G1 (IgG1) antibodies that bind to human B-cell maturation antigen (BCMA), wherein
(a) the antibodies comprise
(i) a mature heavy chain variable region comprising the amino acid sequence of SEQ ID NO:13, and a mature light chain variable region comprising the amino acid sequence of SEQ ID NO:19; and
(ii) a heavy chain constant region comprising the amino acid sequence of SEQ ID NO:5, and a light chain constant region comprising the amino acid sequence of SEQ ID NO:3; and
(b) less than 5% of the antibodies in the composition are fucosylated.

59. A composition comprising a plurality of monoclonal antibodies with reduced fucosylation that bind to human B-cell maturation antigen (BCMA), wherein
(a) the antibodies in the composition are produced by a process comprising culturing a host cell that express the antibodies in a culture medium suitable to produce antibodies with reduced fucosylation, and isolating the antibodies with reduced fucosylation from the culture medium; and
(b) the antibodies in the composition comprise a mature heavy chain variable region and a mature light chain variable region, wherein the mature heavy chain variable region comprises complementarity determining regions (CDRs) comprising the amino acid sequences of SEQ ID NOs: 60, 61 and 62, and the mature light chain variable region comprises CDRs comprising the amino acid sequences of SEQ ID NOs:90, 91 and 92.

60. The composition of claim 59, wherein the culture medium contains 2-fluorofucose in an amount sufficient to reduce fucosylation of the antibodies.

61. The composition of claim 59, wherein the culture medium is fucose free.

62. A composition comprising a plurality of monoclonal antibodies with reduced fucosylation that bind to human B-cell maturation antigen (BCMA), wherein
(a) the antibodies in the composition are produced by a process comprising culturing a host cell that expresses the antibodies in a culture medium suitable to produce antibodies with reduced fucosylation, and isolating the antibodies with reduced fucosylation from the culture medium; and
(b) the antibodies in the composition comprise a mature heavy chain variable region comprising the amino acid sequence of SEQ ID NO:13, and a mature light chain variable region comprising the amino acid sequence of SEQ ID NO:19.

63. The composition of claim 62, wherein the culture medium contains 2-fluorofucose in an amount sufficient to reduce fucosylation of the antibodies.

64. The composition of claim 62, wherein the culture medium is fucose free.

65. A composition comprising a plurality of monoclonal, immunoglobulin G1 (IgG1) antibodies that bind to human B-cell maturation antigen (BCMA), wherein:
(a) the antibodies in composition are produced by process comprising culturing a host cell that expresses the antibodies in a culture medium containing 2-fluorofucose, and isolating the antibodies from the culture medium;
(b) antibodies in the composition comprise a mature heavy chain variable region and a mature light chain variable region, wherein the mature heavy chain variable region comprises complementarity determining regions (CDRs) comprising the amino acid sequences of SEQ ID NOs: 60, 61 and 62, and the mature light chain variable region comprises CDRs comprising the amino acid sequences of SEQ ID NOs:90, 91 and 92; and
(c) less than 5% of the antibodies in the composition are fucosylated.

66. A composition comprising a plurality of monoclonal, immunoglobulin G1 (IgG1) antibodies that bind to human B-cell maturation antigen (BCMA), wherein:
(a) the antibodies in composition are produced by process comprising culturing a host cell that expresses the antibodies in a culture medium containing 2-fluorofucose, and isolating the antibodies from the culture medium;
(b) the antibodies in the composition comprise a mature heavy chain variable region comprising the amino acid sequence of SEQ ID NO:13, and a mature light chain variable region comprising the amino acid sequence of SEQ ID NO:19; and
(c) less than 5% of the antibodies in the composition are fucosylated.

* * * * *

UNITED STATES PATENT AND TRADEMARK OFFICE
CERTIFICATE OF CORRECTION

PATENT NO. : 11,078,291 B2
APPLICATION NO. : 16/411867
DATED : August 3, 2021
INVENTOR(S) : Sussman et al.

It is certified that error appears in the above-identified patent and that said Letters Patent is hereby corrected as shown below:

In the Claims

Claim 7, Column 131, Line 25, "S293C" should read –S239C–

Claim 26, Column 132, Line 36, "S293C" should read –S239C–

Signed and Sealed this
Seventeenth Day of January, 2023

Katherine Kelly Vidal
*Director of the United States Patent and Trademark Office*